US009724078B2

(12) United States Patent
Larsen et al.

(10) Patent No.: US 9,724,078 B2
(45) Date of Patent: Aug. 8, 2017

(54) VACUUM EXPANDED DRY COMPOSITION AND SYRINGE FOR RETAINING SAME

(71) Applicant: Ferrosan Medical Devices A/S, Søborg (DK)

(72) Inventors: Kristian Larsen, Værløse (DK); Michael Wrang Mortensen, Gentofte (DK)

(73) Assignee: Ferrosan Medical Devices A/S, Søborg (DK)

( * ) Notice: Subject to any disclaimer, the term of this patent is extended or adjusted under 35 U.S.C. 154(b) by 0 days.

(21) Appl. No.: 14/895,674

(22) PCT Filed: Jun. 20, 2014

(86) PCT No.: PCT/EP2014/063041
§ 371 (c)(1),
(2) Date: Dec. 3, 2015

(87) PCT Pub. No.: WO2014/202760
PCT Pub. Date: Dec. 24, 2014

(65) Prior Publication Data
US 2016/0120527 A1    May 5, 2016

(30) Foreign Application Priority Data

Jun. 21, 2013  (DK) .................. 2013 70342
Nov. 19, 2013  (EP) .................... 13193427
Feb. 6, 2014   (EP) .................... 14154117

(51) Int. Cl.
| A61B 17/00 | (2006.01) |
| A61L 26/00 | (2006.01) |
| A61M 39/22 | (2006.01) |
| A61M 5/28  | (2006.01) |
| A61M 5/24  | (2006.01) |
| A61M 5/31  | (2006.01) |
| A61M 5/19  | (2006.01) |

(52) U.S. Cl.
CPC ...... *A61B 17/00491* (2013.01); *A61L 26/009* (2013.01); *A61L 26/0038* (2013.01); *A61L 26/0052* (2013.01); *A61L 26/0066* (2013.01); *A61M 5/19* (2013.01); *A61M 5/2448* (2013.01); *A61M 5/284* (2013.01); *A61M 5/3135* (2013.01); *A61M 39/22* (2013.01); *A61L 2300/252* (2013.01); *A61L 2300/254* (2013.01); *A61L 2300/412* (2013.01); *A61L 2300/418* (2013.01); *A61L 2400/04* (2013.01); *A61L 2400/06* (2013.01); *A61M 2005/3123* (2013.01); *A61M 2005/3132* (2013.01)

(58) Field of Classification Search
CPC .......... A61B 17/00491; A61L 2400/04; A61M 2005/3123; A61M 2005/3132; A61M 5/178; A61M 5/284
See application file for complete search history.

(56) References Cited

U.S. PATENT DOCUMENTS

| 2,465,357 | A |   | 3/1949  | Correll et al. |
| 2,465,860 | A |   | 3/1949  | Fleischmann |
| 2,507,244 | A |   | 5/1950  | Correll |
| 2,558,395 | A |   | 6/1951  | Studer |
| 2,899,362 | A |   | 8/1959  | Sieger et al. |
| 3,089,815 | A |   | 5/1963  | Kupelwieser et al. |
| 3,224,434 | A |   | 12/1965 | Molomut et al. |
| 3,514,518 | A |   | 5/1970  | Charier-Vadrot |
| 3,608,593 | A |   | 9/1971  | McCormick et al. |
| 3,678,933 | A |   | 7/1972  | Moore et al. |
| 3,815,580 | A |   | 6/1974  | Oster |
| 3,869,539 | A |   | 3/1975  | Kring et al. |
| 3,892,876 | A |   | 7/1975  | Hobday et al. |
| 3,899,606 | A | * | 8/1975  | Forkner ................ A21D 2/364 426/250 |
| 3,930,052 | A |   | 12/1975 | De Brou et al. |
| 4,002,173 | A |   | 1/1977  | Manning et al. |
| 4,006,220 | A |   | 2/1977  | Gottlieb |
| 4,013,078 | A |   | 3/1977  | Feild |
| 4,098,728 | A |   | 7/1978  | Rosenblatt et al. |
| 4,107,288 | A |   | 8/1978  | Oppenheim et al. |
| 4,124,705 | A |   | 11/1978 | Rothman et al. |
| 4,150,744 | A |   | 4/1979  | Fennimore |
| 4,160,022 | A | * | 7/1979  | Delaney ................... A61K 8/19 206/277 |
| 4,164,559 | A |   | 8/1979  | Miyata et al. |
| 4,179,400 | A |   | 12/1979 | Tsao et al. |

(Continued)

FOREIGN PATENT DOCUMENTS

| BG | 0051589 | 7/1993 |
| BG | 0099900 | 3/1997 |

(Continued)

OTHER PUBLICATIONS

"Formulation and Evaluation of Absorbable Gelatin Sponges," Chapter 3A of Rupali Kale thesis: *Design and Development of Surgical Dressings for Advanced Wound Management* (2010).
"Gelfoam Prescribing Information," Pharmacia & Upjohn (Nov. 1996).
"Gelfoam® Product Brochure," Pharmacia & Upjohn (Jun. 2013).
Final Office Action for U.S. Appl. No. 14/136,578, titled: "Device for Promotion of Hemostasis and/or Wound Healing", dated Feb. 26, 2015 "Dry Haemostatic Composition".
Final Office Action for U.S. Appl. No. 14/136,578, titled: "Device for Promotion of Hemostasis and/or Wound Healing", dated Oct. 29, 2015 "Dry Haemostatic Composition".
Non-Final Office Action for U.S. Appl. No. 14/136,578, titled: "Device for Promotion of Hemostasis and/or Wound Healing", dated: Oct. 2, 2014.

(Continued)

*Primary Examiner* — Anna Falkowitz
(74) *Attorney, Agent, or Firm* — Hamilton, Brook, Smith & Reynolds, P.C.

(57) ABSTRACT

The present disclosure relates to a method for vacuum expansion of a paste prior to freeze-drying said paste to achieve a dry paste composition which reconstitutes efficiently to form a flowable paste upon addition of an aqueous medium. The present disclosure further relates to a syringe for retaining a dry paste composition in a vacuum.

25 Claims, 22 Drawing Sheets

(56) References Cited

U.S. PATENT DOCUMENTS

| | | |
|---|---|---|
| 4,194,392 A | 3/1980 | Lombard et al. |
| 4,208,439 A | 6/1980 | Hsu |
| 4,256,877 A | 3/1981 | Karlsson et al. |
| 4,265,233 A | 5/1981 | Sugitachi et al. |
| 4,280,954 A | 7/1981 | Yannas et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,320,201 A | 3/1982 | Berg et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,416,813 A | 11/1983 | Ikeda et al. |
| 4,424,208 A | 1/1984 | Wallace et al. |
| 4,453,939 A | 6/1984 | Zimmerman et al. |
| 4,482,386 A | 11/1984 | Wittwer et al. |
| 4,492,305 A | 1/1985 | Avery |
| 4,515,637 A | 5/1985 | Cioca |
| 4,522,302 A | 6/1985 | Paikoff |
| 4,536,387 A | 8/1985 | Sakamoto et al. |
| 4,540,410 A | 9/1985 | Wood et al. |
| 4,543,332 A | 9/1985 | Jao et al. |
| 4,549,554 A | 10/1985 | Markham |
| 4,554,156 A | 11/1985 | Fischer |
| 4,557,377 A | 12/1985 | Maloney |
| 4,559,304 A | 12/1985 | Kasai et al. |
| 4,600,574 A | 7/1986 | Lindner et al. |
| 4,640,834 A | 2/1987 | Eibl et al. |
| 4,655,211 A | 4/1987 | Sakamoto et al. |
| 4,685,597 A | 8/1987 | Hirao et al. |
| 4,696,812 A | 9/1987 | Silbering |
| 4,735,616 A | 4/1988 | Eibl et al. |
| 4,743,229 A | 5/1988 | Chu |
| 4,746,514 A | 5/1988 | Warne |
| 4,749,689 A | 6/1988 | Miyata et al. |
| 4,752,466 A | 6/1988 | Saferstein et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,885,161 A | 12/1989 | Cornell |
| 4,887,743 A | 12/1989 | Blake |
| 4,891,359 A | 1/1990 | Saferstein et al. |
| 4,920,158 A | 4/1990 | Murray et al. |
| 4,925,677 A | 5/1990 | Feijen |
| 4,936,835 A | 6/1990 | Haaga et al. |
| 4,946,870 A | 8/1990 | Partain, III et al. |
| 4,965,203 A | 10/1990 | Silbering et al. |
| 4,982,769 A | 1/1991 | Fournier et al. |
| 4,997,753 A | 3/1991 | Dean, Jr. et al. |
| 5,007,916 A | 4/1991 | Linsky et al. |
| 5,017,229 A | 5/1991 | Burns et al. |
| 5,023,082 A | 6/1991 | Friedman et al. |
| 5,024,841 A | 6/1991 | Chu et al. |
| 5,037,740 A | 8/1991 | Tanaka et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,112,750 A | 5/1992 | Tanaka et al. |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,180,583 A | 1/1993 | Hedner |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,281,528 A | 1/1994 | Boctor et al. |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,350,581 A | 9/1994 | Kochinke |
| 5,352,715 A | 10/1994 | Wallace et al. |
| 5,356,614 A | 10/1994 | Sharma |
| 5,356,883 A | 10/1994 | Kuo et al. |
| 5,384,333 A | 1/1995 | Davis et al. |
| 5,385,606 A | 1/1995 | Kowanko |
| 5,387,208 A | 2/1995 | Ashton et al. |
| 5,394,886 A | 3/1995 | Nabai et al. |
| 5,397,704 A | 3/1995 | Boctor et al. |
| 5,399,361 A | 3/1995 | Song et al. |
| 5,401,511 A | 3/1995 | Margalit |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,441,491 A | 8/1995 | Verschoor et al. |
| 5,443,481 A | 8/1995 | Lee |
| 5,447,966 A | 9/1995 | Hermes et al. |
| 5,456,693 A | 10/1995 | Conston et al. |
| 5,462,860 A | 10/1995 | Mach |
| 5,478,352 A | 12/1995 | Fowler |
| 5,503,848 A | 4/1996 | Perbellini et al. |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,599,735 A | 2/1997 | Moslehi |
| 5,614,587 A | 3/1997 | Rhee et al. |
| 5,618,551 A | 4/1997 | Tardy et al. |
| 5,643,596 A | 7/1997 | Pruss et al. |
| 5,645,849 A | 7/1997 | Pruss et al. |
| 5,648,506 A | 7/1997 | Desai et al. |
| 5,658,592 A | 8/1997 | Tanihara et al. |
| 5,660,854 A | 8/1997 | Haynes et al. |
| 5,667,839 A | 9/1997 | Berg |
| 5,669,934 A | 9/1997 | Sawyer |
| 5,672,336 A | 9/1997 | Sharma |
| 5,674,275 A | 10/1997 | Tang et al. |
| 5,690,675 A | 11/1997 | Sawyer et al. |
| 5,690,954 A | 11/1997 | Ilium |
| 5,698,213 A | 12/1997 | Jamiolkowski et al. |
| 5,700,476 A | 12/1997 | Rosenthal et al. |
| 5,712,161 A | 1/1998 | Koezuka et al. |
| 5,714,370 A | 2/1998 | Eibl et al. |
| 5,723,308 A | 3/1998 | Mach et al. |
| 5,743,312 A | 4/1998 | Pfeifer et al. |
| 5,749,895 A | 5/1998 | Sawyer et al. |
| 5,752,974 A | 5/1998 | Rhee et al. |
| 5,770,229 A | 6/1998 | Tanihara et al. |
| 5,779,668 A | 7/1998 | Grabenkort |
| 5,791,352 A | 8/1998 | Reich et al. |
| 5,795,330 A | 8/1998 | Tofighi et al. |
| 5,798,091 A | 8/1998 | Trevino et al. |
| 5,804,203 A | 9/1998 | Hahn et al. |
| 5,823,671 A | 10/1998 | Mitchell et al. |
| 5,824,015 A | 10/1998 | Sawyer |
| 5,853,749 A | 12/1998 | Hobbs |

(56) References Cited

U.S. PATENT DOCUMENTS

| | | |
|---|---|---|
| 5,856,356 A | 1/1999 | Tsouderos et al. |
| 5,861,043 A | 1/1999 | Carn |
| 5,863,496 A | 1/1999 | McElhany |
| 5,874,500 A | 2/1999 | Rhee et al. |
| 5,883,078 A | 3/1999 | Seelich et al. |
| 5,890,610 A | 4/1999 | Jansen et al. |
| 5,895,412 A | 4/1999 | Tucker |
| 5,902,832 A | 5/1999 | Van Bladel et al. |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,959,735 A | 9/1999 | Maris et al. |
| 5,986,168 A | 11/1999 | Noishiki |
| 5,997,895 A | 12/1999 | Narotam et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,056,970 A | 5/2000 | Greenawalt et al. |
| 6,063,061 A | 5/2000 | Wallace et al. |
| 6,066,325 A | 5/2000 | Wallace et al. |
| 6,074,663 A | 6/2000 | Delmottet et al. |
| 6,096,309 A | 8/2000 | Prior et al. |
| 6,099,952 A | 8/2000 | Cercone |
| 6,110,484 A | 8/2000 | Sierra |
| 6,113,948 A | 9/2000 | Heath et al. |
| 6,129,761 A | 10/2000 | Hubbell |
| 6,132,759 A | 10/2000 | Schacht et al. |
| 6,162,241 A | 12/2000 | Coury et al. |
| 6,166,130 A | 12/2000 | Rhee et al. |
| 6,168,788 B1 | 1/2001 | Wortham |
| 6,179,872 B1 | 1/2001 | Bell et al. |
| 6,193,670 B1 | 2/2001 | van Tassel et al. |
| 6,218,176 B1 | 4/2001 | Berthold et al. |
| 6,261,596 B1 | 7/2001 | Li et al. |
| 6,277,394 B1 | 8/2001 | Sierra |
| 6,280,727 B1 | 8/2001 | Prior et al. |
| 6,283,933 B1 | 9/2001 | D'Aiessio et al. |
| 6,300,128 B1 | 10/2001 | Morota et al. |
| 6,303,323 B1 | 10/2001 | Laskey et al. |
| 6,312,474 B1 | 11/2001 | Francis et al. |
| 6,312,725 B1 | 11/2001 | Wallace et al. |
| 6,328,229 B1 | 12/2001 | Duronio et al. |
| 6,334,865 B1 | 1/2002 | Redmond et al. |
| 6,361,551 B1 | 3/2002 | Torgerson et al. |
| 6,364,519 B1 | 4/2002 | Hughes et al. |
| 6,387,413 B1 | 5/2002 | Miyata et al. |
| 6,416,739 B1 | 7/2002 | Rogerson |
| 6,454,787 B1 | 9/2002 | Maddalo et al. |
| 6,458,380 B1 | 10/2002 | Leaderman |
| 6,458,386 B1 | 10/2002 | Schacht et al. |
| 6,458,889 B1 | 10/2002 | Trollsas |
| 6,461,325 B1 | 10/2002 | Delmotte et al. |
| 6,472,162 B1 | 10/2002 | Coelho et al. |
| 6,495,127 B1 | 12/2002 | Wallace et al. |
| 6,548,081 B2 | 4/2003 | Sadozai et al. |
| 6,584,858 B1 | 7/2003 | Miyazawa et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 6,831,058 B1 | 12/2004 | Ikada et al. |
| 6,861,046 B1 | 3/2005 | Appino et al. |
| 6,887,974 B2 | 5/2005 | Pathak |
| 7,052,713 B2 | 5/2006 | Stimmeder |
| 7,056,722 B1 | 6/2006 | Coelho |
| 7,109,163 B2 | 9/2006 | Pendharkar et al. |
| 7,125,860 B1 | 10/2006 | Renier et al. |
| 7,320,962 B2 | 1/2008 | Reich et al. |
| 7,427,607 B2 | 9/2008 | Suzuki |
| 7,435,425 B2 | 10/2008 | Qian et al. |
| 7,547,446 B2 | 6/2009 | Qian et al. |
| 7,833,965 B2 | 11/2010 | Pendharkar et al. |
| 7,871,637 B2 | 1/2011 | Qian et al. |
| 7,923,431 B2 | 4/2011 | Wolff |
| 7,927,626 B2 | 4/2011 | Pendharkar et al. |
| 7,935,371 B2 | 5/2011 | Williams |
| 8,119,160 B2 | 2/2012 | Looney et al. |
| 8,303,981 B2 | 11/2012 | Wallace et al. |
| 8,357,378 B2 | 1/2013 | Wallace et al. |
| 8,512,729 B2 | 8/2013 | Wallace et al. |
| 8,551,941 B2 | 10/2013 | Pendharkar et al. |
| 8,603,511 B2 | 12/2013 | Wallace et al. |
| 8,642,831 B2 | 2/2014 | Larsen et al. |
| 9,265,858 B2 | 2/2016 | Larsen |
| 9,533,069 B2 | 1/2017 | Larsen et al. |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt et al. |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0027146 A1 | 3/2002 | de LaForcade et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0064109 A1 | 4/2003 | Qian et al. |
| 2003/0095993 A1 | 5/2003 | Benz et al. |
| 2003/0162708 A1 | 8/2003 | Wolff |
| 2003/0175410 A1 | 9/2003 | Campbell |
| 2003/0175419 A1 | 9/2003 | Sessa |
| 2003/0181659 A1 | 9/2003 | Naranda et al. |
| 2003/0225378 A1 | 12/2003 | Wilkie et al. |
| 2003/0232746 A1 | 12/2003 | Lamberti et al. |
| 2004/0076647 A1 | 4/2004 | Biering |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2004/0267352 A1 | 12/2004 | Davidson et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0186253 A1 | 8/2005 | Lee et al. |
| 2005/0214277 A1 | 9/2005 | Schaufler |
| 2005/0218541 A1 | 10/2005 | Peng et al. |
| 2005/0245905 A1 | 11/2005 | Schmidt et al. |
| 2005/0284809 A1 | 12/2005 | Looney et al. |
| 2006/0002890 A1 | 1/2006 | Hersel et al. |
| 2006/0067976 A1 | 3/2006 | Ferraro et al. |
| 2006/0068013 A1 | 3/2006 | DiTizio et al. |
| 2006/115805 A1 | 6/2006 | Hansen |
| 2006/0121080 A1 | 6/2006 | Lye et al. |
| 2006/0121104 A1 | 6/2006 | Stern |
| 2006/0147492 A1 | 7/2006 | Hunter et al. |
| 2006/0159733 A1 | 7/2006 | Pendharkar et al. |
| 2006/0167561 A1 | 7/2006 | Odar et al. |

(56) References Cited

U.S. PATENT DOCUMENTS

| | | |
|---|---|---|
| 2006/0189516 A1 | 8/2006 | Yang et al. |
| 2006/0193846 A1 | 8/2006 | Stimmeder |
| 2006/0204490 A1 | 9/2006 | Pendharkar et al. |
| 2006/0255053 A1 | 11/2006 | Li |
| 2006/0282138 A1 | 12/2006 | Ota |
| 2007/0009578 A1 | 1/2007 | Moiler et al. |
| 2007/0025955 A1 | 2/2007 | Lowinger et al. |
| 2007/0086958 A1 | 4/2007 | Drake et al. |
| 2007/0128343 A1 | 6/2007 | Chappa |
| 2007/0160543 A1 | 7/2007 | Moiler |
| 2007/0215235 A1 | 9/2007 | Ranalletta et al. |
| 2007/0250007 A1 | 10/2007 | Shekalim |
| 2007/0264130 A1 | 11/2007 | Mallett |
| 2007/0264301 A1 | 11/2007 | Cleek et al. |
| 2007/0264302 A1 | 11/2007 | Cleek et al. |
| 2008/0085316 A1 | 4/2008 | Qian et al. |
| 2008/0091277 A1 | 4/2008 | Deusch et al. |
| 2008/0095830 A1 | 4/2008 | Van Holten |
| 2008/0199539 A1 | 8/2008 | Baker et al. |
| 2008/0286376 A1 | 11/2008 | Qian et al. |
| 2008/0311172 A1 | 12/2008 | Schapira et al. |
| 2009/0087569 A1 | 4/2009 | Fan et al. |
| 2009/0142396 A1 | 6/2009 | Odar et al. |
| 2010/0028309 A1 | 2/2010 | Odar et al. |
| 2010/0048758 A1 | 2/2010 | Chen et al. |
| 2010/0063459 A1 | 3/2010 | Preiss-Bloom et al. |
| 2010/0143447 A1 | 6/2010 | Hansen et al. |
| 2010/0256671 A1 | 10/2010 | Falus |
| 2010/0292717 A1 | 11/2010 | Petter-Puchner et al. |
| 2010/0318048 A1 | 12/2010 | Hoefinghoff et al. |
| 2011/0045034 A1 | 2/2011 | Nur et al. |
| 2011/0059228 A1 | 3/2011 | Gillick et al. |
| 2011/0092918 A1 | 4/2011 | Jensen et al. |
| 2012/0128653 A1* | 5/2012 | Goessl ............... A61K 38/4833 424/94.64 |
| 2014/0220130 A1 | 8/2014 | Larsen et al. |
| 2015/0037314 A1 | 2/2015 | Larsen |
| 2015/0045830 A1 | 2/2015 | Jensen et al. |
| 2016/0354512 A1 | 12/2016 | Larsen |

FOREIGN PATENT DOCUMENTS

| | | |
|---|---|---|
| CN | 1270240 | 10/2000 |
| DE | 3146841 | 6/1983 |
| DE | 4119140 | 12/1992 |
| DE | 4407875 | 9/1995 |
| EP | 0132983 | 2/1985 |
| EP | 0156649 | 10/1985 |
| EP | 0282316 | 9/1988 |
| EP | 0341007 | 11/1989 |
| EP | 0341745 | 11/1989 |
| EP | 0365705 | 5/1990 |
| EP | 0372966 | 6/1990 |
| EP | 0385916 A2 | 9/1990 |
| EP | 0395758 | 11/1990 |
| EP | 0172710 | 3/1992 |
| EP | 0478827 | 4/1992 |
| EP | 0493387 | 10/1993 |
| EP | 0376931 | 6/1994 |
| EP | 0702081 | 3/1996 |
| EP | 0737467 | 10/1996 |
| EP | 0612252 | 5/1999 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |
| EP | 1084720 | 3/2001 |
| EP | 1140235 | 10/2001 |
| EP | 1174463 | 1/2002 |
| EP | 1258256 | 11/2002 |
| EP | 1283063 | 2/2003 |
| EP | 0790823 | 7/2003 |
| EP | 0891193 | 8/2003 |
| EP | 1484070 | 12/2004 |
| EP | 1095064 | 6/2005 |
| EP | 1649867 | 4/2006 |
| EP | 1361906 | 4/2007 |
| EP | 1414370 | 4/2007 |
| EP | 1059957 | 8/2007 |
| EP | 1608230 | 7/2010 |
| EP | 2 040 724 B1 | 10/2011 |
| FR | 2679772 | 5/1993 |
| FR | 2759980 | 8/1998 |
| GB | 648619 | 1/1951 |
| GB | 697603 | 9/1953 |
| GB | 1037937 | 8/1966 |
| GB | 1199887 | 7/1970 |
| GB | 1584080 | 2/1981 |
| GB | 1591654 | 6/1981 |
| GB | 2266239 | 10/1993 |
| GB | 2393120 | 3/2004 |
| GB | 2414021 | 11/2005 |
| JP | 51-125156 | 11/1976 |
| JP | 59-113889 | 6/1984 |
| JP | 60214728 | 10/1985 |
| JP | 62070318 | 3/1987 |
| JP | 62221357 | 9/1987 |
| JP | 01130519 | 5/1989 |
| JP | 05308969 | 11/1993 |
| JP | 06254148 | 9/1994 |
| JP | 08-024325 | 1/1996 |
| JP | 9-504719 | 5/1997 |
| JP | 10-507666 | 7/1998 |
| JP | 2002/513308 | 5/2002 |
| JP | 2004002271 | 1/2004 |
| JP | 2006-296896 | 11/2006 |
| JP | 07090241 | 4/2007 |
| JP | 2010228932 | 10/2010 |
| KR | 910007847 | 10/1991 |
| KR | 100751046 | 8/2007 |
| WO | WO 83/01244 | 4/1983 |
| WO | WO 86/00912 | 2/1986 |
| WO | WO 89/02730 | 4/1989 |
| WO | WO 90/13320 | 11/1990 |
| WO | WO 92/21354 | 12/1992 |
| WO | WO 92/22252 | 12/1992 |
| WO | WO 93/06802 | 4/1993 |
| WO | WO 93/06855 | 4/1993 |
| WO | WO 93/10768 | 6/1993 |
| WO | WO 93/21908 | 11/1993 |
| WO | WO 94/08552 | 4/1994 |
| WO | WO 94/17840 | 8/1994 |
| WO | WO 94/27630 | 12/1994 |
| WO | WO 95/12371 | 5/1995 |
| WO | WO 95/15747 | 6/1995 |
| WO | WO 95/25748 | 9/1995 |
| WO | WO 95/31955 | 11/1995 |
| WO | WO 96/04025 | 2/1996 |
| WO | WO 96/06883 | 3/1996 |
| WO | WO 96/07472 | 3/1996 |
| WO | WO 96/10374 | 4/1996 |
| WO | WO 96/10428 | 4/1996 |
| WO | WO 96/12447 | 5/1996 |
| WO | WO 96/14368 | 5/1996 |
| WO | WO 96/16643 | 6/1996 |
| WO | WO 96/39159 | 12/1996 |
| WO | WO 96/40033 | 12/1996 |
| WO | WO 97/17023 | 5/1997 |
| WO | WO 97/17024 | 5/1997 |
| WO | WO 97/17025 | 5/1997 |
| WO | WO 97/29792 | 8/1997 |
| WO | WO 97/37694 | 10/1997 |
| WO | WO 98/08550 | 3/1998 |
| WO | WO 98/31403 | 7/1998 |
| WO | WO 98/34546 | 8/1998 |
| WO | WO 98/36784 | 8/1998 |
| WO | WO 98/43092 | 10/1998 |
| WO | WO 98/44963 | 10/1998 |
| WO | WO 98/51282 | 11/1998 |
| WO | WO 99/04828 | 2/1999 |
| WO | WO 99/12032 | 3/1999 |
| WO | WO 99/13902 | 3/1999 |

(56) References Cited

FOREIGN PATENT DOCUMENTS

| | | |
|---|---|---|
| WO | WO 99/38606 | 8/1999 |
| WO | WO 99/44901 | 9/1999 |
| WO | WO 99/45938 | 9/1999 |
| WO | WO 99/51208 | 10/1999 |
| WO | WO 00/09018 | 2/2000 |
| WO | WO 00/18301 | 4/2000 |
| WO | WO 00/27327 | 5/2000 |
| WO | WO 00/61201 | 10/2000 |
| WO | WO 00/74742 | 12/2000 |
| WO | WO 00/76533 | 12/2000 |
| WO | WO 01/13956 | 3/2001 |
| WO | WO 01/28603 | 4/2001 |
| WO | WO 01/34206 | 5/2001 |
| WO | WO 01/54735 | 8/2001 |
| WO | WO 01/66161 | 9/2001 |
| WO | WO 01/97826 | 12/2001 |
| WO | WO 02/18450 | 3/2002 |
| WO | WO 02/22059 | 3/2002 |
| WO | WO 02/22184 | 3/2002 |
| WO | WO 02/40068 | 5/2002 |
| WO | WO 02/058749 | 8/2002 |
| WO | WO 02/064182 | 8/2002 |
| WO | WO 02/070594 | 9/2002 |
| WO | WO 03/004072 | 1/2003 |
| WO | WO 03/007845 | 1/2003 |
| WO | WO 03/024426 | 3/2003 |
| WO | WO 03/024429 | 3/2003 |
| WO | WO 03/055531 | 7/2003 |
| WO | WO 03/070110 | 8/2003 |
| WO | WO 03/094983 | 11/2003 |
| WO | WO 2004/028404 | 4/2004 |
| WO | WO 2004/028423 | 4/2004 |
| WO | WO 2004/028583 | 4/2004 |
| WO | WO 2004/029095 | 4/2004 |
| WO | WO 2004/030711 | 4/2004 |
| WO | WO 2004/035629 | 4/2004 |
| WO | WO 2004/053051 | 6/2004 |
| WO | WO 2004/075650 | 9/2004 |
| WO | WO 2004/084869 | 10/2004 |
| WO | WO 2004/108035 | 12/2004 |
| WO | WO 2004/108179 | 12/2004 |
| WO | WO 2004/108418 A1 | 12/2004 |
| WO | WO 2005/000265 | 1/2005 |
| WO | WO 2005/009225 | 2/2005 |
| WO | WO 2005/041811 | 5/2005 |
| WO | WO 2005/044285 | 5/2005 |
| WO | WO 2005/062889 | 7/2005 |
| WO | WO 2005/063217 A1 | 7/2005 |
| WO | WO 2005/072700 | 8/2005 |
| WO | WO 2005/084650 A1 | 9/2005 |
| WO | WO 2005/107713 | 11/2005 |
| WO | WO 2006/005340 | 1/2006 |
| WO | WO 2006/031358 | 3/2006 |
| WO | WO 2006/034568 | 4/2006 |
| WO | WO 2006/063758 | 6/2006 |
| WO | WO 2006/128471 | 12/2006 |
| WO | WO 2007/001926 | 1/2007 |
| WO | WO 2007/018887 A2 | 2/2007 |
| WO | WO 2007/092618 A2 | 8/2007 |
| WO | WO 2007/133699 | 11/2007 |
| WO | WO 2007/137839 | 12/2007 |
| WO | WO 2008/016983 | 2/2008 |
| WO | WO 2008/051758 | 5/2008 |
| WO | WO 2008/090555 | 7/2008 |
| WO | WO 2009/109194 | 9/2009 |
| WO | WO 2009/109963 | 9/2009 |
| WO | WO 2009/131752 A2 | 10/2009 |
| WO | WO 2011/047753 A1 | 4/2011 |
| WO | WO 2011/151384 | 12/2011 |
| WO | WO 2011/151386 | 12/2011 |
| WO | WO 2011/151400 | 12/2011 |
| WO | WO 2012/146655 | 11/2012 |
| WO | WO 2013/053753 | 4/2013 |
| WO | WO 2013/053755 | 4/2013 |
| WO | WO 2013/053759 | 4/2013 |
| WO | WO 2013/060770 | 5/2013 |
| WO | WO 2013/131520 A2 | 9/2013 |
| WO | WO 2013/185776 A1 | 12/2013 |
| WO | WO 2014/086996 | 6/2014 |
| WO | WO 2015/086028 A1 | 6/2015 |

OTHER PUBLICATIONS

Non-Final Office Action for U.S. Appl. No. 14/136,578, titled: "Device for Promotion of Hemostasis and/or Wound Healing", dated: Oct. 29, 2015.
Non-Final Office Action for U.S. Appl. No. 14/516,728 dated Apr. 14, 2015 "Dry Haemostatic Composition".
Non-Final Office Action for U.S. Appl. No. 14/516,728, titled: "Dry Haemostatic Composition" dated Nov. 25, 2014.
Notice of Allowance for U.S. Appl. No. 14/516,728, titled: "Dry Haemostatic Composition" dated Nov. 27, 2015.
26th Annual Symposium: Clinical Update in Anaesthesiology, Surgery and Perioperative Medicine, Jan. 20-25, 2008.
Ansell, J., et al., "Gelfoam and Autologous Clot Embolization: Effect on Coagulation," *Investigative Radiology*, 13: 115-120 (1978).
Arai, K., et al., "Clinical Effect of Thrombin-Collagen Sponge Sheet in Surgical Field," Chiryo (Pharmacology and Treatment), 11(5):413-418 (1983). (English translation of Office Action for Japanese counterpart application 2010-547957, Title: Device for Promotion of Hemostasis and/or Wound Healing, being provided to satisfy "concise explanation" requirement under 37 C.F.R. 1.98(a)(3)).
Barrow, D.L., et al., "The Use of Greater Omentum Vascularized Free Flaps for Neurosurgical Disorders Requiring Reconstruction", *Journal of Neurosurgery*, 60: 305-311 (1984), Jan. 31, 2017.
Barton, B., et al., "Fibrin Glue as a Biologic Vascular Patch—A Comparative Study," *Journal of Surgical Research*, vol. 40, 1 page; abstract retrieved from http://www.ncbi.nlm.nih.gov on Jan. 3, 2001. (1986).
Baxter, "GentaFleece Collagen Fleece—Version 5: Instructions for Use—Collagen Sponge with Antibiotic Protection for Surgical Use," Retrieved from http://www.advancingbiosurgery.com/en_EU/downloads/ifu_gentafleece.pdf on Mar. 2002, 2 pages. English portion second column of first page.
Baxter, "Product Catalogue: Collagen," 4 pages, retrieved from http://www.baxter-ecommerce.com/ecatalog on Feb. 2, 2006 (2006).
Baxter, "TissuFleece E Package Leaflet," *Baxter International Inc.*, 4 pages, English portion of instructions for use (2003).
Baxter, "TissuFleece E, TissuCone E and TissuFoil E: Biomaterials," *Basic scientific Information*, 9 pages (2003).
Boland, T., et al., "Application of Inkjet Printing to Tissue Engineering," *Biotechnol. J.*, 1: 910-917 (2006).
Boyers, S., et al., "Reduction of Postoperative Pelvic Adhesions in the Rabbit with Gore-Tex Surgical Membrane", *Fertility and Sterility*, 49(6,): 1066-1070 (1988).
Brannon-Peppas, L., et al., "The Equilibrium Swelling Behavior of Porous and Non-Porous Hydrogels," *Absorbent Polymer Technology*, Elsevier, Amsterdam, pp. 67-102 (1990).
Branski, R.C., et al., "Mucosal Wound Healing in a Rabbit Model of Subglottic Stenosis"; Arch Otolaryngol Head Neck Surg, vol. 131, Feb. 2005, p. 153-157.
Brunt and Klausner, "Growth factors speed wound healing", *Nature Biotechnology*, 6(1): 25-30 (1988).
Campbell, P.G., et al., "Engineered Spatial Patterns of FGF-2 Immobilized on Fibrin Direct Cell Organization," *Biomaterials*, 26: 6762-6770 (2005).
Campbell, P.G., et al., "Tissue Engineering with the Aid of Inkjet Printers," *Expert Opin. Biol. Ther.*, 7: 1123-1127 (2007).
Canal, T., et al., "Correlation Between Mesh Size and Equilibrium Degree of Swelling of Polymeric Networks" *Biomedical Materials Research*, 23: 1183-1193 (1989).
Cantor, M.O., et al., "Gelfoam® and Thrombin in treatment of massive gastroduodenal hemorrhage—A preliminary report", *American Journal of Surgery*, 883-887 (Dec. 1950).

(56) References Cited

OTHER PUBLICATIONS

Cantor, M.O., et al., "Gelfoam and Thrombin in Gastroduodenal Bleeding: An Experimental Study," *Journal of Laboratory and Clinical Medicine*, 35(6): 890-893 (1950).
Cantor, M.O., et al., "Gelfoam and Thrombin in Treatment of Massive Upper Gastrointestinal Hemorrhage," *American Journal of Surgery*, 82(2): 230-235 (Aug. 1951).
Cascone, M.G., et al., "Collagen and hyaluronic acid based polymeric blends as drug delivery systems for the release of physiological concentrations of growth hormone." *Journal of Materials science: Materials in Medicine*; 5: 770-774 (1994).
Changez, M., et al., Abstract of "Efficacy of antibiotics-loaded interpenetrating network (IPNs) hydrogel based on poly (acrylic acid) and gelatin for treatment of experimental osteomyelitis: in vivo study.", *Biomaterials*; 26(14): 2095-2104 (2005).
Chaplin, J.M., et al., "Use of an Acellular Dermal Allograft for Dural Replacement: An Experimental Study," *Neurosurgery*, 45(2): 320-327 (1999).
Cheung, D., et al., "Mechanism of Crosslinking of Proteins by Glutaraldehyde IV: In Vitro and In Vivo Stability of a Crosslinked Collagen Matrix," *Connective Tissue Research*, 25: 27-34 (1990).
Choi, Y.S., et al., "Studies on Gelatin-Based Sponges. Part III: A Comparative Study of Cross-linked Gelatin/ Alginate, Gelatin/ Hyaluronate and Chitosan/Hyaluronate Sponges and their Application as a wound dressing in fullthickness skin defect of rat.", *J. of Mat. Sci.; Mat. in Med.*; 12: 67-73 (Jan. 2001).
Choi, Y.S., et al., "Studies on gelatin-containing artificial skin: II. Preparation and characterization of cross-linked gelatin-hyaluronate sponge.", *J. Biomed Mater Res.*, 48: 631-639 (1999).
Christensen, F, et al., "Qualitative Description of the Wurster-Based Fluid-Bed Coating Process," *Drug Dev and Industry Pharmacy*, 23(5): 451-463 (1977).
Chronic Wound Care Guidelines © 2007 http://woundheal.org. documents/final_pocket_guide_treatment.aspx.
Chuang, V.P., et al., "Sheath Needle for Liver Biopsy in High-Risk Patients" *Radiology*, 166: 261-262 (1988).
Coenye, K.E., et al., "A Qualitative Morphological comparison of Two Heamostatic Agents in a Porcine Liver Trauma Model," *Surgical Science*, 4: 359-364 (2013).
Collins, D., et al., "Enemata of Gelfoam Milk Suspension Combined with Thrombin-Solution to Control Massive Hemorrhage Following Anorectal Surgery," *The American Journal of Proctology*, 2: 60-63 (1951).
Collins, R., et al., "Use of Collagen Film as a Dural Substitute: Preliminary Animal Studies," *Journal of Biomedical Materials Research*, 25: 267-276 (1991).
De la Torre, R.A., et al., "Hemostasis and Hemostatic agents in minimally invasive surgery", *Surgery*, 142(4S): S39-S45 (2007).
De Iaco, P.A., et al., "Efficacy of a Hyaluronan Derivative gel in postsurgical adhesion prevention in the presence of inadequate hemostasis." *Surgery*, 130(1): 60-64 (2001).
DeLustro, F., et al., "A Comparative Study of the Biologic and Immunologic Response to Medical Devices Derived From Dermal Collagen," *Journal of Biomedical Materials Research*, 20: 109-120 (1986).
Dembo, M.A., et al., Abstract of "Antiseptic hemostatic preparations, their properties and study", Lech. Prep. Krovi Tkanei; pp. 139-140 (1974).
Dodd, G.D., et al., "Minimally invasive treatment of malignant hepatic tumors. At the threshold of a major breakthrough", *Radiographies*, 20: 9-27 (2000).
Drognitz, O., et al., Abstract of "Release of vancomycin and teicoplanin from a plasticized and resorbable gelatin sponge: in vitro investigation of a new antibiotic delivery system with glycopeptides"; *Indection Germany* (Minich); 34(1): 29-34 (2006).
Duchene, D., et al., "Pharmaceutical and Medical Aspects of Bioadhesive Systems for Drug Administration," *Drug Dev and Industr Pharmacy*, 14(2&3):283-318 (1988).

Edgerton, M., et al., "Vascular Hamatomas and Hemagiomas: Classification and Treatment," *Southern Medical Journal*, 75(12): 1541-1547 (1982).
Ellegala, D.B., et al., "Use of FloSeal Hemostatic Sealant in Transsphenoidal Pituitary Surgery: Technical Note."; *Neurosurgery*, 51: 513-516 (Aug. 2002).
English Derwent Abstract of Ranjane reference, Nov. 18, 1997.
Filippi, R., et al., "Bovine Pericardium for Duraplasty: Clinical Results in 32 Patients," *Neurological Review*, 20:103-107 (2001).
Fiss, I., et al., "Use of Gelatin-Thrombin Hemostatic Sealant in Cranial Neurosurgery," *Neurologia Medico-Chirurgica*, 47(10):462-467 (2007).
Flory, P., "Phase Equilibria in Polymer Systems," *Principles of Polymer Chemistry*, 13: 541-594 (1953).
FloSeal Matrix Hemostatic Sealant, Instructions for Use, Retrieved from Internet URL http://www.ctsnet.org/file/vendors/931/pdf/140. pdf [retrieved on Aug. 17, 2005].
Fujii, Y., et al., "Safety of GT XIII (Report 2)—Japanese + English translation," *The Clinical Report*, 20(17) (Dec. 1986).
Gall, R.M., "Control of Bleeding in Endoscopic Sinus Surgery: Use of a Novel Gelatin-Based Hemostatic Agent", *Journal of Otolaryngology*, 31(5): (2002).
Gelfoam absorbable powder. Retrieved from Internet URL: http://www.fda.gov/cdrh/pdf/N18286S012c.pdf [retrieved on May 22, 2009].
Gibble, J.W., et al., "Fibrin glue: the perfect operative sealant?" *Reviews: Transfusion*, 30(8): 741-747 (1990).
Guinto, F., "Preparation of Gelfoam Particles Using an Orthopedic Rasp," *Radiology*, 153:250 (1984).
Gurny, R., et al., "Bioadhesive Intraoral Release Systems: Design, Testing and Analysis," *Biomaterials*, 5: 336-340 (1984).
Hae-Won, K., et al., Abstract of "Porus scaffolds of gelatin-hydroxyapatite nanocomposites obtained by biometic approach: Characterization and antibiotic drug release."; *J. of Biomedical Materials Research*, 74B(2): 686-698 (2005).
Harris, W.H., et al., "Topical Hemostatic Agents for Bone Bleeding in Humans," *The Journal of Bone and Joint Surgery*, 60-A(4): 454-456 (1978).
Heller, J., et al., "Release of Norethindrone from Poly(Ortho Esters)," *Polymer Engineering and Science*, 21: 727-731 (1981).
Herndon, J., et al., "Compression of the Brain and Spinal Cord Following Use of Gelfoam," *Arch. Surg*, 104: 107 (Jan. 1972).
Hieb, L., et al, "Spontaneous Postoperative Cerebrospinal Fluid Leaks Following Application of Anti-Adhesion Barrier Gel," *SPINE*, 26(7): 748-751 (2001).
Hill, et al., "Use of microfibrillar collagen hemostat (avitenet) and thrombin to achieve hemostats after median sternotomy."; *J. Thorac Cardiovasc Surg.*, 108: 1151-1152 (1994).
Hill-West, J.L., et al., "Efficacy of a resorbable hydrogel barrier, oxidized regenerated cellulose and hyaluronic acid in the prevention of ovarian adhesions in a rabbit model."; *Fertility and Sterility*, 62(3): 630-634 (1994).
Hong, S.R., et al., Abstract of "Study on gelatin-containing artificial skin IV: a comparative study on the effect of antibiotic and EGF on cell proliferation during epidermal healing."; *Biomaterials*, 22(20): 2777-2783 (2001).
Hong, Y.M., et al., "The Use of Hemostatic Agents and Sealants in Urology", *The Journal of Urology*, 176: 2367-2374 (2006).
Hood, D., et al., "Efficacy of Topical Hemostat Floseal Matrix in Vascular Surgery," *24th World Congress of the International Society for Cardiovascular Surgery*, Sep. 12-16, 1999, 2 pages.
Hotz, G., et al., "Collagen and Fibrin as Biologic Binders from Granular Hydroxyapatite," *Deutsche Zeitschrift fur Mund-Kieferund Gesichts-Chirurgie*, 13(4): 296-300 (1989). Abstract retrieved from http://www.ncbi.nlm.nih.gov on Jan. 3, 2001.
International Preliminary Examination Report for International Application No. PCT/DK03/00855, "Gelatine-Based Materials as Swabs", completed Jun. 2, 2005.
International Preliminary Report on Patentability (Corrected Version) for International Application No. PCT/DK2005/000063, "Haemostatic Sprays and Compositions", completed Nov. 6, 2006.

(56) References Cited

OTHER PUBLICATIONS

International Preliminary Report on Patentability for International Application No. PCT/DK2005/000475, "Haemostatic Composition Comprising Hyaluronic Acid", completed Aug. 16, 2006.
International Preliminary Report on Patentability for International Application No. PCT/DK2007/050196, "Wound or Tissue Dressing Comprising Lactic Acid Bacteria", completed May 29, 2009.
International Preliminary Report on Patentability for International Application No. PCT/DK2009/050048, "Device for Promotion of Hemostasis and/or Wound Healing", completed Sep. 6, 2010.
International Preliminary Report on Patentability for International Application No. PCT/DK2013/050054, "Pressurized Container Containing Haemostatic Paste", issued Sep. 9, 2014.
International Preliminary Report on Patentability from counterpart International Application No. PCT/DK2011/050082, "A Method for Promotion of Hemostasis and/or Wound Healing", mailed Jul. 6, 2012.
International Search Report & Written Opinion of the International Searching Authority for International Application No. PCT/DK2007/050196, "Wound or Tissue Dressing Comprising Lactic Acid Bacteria", mailed Apr. 23, 2008.
International Search Report and Written Opinion of the International Searching Authority from counterpart International Application No. PCT/DK2011/050082, "A Method for Promotion of Hemostasis and/or Wound Healing", mailed Jun. 21, 2011.
International Search Report for International Application No. PCT/DK2003/000855, "Gelatine-Based Materials as Swabs", mailed Oct. 8, 2004.
International Search Report for International Application No. PCT/DK2005/000063, "Haemostatic Sprays and Compositions", received Jul. 28, 2005.
International Search Report for International Application No. PCT/DK2005/000475, "Haemostatic Composition Comprising Hyaluronic Acid", mailed Oct. 25, 2005.
International Search Report for International Application No. PCT/DK2009/050048, "Device for Promotion of Hemostasis and/or Wound Healing", mailed on Apr. 6, 2010.
International Search Report for International Application No. PCT/DK2013/050054, "Pressurized Container Containing Haemostatic Paste", mailed Sep. 10, 2013.
International Search Report for International Application No. PCT/DK2013/050191, "Dry Haemostatic Composition", mailed Aug. 21, 2013.
International Search Report for International Application No. PCT/EP2014/063041 "Vacuum Expanded Dry Composition and Syringe for Retaining Same"; Date of Mailing: Dec. 30, 2015.
Jeong, B., et al., "Biodegradable Block Copolymers as Injectable Drug-Delivery Systems," *Nature*, 388: 860-862 (1997).
Jonas, R., et al., "A new sealant for knitted Dacron prostheses: Minimally cross-linked gelatin," *Journal of Vascular Surgery*, 7(3): 414-419 (1988).
Katayama, T., et al., "GT XIII safety ($3^{rd}$ report)—Japanese + English translation," *The Clinical Report*, vol. 20 (1986).
Kelly M.J. et al., "The value of an operative wound swab sent in transport medium in the prediction of later clinical wound infection: A controlled clinical and bacteriological evaluation.", *Brit. J. Surgery*, 65: 81-88 (1978).
Kim, K., et al., "Reduction in Leg Pain and Lower-Extremity Weakness with Oxiplex/SP Gel for 1 Year after Laminevtomy, Laminotomy, and Disectomy," *Neurosurgical Focus*, 17: 1-6 (2004).
Kline, D., et al., "Dural Replacement with Resorbable Collagen," *Archives of Surgery*, 91: 924-929 (1965).
Knopp, U., "A New Collagen Foil Versus a Cadaveric Dura Graft for Dural Defects—A Comparative Animal Experimental Study," *European Association of Neurosurgical Societies—Proceedings of the $12^{th}$ European Congress of Neurosurgery*, Lisbon, 17 pages (2003).

Koçak, I., et al., "Reduction of adhesion formation with cross-linked hyaluronic acid after peritoneal surgery in rats.", *Fertility and Sterility*, 72(5): 873-878 (1999).
Kofidis, T., et al., "Clinically Established Hemostatis Scaffold (Tissue Fleece) as Biomatrix in Tissue and Organ Engineering Research," *Tissue Engineering*, 9: 517-523 (2003).
Kost J., and Langer R., "Equilibrium Swollen Hydrogels in Controlled Release Applications," *Ch. 5: Hydrogels in Medicine and Pharmacy, vol. III: properties and Applications*, N. Peppas ed., pp. 95-108 (1987).
Krill, D., et al., "Topical Thrombin and Powdered Gelfoam: An Efficient Hemostatic Treatment for Surgery," *Journal of Tennessee Dental Association*, 66(2): 26-27 (1986).
Kuhn, J., et al., "Bilateral Subdural Heamatomata and Lumbar Pseudomeningocele Due to a Chronic Leakage of Liquor Cerebrospinalis after a Lumbar Disectomy with the Application of ADCON-L Gel," *Journal of Neurology, Neurosergery & Psychiatry*, 76: 1031-1033 (2005).
Langer, R., et al., "Chemical and Physical Structure of Polymers as Carriers for Controlled Release of Bioactive Agents: A Review," *Journal of Macromolecular Science—Reviews in Macromolecular Chemistry and Physics*, C23: 61-126 (1983).
Laquerriere, A., et al., "Experimental Evaluation of Bilayered Human Collagen as a Dural Substitute," *Journal of Neurosurgery*, 78: 487-491 (1993).
Larson, P., "Topical Hemostatic Agents for Dermatologic Surgery," *Journal of Dermatologic Surgery & Oncology*, 14: 623-632 (1988).
Larsson, B., et al., "Surgicel®—an absorbable hemostatic material—in prevention of peritoneal adhesion in rats."; *Acta Chir Scand.*, 26(144): 375-378 (1978).
Laurent, C., et al., "Hyaluronic acid reduces connective tissue formation in middle ears filled with absorbable gelatin sponge: An experimental study.", *AM. J.Otolaryngol*, 7: 181-186 (1986).
Le, A., et al., "Unrecognized Durotomy After Lumbar Discectomy: A Report of Four Cases Associated with the Use of ADCON-L," *Spine*, 26(1): 115-118 (2001).
Lee, J., et al., "Experimental Evaluation of Silicone-Coated Dacron and Collagen Fabric-Film Laminate as Dural Substitutes," *Journal of Neurosurgery*, 27: 558-564 (1967).
Lee, P., "Interpretation of Drug-Release Kinetics from Hydrogel Matrices in Terms of Time-Dependent Diffusion Coefficients," *Controlled-Release Technology—Pharmaceutical Applications, Ch. 5, ACS Symposium Series* 348, pp. 71-83 (1986).
Leong, K., et al., "Polyanhydrides for Controlled Release of Bioactive Agents," *Biomaterials*, 7: 364-371 (1986).
Leong, K., et al., "Polymeric Controlled Drug Delivery," *Advanced Drug Delivery Reviews*, 1: 199-233 (1987).
Lewis, K., et al., "Comparison of Two Gelatin and Thrombin Combination Hemostats in a Porcine Liver Abrasion Model," *Journal of Investigative Surgery*, 26: 141-148 (2013).
Li, G., et al., "Evaluation of esterified hyaluronic acid as middle ear-packing material.", *Arch Otolaryngol Head Neck Surg*, 127: 534-539 (2001).
Loeb, J, "The Influence of Electrolytes Upon the Osmotic Pressure of Gelatin Solutions", *J. Biol. Chem.*, 35: 497-508 (1918).
Luengo, J., et al., "Prevention of peritoneal adhesions by the combined use of Spongostan and 32% Dextran 70: An experimental study in pigs." *Fertility and Sterility*, 29(4): 447-450 (1978).
Masar, E., et al., "Synthesis of Polyurethanes and Investigation of their Hydrolytic Stability," *Journal of Polymer Science: Polymer Symposium*, 66: 259-268 (1979).
Masuzawa, M., et al., "Experimental Study Related to the Hemostasis Action of GT XIII," *The Clinical Report*, 20(2): 471-476 (Feb. 1986).
Matsumoto, K., et al., "A Gelatin Coated Collagen—Polyglycolic Acid Composite Membrane as a Dural Substitute," *American Society for Artificial Internal Organs Journal*, 47: 641-645 (2001).
Maurer, P, et al., "Vicryl (Polyglactin 910) Mesh as a Dural Substitute," *Journal of Neurosurgery*, 63:448-452 (1985).
Maxson, W.S., et al., "Efficacy of a modified oxidized cellulose fabric in the prevention of adhesion formation." *Gynecol. Obstet. Invest.*, 26: 160-165 (1988).

(56) References Cited

OTHER PUBLICATIONS

McClure, J., et al., "Massive Gastroduodenal Hemorrhage: Treatment with Powdered Gelfoam and Buffered Thrombin Solution," *Surgery*, 32: 630-637 (1952).
McPherson, J., et al., "An Examination of the Biologic Response to Injectable, Glutaraldehyde Cross-linked Collagen Implants," *Journal of Biomedical Materials Research*, 20: 93-107 (1986).
McPherson, J., et al., "Development and Biochemical Characterization of Injectable Collagen," *J. Dermatol. Surg. Oncol.*, 12(1): 13-20 (Jul. 7, 1988).
McPherson, J., et al., "The Effects of Heparin on the Physiochemical Properties of Reconstituted Collagen," *Collagen and Related Research*, 1: 65-82 (1988).
McPherson, J., et al., "The Preparation and Physiochemical Characterization of an Injectable Form of Reconstituted, Glutaraldehyde Crosslinked, Bovine Corium Collagen," *Journal of Biomedical Materials Research*, 20: 79-92 (1986).
Meddings, N., et al., "Collagen Vicryl—A New Dural Prosthesis," *Acta Neurochirurgica*, 117: 53-58 (1992).
Mello, L., et al., "Duraplasty with Biosynthetic Cellulose: An Experimental Study," *Journal of Neurosurgery*, 86: 143-150 (1997).
Miller, D., and Peppas, N., "Diffusional Effects During Albumin Adsorption on Highly Swollen Poly(vinyl Alcohol) Hydrogels," *Eur. Polym. J.*, 24(7): 611-615 (1988).
Miller, E.D., et al., "Dose-Dependent Cell Growth in Response to Concentration Modulated Patterns of FGF-2 Printed on Fibrin," *Biomaterials*, 27: 2213-2221 (2006).
Millikan, L., "Treatment of Depressed Cutaneous Scars with Gelatin Matrix Implant: A Multicenter Study," *J. Am. Acad. Dermatol.*, 16: 1155-1162 (1987).
Min et al., "Molecular Weight Changes of Sodium Hyaluronate Powder and Solution by Heat treatment," Matrix Biology Institute, Proceedings of Hyaluronan, Oct. 11-16, 2003.
Mitsuhashi, J., "Invertabrate Tissue Culture Methods," *Springer Lab Manual*, p. 407 (2002).
Moak, E., "Hemostatic Agents: Adjuncts to Control Bleeding," *Today's O.R. Nurse*, pp. 6-10 (1991).
Mueller, K., "Release and Delayed Release of Water-Soluble Drugs from Polymer Beads with Low Water Swelling," *Controlled-Release Technology—Pharmaceutical Applications*, Ch. 11, ACS Symposium Series, 348: 139-157 (1986).
Narotam, P., et al., "A Clinicopathological Study of Collagen Sponge as a Dural Graft in Neurosurgery," *Journal of Neurosurgery*, 82: 406-412 (1995).
Narotam, P., et al., "Experimental Evaluation of Collagen Sponge as a Dural Graft," *British Journal of Neurosurgery*, 7: 635-641 (1993).
Nimni, M., et al., "Chemically Modified Collagen: A Natural Biomaterial for Tissue Replacement," *Journal of Biomedical Materials Research*, 21: 741-771 (1987).
Nimni, M., Ph.D., "The Cross-Linking and Structure Modification of the Collagen Matrix in the Design of Cardiovascular Prosthesis," *Journal of Cardiac Surgery*, 3: 523-533 (1988).
Nogueira, L., et al., Comparison of gelatine matrix-thrombin sealants used during laparoscopic partial nephrectomy, *BJU International*, 102: 1670-1674 (2008).
Notification Concerning Transmittal of International Preliminary Report on Patentability for International Application No. PCT/EP2014/063041 "Vacuum Expanded Dry Composition and Syringe for Retaining Same"; Date of Mailing: Dec. 30, 2015.
Novak, D., "Embolization Materials," *Interventional Radiology*, pp. 295-313 (1990).
O'Neill, P., et al., "Use of Porcine Dermis as a Dural Substitute in 72 Patients," *Journal of Neurosurgery*, 61: 351-354 (1984).
Ofner, C.M. and Bubnis, W.A., "Chemical and Swelling Evaluations of Amino Group Crosslinking in Gelatin and Modified Gelatin Matrices," *Pharma. Res.*, 13: 1821-1827 (1996).
Oyelese, Yinka, et al., "Postpartum Hemhorrage," *Obstetrics and Gynecology Clinics of North America* 34.3, 421-441 (2007).
Oz, M.C., et al., "Controlled clinical trial of a novel hemostatic agent in cardiac surgery.", *Ann Thorac Surg*, 69: 1376-1382 (2000).
Oz, M.C., et al., "Floseal-Matrix: New Generation Topical Hemostatic Sealant", *J. Card. Surg.*, 18: 486-493 (2003).
Palm, S., et al., "Dural Closure with Nonpenetrating Clips Prevents Meningoneural Adhesions: An Experimental Study in Dogs," *Neurosurgery*, 45(4): 875-882 (1999).
Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochirurgica*, 139: 827-838 (1997).
Park, Y-K., et al., "Prevention of Arachnoiditis and Postoperative Tethering of the Spinal Cord with Gore-Tex Surgical Membrane: An Experimental Study with Rats," *Neurosurgery*, 42(4): 813-824 (1998).
Peppas, N. and Barr-Howell, B., "Characterization of the Cross-Linked Structure of Hydrogels," Ch. 2: *Hydrogels in Medicine and Pharmacy, vol. I: Fundamentals*, N. Peppas ed., pp. 27-56 (1986).
Peppas, N. and Brannon-Peppas, L, "Hydrogels at Critical Conditions. Part 1. Thermodynamics and Swelling Behavior," *Journal of Membrane Science*, 48: 281-290 (1990).
Peppas, N. and Khare, A., "Preparation, Structure and diffusional Behavior of Hydrogels in Controlled Release," *Adv. Drug Delivery Reviews*, 11: 1-35 (1993).
Peppas, N. and Korsmeyer, R, "Dynamically Swelling Hydrogels in Controlled Release Applications," Ch. 6: *Hydrogels in Medicine and Pharmacy, vol. III: Properties and Applications*, N. Peppas ed., pp. 109-135 (1987).
Peppas, N. and Lustig, S., "Solute Diffusion in Hydrophilic Network Structures," Ch. 3: *Hydrogels in Medicine and Pharmacy, vol. I: Fundamentals*, N. Peppas ed., pp. 57-83 (1986).
Peppas, N. and Mikos, A., "Preparation Methods and Structure of Hydrogels," Ch. 1: *Hydrogels in Medicine and Pharmacy, vol. I: Fundamentals*, N. Peppas ed., pp. 1-25 (1986).
Peppas, N. and Moynihan, H, "Structure and Physical Properties of Poly(2- Hydroxyethyl Methacrylate) Hydrogels," Ch. 2: *Hydrogels in Medicine and Pharmacy, vol. II: Polymers*, N. Peppas ed., pp. 49-64 (1987).
Peppas, N., "Hydrogels and Drug Delivery," *Current Opinion in Colloid & Interface Science*, 2: 531-537 (1997).
Peppas, N., "Hydrogels in Medicine and Pharmacy," *Hydrogels in Medicine and Pharmacy*, vol. 1. Fundamentals, CRC Press, Boca Raton, FL, 180 pages (1986).
Peppas, N., "Hydrogels in Medicine and Pharmacy," *Hydrogels in Medicine and Pharmacy*, vol. 2. Polymers, CRC Press, Boca Raton, FL, 172 pages (1987).
Peppas, N., "Hydrogels in Medicine and Pharmacy," *Hydrogels in Medicine and Pharmacy*, vol. 3. Properties and Applications, CRC Press, Boca Raton, FL, 196 pages (1987).
Peppas, N., "Hydrogels of Poly (Vinyl Alcohol) and its Copolymers," Ch. 1: *Hydrogels in Medicine and Pharmacy, vol. II: Polymers*, N. Peppas ed., pp. 57 pgs (1987).
Peppas, N., ed., "Other Biomedical Applications of Hydrogels," Ch. 9: *Hydrogels in Medicine and Pharmacy, vol. III: Properties and Applications*, pp. 177-186 (1987).
Pietrucha, K., "New Collagen Implant as Dural Substitute," *Biomaterials*, 12: 320-323 (1991).
Pitt, C., et al., "Biodegradable Drug Delivery Systems Based on Aliphatic Polyesters: Application to Contraceptives and Narcotic Antagonists," *Controlled Release of Bioactive Materials*, R. Baker, ed., (NY: Academic Press) pp. 19-43 (1980).
Porchet, F., et al., "Inhibition of Epidural Fibrosis with ADCON-L: Effect on Clinical Outcome One Year Following Reoperation for Recurrent Lumbar Radiculopathy," *Neurological Research*, 21: 551-560 (1999).
Product leaflet for FloSeal ®Matrix Hemostatic Sealant dated Jul. 2001 (Jul. 2001).
Pschyrembel®—Klinisches Wörterbuch, 261st edition, de Gruyter (2007).
Purdy, P.D., et al., "Microfibrillar collagen model of canine cerebral infarction"; *Strokes*, 20(10): 1361-1367 (Oct. 1989).
Quintavalla, J., et al., "Fluorescently labeled mesenchymal stem cells (MSCs) maintain mutlilineage potential and can be detected

(56) References Cited

OTHER PUBLICATIONS following implantation into Particular cartilage defects.", *Biomaterials*, 23: 109-119 (2002).
Raftery, A., "Absorbable haemostatic materials and intraperitoneal adhesion formation."; Br. J. Surg. 67; 1980; pp. 57-58.
Ratner, B., "Hydrogel Surfaces," Ch. 4: *Hydrogels in Medicine and Pharmacy, vol. I: Fundamentals*, N. Peppas ed., pp. 85-94 (1986).
Raul, J.S., et al., "Utilisation du Polyester Urethane (NEUROPATCH) Comme Substitut Dural," *Neurochirugie*, 49: 83-89, English abstract only on p. 83 (2003).
Reddy, M., et al., "A Clinical Study of a Fibrinogen-Based Collagen Fleece for Dural repair in Neurosergery," *Acta Neurochirurgica*, 144: 265-269 (2002).
Reese, A.C., "Role of fibronectin in wound healing", Report date: Sep. 12, 1986; Annual rept. 1. Oct. 1985-Mar. 31, 1986, Final rept. Oct. 1, 1983-Mar 31, 1986. Corporate Author: Medical Coli of Gerogia Augusta Research Institute. Brunt and Klausner, "Growth factors speed wound healing", *Nature Biotechnology*, 6(1): 25-30 (1988).
Reijnen, M.M.P.J., et al., "Prevention of intra-abdominal abscesses and adhesions using a hyaluronic acid solution in a rat peritonitis model." *Arch Surg.* 134: 997-1001 (1999).
Renkens, K., et al, "A Multicenter, Prospective, Randomized Trial Evaluating a New Hemostatic Agent for Spinal Surgery," *Spine*, 26(15): 1645-1650 (2001).
Riley, S., et al. "Percutaneous Liver Biopsy with Plugging of Needle Track: A Safe Method for Use in Patients with Impaired Coagulation," *Lancet*, p. 436 (1984).
Roda, A., et al., "Protein Microdeposition Using a Conventional Ink-Jet Printer," *BioTechniques*, 28(3): 492-496 (2000).
Romanelli., M.. et al., "Exudate Management Made Easy", downloaded from http://www.woundsinternational.com, 6 pgs., (Jan. 29, 2010).
Rosenblatt, J., et al., "Effect of Electrostatic Forces on the Dynamic Rheological Properties of Injectable Collagen Biomaterials," *Biomaterials*, 13: 878-886 (1982).
Rosenblatt, J., et al., "Injectable Collagen as a pHSensitive Hydrogel," *Biomaterials*, 12: 985-995 (1984).
Ross, J., et al., "Association Between Peridural Scar and Recurrent Radicular Pain After Lumbar Discectomy: Magnetic Resonance Evaluation," *Neurosurgery*, pp. 855-863 (1996).
Rossler, B., et al., "Collagen Microparticles: Preparation and Properties," *Journal of Microencapsulation*, 12: 49-57 (1995).
Sakurabayashi, S., et al., "Clinical evaluation of new hemostatic agent for hemostasis from biopsy wounds in the liver."; Gastroenterological Endoscopy 30:(10) 29 pgs. (Oct. 1988).
Sanfilippo, J.S., et al., "Comparison of avitene, topical thrombin and Gelfoam as sole hemostatic agent in tuboplasties.", *Fertility and Sterility*, 33(3): 311-316 (1980).
San-Galli, F., et al., "Experimental Evaluation of a Collagen-Coated Vicryl Mesh as a Dural Substitute," *Neurosurgery*, 30: 396-401 (1992).
Santomaso, A., et al., "Powder flowability and density rations: the impact of granules packing", *Chemical Engineering Science*, 58: 2857-2874 (2003).
Schramm, V., et al., "Gelfoam Paste Injection for Vocal Cord Paralysis," *The Laryngoscope*, 88: 1268-73 (1978).
Shaffrey, C.I., et al., "Neurosurgical Applications of Fibrin Glue: Augmentation of Dural Closure in 134 Patients," *Neurosurgery*, 26: 207-210 (1990).
Shushan, A., et al., "Hyaluronic acid for preventing experimental postoperative intraperitoneal adhesions.", *Journal of Reproductive Medicine*, 39(5): 398-402 (1994).
Shuxian, M. and Zhili, C., "Clinical Observation of the Treatment of Hemoptysis by Ultrasonic Atomizing Inhalation of Thrombin", *Chinese Journal of Critical Care Medicine*, 16(2): 30 (1996).
Sidman, K., et al., "Biodegradable, Implantable Sustained Release Systems Based on Glutamic Acid Copolymers," *Journal of Membrane Science*, 7: 227-291 (1979).
Sigma-Aldrich Datasheet for "Hank's Balanced Salts," revised Apr. 2007.
Simamora, P., et al., "Controlled delivery of pilocarpine. 2. In-vivo evaluation of Gelfoam® device," *International Journal of Pharmaceutics*, 170(2): 209-214 (1998).
Smith, A., "New and Nonofficial Remedies: Absorbable Gelatin Sponge—Gelfoam-Upjohn," *Council on Pharmacy and Chemistry*, 135(14): p. 921 (1947).
Smith, K., et al., "Delayed Postoperative Tethering of the Cervical Spinal Cord," *Journal of Neurosurgery*, 81: 196-201 (1994).
Solar Biologicals Inc., "Solar-cult sampling products: Pre-moistened cellulose sponge sampling systems", available at www.solarbiologicals.com/samp-sys.htm (Jul. 25, 2002).
Soules , M.R., et al., "The prevention of postoperative pelvic adhesions: An animal study comparing barrier methods with Dextran 70.", *Am. J. Obstet. Gynecol.*, 143(7): 829-834 (1982).
Spence et al., "Cerebellar capillary hemangioblastoma: its histogenesis studied by organ culture and electron microscopy.", *Cancer*, 35(2): 326-341 (Feb. 1975).
Spotnitz, W. D., et al., "Hemostatus, Sealants, and Adhesives: Components of the Surgical Toolbox," *Transfusion*, 48(7):1502-1516 (2008).
Springorum, H., "Die Verwendung von Kollagenfolien Zur Uberbruckung von Defekten des Gleitgewebes bei Achillotenotomien und Achillessehnenrupturen," *Akt. Traumatol.*, 15: 120-121, English abstract only on p. 120 (1985).
Stief, T. W., "Kallikrein Activates Prothrombin," *Clinical and Applied Thrombosis/Hemostasis*, 14.1:97-98 (2008).
Stricker, A., et al., "Die Verwendung von TissuFoil Membran bei der Sinusbodenaugmentation," *Ellipse*, 17: 1-5 (2001). English abstract only on p. 1.
Stuart Transport Medium, Catalog item 1518, p. 215. Retrieved from Internet URL http://www.condalab.com [retrieved on May 27, 2009].
Sugitachi, A., et al., "A Newly Devised Chemo-Embolic Agent, G.T. XIIIADM," Gan. To. Kagaku Ryoho, 12: 1942-1943 (1985). English abstract retrieved from http://www.ncbi.nlm.nih.gov on Jan. 2, 2001.
Sugitachi, A., et al., "Locoregional Therapy in Patients with Malignant Pleural Effusion—Two Different Kinds of 'BAC Therapy'," Gan. To. Kagaku Ryoho, 19: 1640-1643 (1992). English abstract retrieved from http://www.ncbi.nlm.nih.gov on Jan. 3, 2001.
Sugitachi, A., et al., "Preoperative Transcatheter Arterial Chemo—Embolization for Locally Advanced Breast Cancer: Application for New Thrombotic Materials." *Japanese Journal of Surgery*, 13: 456-458 (1992) (English Abstract).
Surgiflo® Essential Prescribing Information, Hemostatic Matrix (Made from Absorbable Gelatin Sponge, U.S.P.), 1 page (2005).
Surgiflo® haemostatic matrix FlexTip, MS0009, 84 pages (2007).
Surgiflo® Prescription Information, Hemostatic Matrix, (Made from SURGIFOAM* Absorbable Gelatin Sponge U.S.P.) plus FlexTip, 2 pages (2008).
Surgiflo® product leaflet, "Surgiflo® Hemostatic Matrix Kit," 5 pages (2012).
Surgiflo® product leaflet, "Surgiflo® Hemostatic Matrix," 12 pages (2009).
Swann, D.A., "Studies on hyaluronic acid—I. The preparation and properties of rooster comb hyaluronic acid", *Biochemica et biophysica acta*, 156: 17-30 (1968).
Taheri, Z., "The Use of Gelfoam Paste in Anterior Cervical Fusion," *Journal of Neurosurgery*, 34: 438 (1971).
Tobin, M., et al., "Plugged Liver Biopsy in Patients with Impaired Coagulation," *Digestive Diseases and Science*, 34: 13-15 (1989).
Tucker, H., "Absorbable Gelatin (Gelfoam) Sponge," Springfield, Illinois, Charles T. Thomas, pp. 3-125 (1965).
Van den Bosch, E., et al., "Gelatin degradation at elevated temperature", *International Journal of Biological Macromolecules*, 32: 129-138 (2003).
Vandelli, M.A., et al., "The effect of the crosslinking time period upon the drug release and the dynamic swelling of gelatin microspheres," *Pharmazie*, 46: 866-869 (1991).

(56) References Cited

OTHER PUBLICATIONS

Vander-Salm, T.J., et al., Abstract of "Reduction of sternal infection by application of topical vancomycin.", *J. of Thoracic and Cardiovascular Surgery*, 98(4): 618-622 (1989).
Verhoeven, A.G., et al., "XV. The use of microporous polymeric powders for controlled release drug delivery systems," *Controlled Drug Delivery*. Ch. 15, International Symposium of the Association for Pharmaceutical Technology (APV), Bad Homburg, Nov. 12-14, 1984, pp. 226-237.
Vinas, F., et al., "Evaluation of Expanded Polytetrafluoroethylene (ePTFE) versus Polydioxanone (PDS) for the Repair of Dura Mater Defects," *Neurological Research*, 21: 262-268 (1999).
Wachol-Drewek, Z., et al., "Comparative investigation of drug delivery of collagen implants saturated in antibiotic solutions and a sponge containing gentamicin.", *Biomaterials*, 17: 1733-1738 (1996).
Wallace, D., "The Relative Contribution of Electrostatic Interactions to Stabilization of Collagen Fibrils," *Biopolymers*, 29: 1015-1026 (1990).
Wallace, D., et al., "Injectable Cross-Linked Collagen with Improved Flow Properties," *Journal of Biomedical Materials Research*, 23: 931-945 (1989).
Warren, W., et al., "Dural Repair Using Acellular Human Dermis: Experience with 200 Cases: Technique Assessment," *Neurosurgery*, 46: 1391-1396 (2000).
Wassersug, J.D., M.D., "Use of Human Thrombin in Some Cases of Pulmonary Hemorrhage" *Pulmonary Hemorrhage*, vol. XVII, pp. 354-356 (Mar. 1950).
Weeks, R., "Microscopy of Soft Materials," *Chapter 1 in Experimental and Computational Techniques in Soft Condensed Matter Physics*, Jeffrey Olafsen, Ed, 2010 (2010).
West et al., "Efficacy of adhesion barriers: Resorbable hydrogel, oxidized regenerated cellulose and hyaluronic acid.", *The Journal of Reproductive Medicine*, 41(3) 149-154 (1996).
Wiesenthal, A.A., et al., Abstract of "New method for packing the external auditory canal, middle ear space, and mastoid cavities after otologic surgery", *The Journal of Otolaryngology*, 28(5): 260-265 (1999).
Wilkinson, H., et al., "Gelfoam Paste in Experimental Laminectomy and Cranial Trephination," *Journal of Neurosurgery*, 54: 664-667 (1981).
Written Opinion for International Application No. PCT/DK2003/000855, "Gelatine-Based Materials as Swabs", Feb. 28, 2005.
Written Opinion for International Application No. PCT/EP2014/063041 "Vacuum Expanded Dry Composition and Syringe for Retaining Same"; Dated: Dec. 21, 2015.
Written Opinion of the International Preliminary Examining Authority for counterpart International Application No. PCT/DK2011/050082, "A Method for Promotion of Hemostasis and/or Wound Healing", mailed Mar. 23, 2012.
Written Opinion of the International Searching Authority (Corrected Version) for International Application No. PCT/DK2005/000063, "Haemostatic Sprays and Compositions", received Jul. 26, 2005.
Written Opinion of the International Searching Authority for International Application No. PCT/DK2005/000475, "Haemostatic Composition Comprising Hyaluronic Acid", received Oct. 24, 2005.
Written Opinion of the International Searching Authority for International Application No. PCT/DK2009/050048, "Device for Promotion of Hemostatis and/or Wound Healing", completed Aug. 31, 2010.
Wu, Y. et al., Abstract of "Design and experimental study of a slow-release antibiotic membrane implant in surgery wound.", *Intern. Des Services de San. Des Forces Armees*; 72(7-9): 194-196 (Sep. 1999).
Xing, Q., et al., "Increasing Mechanical Strength of Gelatin Hydrogels by Divalent Metal Ion Removal", *Sci. Rep.*, 4: 4706: DOI:10.1038/srep04706(2014).
Xu, T., et al., "Viability and electrophysiology of neural cell structures generated by the inkjet printing method", *Biomaterials*, 27: 3580-3588 (2006).
Xu, T., et al., "Inkjet Printing of Viable Mammalian Cells," *Biomaterials*, 26: 93-99 (2005).
Yaping, G., "Observation and Nursing of the Treatment of Hemoptysis of Pulmonary Tuberculosis by Ultrasonic Atomizing Inhalation of Thrombin", *Journal of Qilu Nursing*, 10(2): 126 (Feb. 2004).
Youwen, W. et al., "Clinical Observation of the Therapeutic Efficacy of the Treatment of 15 Patients with Hemoptysis by Ultrasonic Atomizing Inhalation of Thrombin", *Chengdu Medical Journal*, 30(5): 262 (Oct. 2004).
Yuki, N., et al., "Effects of Endoscopic Variceal Sclerotherapy Using GT XIII on Blood Coagulation Tests and the Renal Kallikrein-Kinin System," Gastroentral. Japan, 25: 561-567 (1990). English abstract retrieved from http://www.ncbi.nlm.nih.gov [retrieved on Jan. 2, 2001].
Ziegelaar, B., et al., "The Characterisation of Human Respiratory Epithelial Cells Cultured on Resorbable Scaffords: First Steps Towards a Tissue Engineered Tracheal Replacement," *Biomaterials*, 23: 1425-1438 (2002).
Ziegelaar, B., et al., "Tissue Engineering of a Tracheal Equivalent, Doctoral Thesis," Munich, Germany, Ludwig Maximilians University, 2004, 25 pages (2004).
Zins, M., et al., "US-Guided Percutaneous Liver Biopsy with Plugging of the Needle Track: A Prospective Study in 72 High-Risk Patients," *Radiology*, 184: 841-843 (1992).
Notice of Allowance for U.S. Appl. No. 14/136,578, titled: "Device for Promotion of Hemostasis and/or Wound Healing" dated Sep. 23, 2016.

\* cited by examiner

VACUUM EXPANDED DRY COMPOSITION AND SYRINGE FOR RETAINING SAME

This application is the U.S. National Stage of International Application No. PCT/EP2014/063041, filed Jun. 20, 2014, which designates the U.S., published in English, and claims priority under 35 U.S.C. §§119 or 365(c) to Europe Application No. 14154117.7, filed Feb. 6, 2014; Europe Application No. 13193427.5, filed Nov. 19, 2013 and Danish Application No. PA 2013 70342, filed Jun. 21, 2013. The entire teachings of the above applications are incorporated herein by reference.

FIELD OF INVENTION

The present disclosure relates to a method for vacuum expansion of a paste prior to freeze-drying said paste to achieve a dry paste composition which reconstitutes efficiently to form a flowable paste upon addition of an aqueous medium. The present disclosure further relates to a syringe for retaining a dry paste composition in a vacuum.

BACKGROUND OF INVENTION

Protein-based haemostatic materials such as collagen and gelatine are commercially available in solid sponge and loose or unpacked powder form for use in surgical procedures. Mixing of the loose or unpacked powder with a fluid such as saline or thrombin solution may form a paste or slurry that is useful as a haemostatic composition for use in cases of diffuse bleeding, particularly from uneven surfaces or hard to reach areas, depending on mixing conditions and relative ratios of the materials.

Conventional haemostatic pastes are prepared at the point of use by mechanical agitation and mixing of loose powder and liquid to provide uniformity of the composition. Mixing of the powder and fluid may be conducted in a container, such as a beaker. Such mixing requires transfer of the powder from its original container to the beaker, addition of the fluid to the beaker containing the powder, and then kneading of the mixture to form the paste. Only after the paste is thus formed may the paste be placed into a delivery means or applicator, e.g. a syringe, and applied to the wound.

WO 03/055531 relates to a container comprising a fixed amount of haemostatic agent in powder form, such as gelatine powder. Upon addition of a suitable amount of liquid, mechanical mixing within the container may be performed by closing the lid and shaking the container. The resultant putty-like haemostatic paste can then be removed from the container and applied to a patient to promote haemostasis.

Alternately, attempts have been made to preload one syringe (Syringe I) with loose gelatine powder, and a second syringe (Syringe II) with liquid. When it is time to make a paste, Syringes I and II are connected via a luer lock and the solution in Syringe II is pushed into Syringe I. By attempting to pass the solution and powder repeatedly back and forth between Syringes I and II, a homogeneous paste is eventually formed. Often in a surgical situation, a haemostatic paste with optimal powder: liquid ratio needs to be prepared by mixing in order to generate a homogeneous paste. Mixing a powder with a liquid requires the dry powder to be hydrated which may require longer preparation time in order to achieve a homogeneous paste. Even if such methods of mixing are successful in forming a paste, the time and mechanical effort required to form the paste are undesirable or even unacceptable. Also the mixing can affect the final density of the paste (too intense mixing may result in a lower density paste) and hence inconsistent consistency of the paste from time to time.

Floseal® Haemostatic Matrix (Baxter) is a kit for producing a haemostatic gelatine paste. The gelatine paste is produced by first making a thrombin solution and then transferring the gelatin matrix-thrombin solution mixture back and forth between two connected syringes for a total of at least twenty passes. The paste can then be applied to a bleeding to promote haemostasis directly from the syringe.

Likewise, Surgiflo® Haemostatic Matrix (Ethicon) is a kit for producing a haemostatic gelatine paste comprising thrombin, which is prepared by transferring the gelatin matrix-thrombin solution mixture back and forth between two connected syringes for a total of at least six passes.

US 2005/0284809 relates to a method for preparing a haemostatic paste that more readily absorbs aqueous liquids, such that less mechanical force and time is required in order to form a flowable haemostatic paste. The paste of US 2005/0284809 is prepared from compressed haemostatic powder particles and to prepare the paste, it must be transferred back and forth between connected syringes for a total of at least five passes.

WO 2011/151400 relates to a process for making a dry haemostatic composition comprising a coagulation inducing agent such as thrombin and a biocompatible polymer such as gelatine. The coagulation inducing agent and the biocompatible polymer are mixed to form a paste and the paste is subjected to lyophilisation. The resulting dry composition is reconstituted by transferring the composition and a diluent back and forth between two connected syringes for a total of at least twenty passes as described previously.

WO 2013/185776 discloses a dry paste composition comprising one or more polyols suitable for haemostatic use which reconstitutes spontaneously to form a flowable paste, i.e. without any mixing needed, upon addition of an aqueous medium. The reconstituted paste is suitable for direct application to a patient, e.g. by syringe delivery.

Mixing procedures and manipulations are time consuming which in an Operation Room (OR) setting with bleedings is not acceptable as the surgeon will have to abrupt his procedure while waiting for the haemostat. Mixing may also potentially compromise the sterility of the haemostatic paste and can negatively affect the consistency of the haemostatic paste. A correct paste consistency is important for a satisfactory haemostatic effect. It would be desirable if a haemostatic composition could be provided which eliminates the need for such undesirable mixing requirements. It would also be desirable to provide a paste product in dry form which reliably and consistently reconstitutes to form a flowable paste within seconds.

SUMMARY OF INVENTION

The present disclosure addresses the above problems and thus relates to a dry composition, which upon addition of an adequate amount of an aqueous medium forms a substantially homogenous paste. The invention thus relates to a method for preparing a dry composition comprising the steps of:
  a. providing an agent in powder form and an aqueous medium,
  b. mixing the agent in powder form and the aqueous medium to obtain a paste,
  c. subjecting the paste to a reduced pressure thereby expanding the paste, d. freezing the expanded paste, and
e. drying the paste.

The expanded dried paste reconstitutes efficiently upon addition of a liquid. Preferably, the paste forms independently of external stimuli, such as mixing or stirring of any kind. Thus, in one embodiment, the dry composition reconstitutes spontaneously upon addition of a liquid, i.e. no mechanical mixing is required for a paste to form.

The agent is preferably a biocompatible polymer suitable for use in haemostasis and/or wound healing. Thus, in a preferred aspect, the invention relates to a method for preparing a dry composition comprising the steps of:
  a. providing a biocompatible polymer in powder form, an aqueous medium and optionally one or more hydrophilic compounds, such as one or more polyols,
  b. mixing the biocompatible polymer, the aqueous medium and optionally the one or more hydrophilic compounds to obtain a paste,
  c. subjecting the paste to a reduced pressure thereby expanding the paste,
  d. freezing the expanded paste, and
  e. drying the paste.

The present disclosure further relates to a syringe for retaining a freeze-dried paste, such as the presently disclosed dry paste composition, in a vacuum comprising a barrel comprising a vacuum chamber for containing the paste having an open proximal end and a distal end having a first fluid opening, a connector portion having a second fluid opening and adapted for connection to a liquid receptacle, and a pressure chamber connecting the connector portion and the distal end of the vacuum chamber, a pressure valve located in the pressure chamber and adapted to seal the first and/or second fluid openings in a first position and form a fluid passageway between the first and second fluid openings in a second position, a plunger configured to be axially displaced in the vacuum chamber through the open proximal end, and one or more vacuum bypass channels.

Upon addition of a suitable amount of an aqueous medium to the syringe holding the dried paste, a ready-to-use flowable paste suitable for use in haemostasis and/or wound healing forms spontaneously within seconds. Vacuum freeze-drying and vacuum storage of the dry paste composition may be provided by means of the herein disclosed syringe. Furthermore, mixing with an aqueous medium, subsequent reconstitution and controlled release of the ready-to-use paste may also be provided by means of the herein disclosed syringe.

DESCRIPTION OF DRAWINGS

FIG. 3 shows two possible embodiments of a syringe for use as a container before the paste has been added. Concept 1 encompasses a standard single use syringe and concept 2 encompasses a single use syringe with a lyophilisation bypass in the syringe body. The pressure valve is closed.

FIG. 4 shows the syringes of concept 1 and 2 with an amount of paste.

FIG. 5 shows a syringe fitted with a lyophilisation plunger comprising a bypass (lyo plunger; concept 1) or a syringe comprising a bypass in the syringe body being fitted with a standard plunger (concept 2). The bypasses of both concept 1 and 2 allow for gaseous communication between the product chamber and the outside of the container. Application of low vacuum results in expansion of the paste, i.e. the volume of the paste is greater than before application of vacuum.

FIG. 6 shows the syringes of concepts 1 and 2 after the paste has been frozen. Freezing results in a locked expanded paste structure.

FIG. 7 shows the syringes of concepts 1 and 2 undergoing vacuum freeze-drying. Freeze-drying does not alter the volume of the frozen paste.

FIG. 8 shows the syringes of concepts 1 and 2, wherein the bypasses have been closed with a collapsible shelf. The syringes contain the dry paste in a product chamber with vacuum.

FIG. 9 shows the syringes of concepts 1 and 2 after the vacuum in the freeze-dryer has been released. The vacuum inside the product chamber and the atmospheric pressure outside the product chamber causes the plunger to shift until it comes into contact with the dry paste product.

FIG. 10 shows the syringes of concepts 1 and 2 after assembly of a plunger rod and flanges.

FIG. 11 shows the syringe of concept 1 being sterilised by irradiation.

FIG. 12 shows two different embodiments for reconstituting the dry paste. In a first embodiment (top), the syringe is fitted to a plastic bag holding sterile $H_2O$ or saline. In a second embodiment (bottom), the syringe is fitted to a plastic container holding sterile $H_2O$ or saline, wherein the plastic container is fitted with a movable plunger.

FIG. 13 shows the two embodiments from FIG. 12 after the valve has been opened. Opening of the valve results in the liquid automatically being drawn into the product chamber due to the pressure difference between the product chamber (low pressure) and the liquid container (normal pressure). The paste is spontaneously reconstituted upon contact with the liquid. Mechanical mixing is not required before use of the paste.

FIG. 14 depicts a ready to use paste within a syringe fitted with an applicator tip.

FIG. 19b shows a frontal view of another embodiment of the pressure chamber of the presently disclosed syringe with the pressure valve from FIG. 19a.

Figure 1:
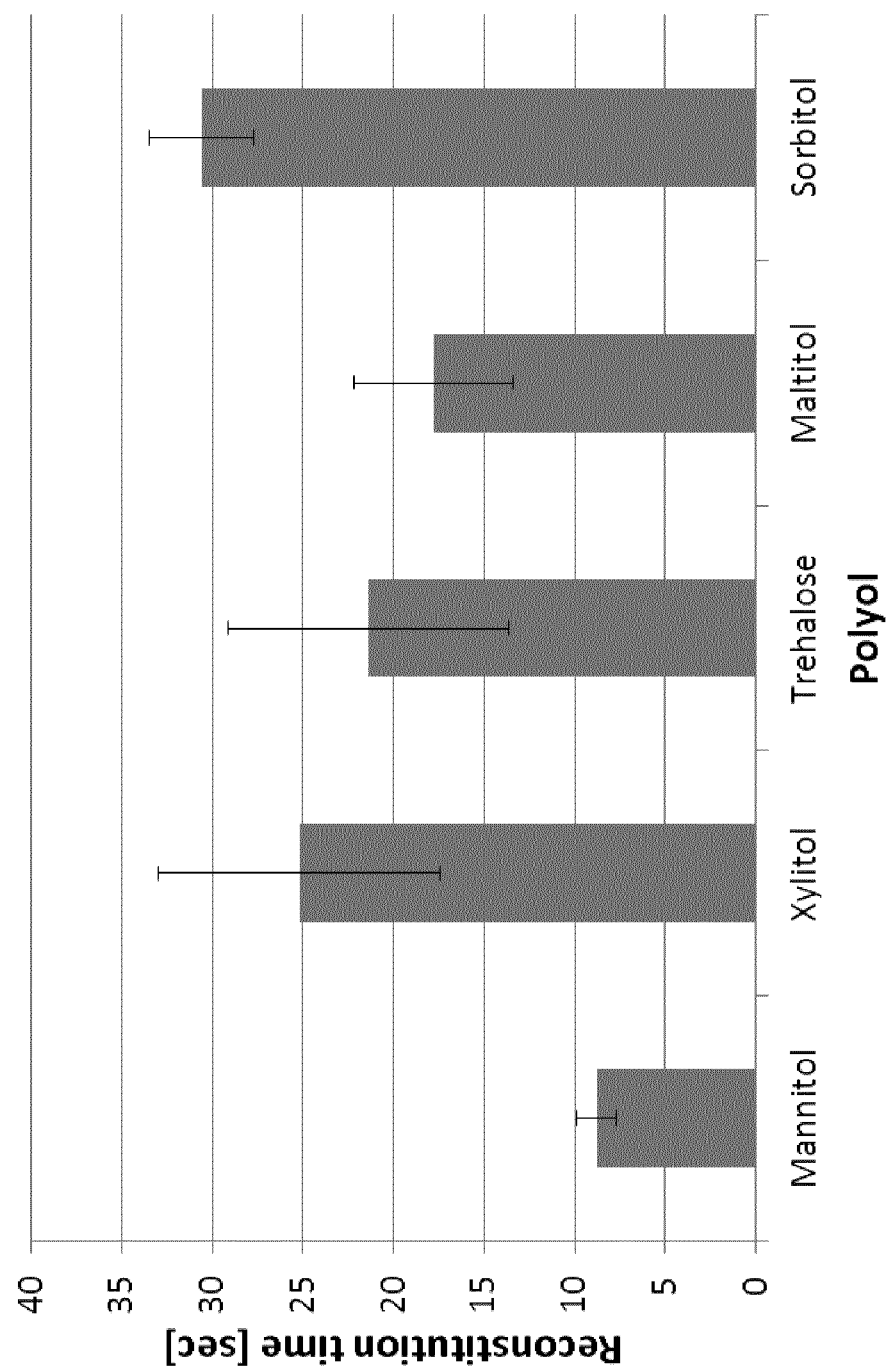
FIG. 1. Average reconstitution time+/−standard deviation of the standard freeze-dried gelatine pastes comprising different polyols of example 1, which have not been vacuum expanded. Inclusion of different polyols in the freeze-dried paste composition resulted in spontaneous reconstitution of the pastes within about 30 seconds.

The drawings are exemplary only and should not be construed as limiting the scope of the invention.

Definitions

"Ambient pressure" is herein used interchangeably with the term "atmospheric pressure". It is the pressure in the surrounding area, i.e. the pressure in the location in which a process takes place.

"Bar" (unit). The bar is a non-SI unit of pressure, defined as exactly equal to 100,000 Pa. It is about equal to the atmospheric pressure on Earth at sea level.

A "bioactive agent" is any agent, drug, compound, composition of matter or mixture which provides some pharmacologic, often beneficial, effect that can be demonstrated in vivo or in vitro. An agent is thus considered bioactive if it has interaction with or effect on a cell tissue in the human or animal body. As used herein, this term further includes any physiologically or pharmacologically active substance that produces a localized or systemic effect in an individual. Bioactive agents may be a protein, such as an enzyme. Further examples of bioactive agents include, but are not limited to, agents comprising or consisting of an oligosaccharide, a polysaccharide, an optionally glycosylated peptide, an optionally glycosylated polypeptide, an oligonucleotide, a polynucleotide, a lipid, a fatty acid, a fatty acid ester and secondary metabolites. It may be used either prophylactically, therapeutically, in connection with treatment of an individual, such as a human or any other animal. The term "bioactive agent" as used herein does not encompass cells, such as eukaryotic or prokaryotic cells.

"Biocompatible" refers to a material's ability to perform its intended function without eliciting any substantial undesirable local or systemic effects in the host.

"Biologically absorbable" or "resorbable" are terms which in the present context are used to describe that the materials of which the said powder are made can be degraded in the body to smaller molecules having a size which allows them to be transported into the blood stream. By said degradation and absorption the said powder materials will gradually be removed from the site of application. For example, gelatine can be degraded by proteolytic tissue enzymes to absorbable smaller molecules, whereby the gelatine, when applied in tissues, typically is absorbed within about 4-6 weeks and when applied on bleeding surfaces and mucous membranes typically within 3-5 days.

"Expansion" is herein defined as an increase in volume and a decrease in density. Thus, if a material is said to be expanded, the total volume of the material is greater than before the expansion without affecting the total weight of the material.

A "gel" is a solid, jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness) and contribute to stickiness (tack). In this way gels are a dispersion of molecules of a liquid within a solid in which the solid is the continuous phase and the liquid is the discontinuous phase. A gel is not a paste or slurry. For example, non-crosslinked gelatin particles are soluble and may form a gel upon contact with an aqueous medium such as water. A gel does not have pores comprising expandable gas or air.

"Haemostasis" is a process which causes bleeding to diminish or stop. Haemostasis occurs when blood is present outside of the body or blood vessels and is the instinctive response for the body to stop bleeding and loss of blood. During haemostasis three steps occur in a rapid sequence. Vascular spasm is the first response as the blood vessels constrict to allow less blood to be lost. In the second step, platelet plug formation, platelets stick together to form a temporary seal to cover the break in the vessel wall. The third and last step is called coagulation or blood clotting. Coagulation reinforces the platelet plug with fibrin threads that act as a "molecular glue". Accordingly, a haemostatic compound is capable of stimulating haemostasis.

"International Unit (IU)". In pharmacology, the International Unit is a unit of measurement for the amount of a substance, based on biological activity or effect. It is abbreviated as IU, UI, or as IE. It is used to quantify vitamins, hormones, some medications, vaccines, blood products, and similar biologically active substances.

A "paste" according to the present disclosure has a malleable, putty-like consistency, such as toothpaste. A paste is a thick fluid mixture of pulverized solid/solid in powder form with a liquid. A paste is a substance that behaves as a solid until a sufficiently large load or stress is applied, at which point it flows like a fluid, i.e. a paste is flowable. Flowables conform efficiently to irregular surfaces upon application. Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes paste to demonstrate properties of fragile matter. A paste is not a gel/jelly. A "slurry" is a fluid mixture of a powdered/pulverized solid with a liquid (usually water). Slurries behave in some ways like thick fluids, flowing under gravity and being capable of being pumped if not too thick. A slurry may functionally be regarded as a thin, watery paste, but a slurry generally contains more water than a paste. A paste according to the present disclosure has pores being compartments comprising an expandable gas, such as air. Substantially water-insoluble powder particles, such as cross-linked gelatine particles, will form a paste upon mixing with an aqueous medium.

"Percentage". If nothing else is indicated, the percentage is percentage by weight: % w/w or wt %.

Ratios are indicated as weight by weight (w:w).

A "reduced pressure" is a pressure below ambient pressure, i.e. a pressure below that of the pressure in the surrounding area in which a certain process operates.

"Spontaneous". The term "spontaneous" is used to describe phenomena arising from internal forces or causes, which are independent of external agencies or stimuli and which happen within a short period of time, i.e. preferably within less than about 30 seconds, more preferred within less than about 20 seconds, even more preferred within less than about 10 seconds or within less than about 5 seconds, such as within less than about 3 seconds, for example less than about 2 seconds.

"Vacuum" is herein defined as a region with a gaseous pressure less than the ambient pressure, i.e. the surrounding atmospheric pressure. At sea level on Earth the atmospheric pressure is approximately 1 bar, i.e. 1000 mbar at 25° C. The below table shows the approximate pressures in "low", "medium" and "high" vacuum at sea level on earth in millibar (mbar).

|  | pressure (mbar) |
| --- | --- |
| Atmospheric pressure | 1000 |
| Low vacuum | 1000 to 100 |
| Medium vacuum | 100 to 0.001 |
| High vacuum | <0.001 |

DETAILED DESCRIPTION OF THE INVENTION

The present disclosure relates to a dry composition, which upon addition of an adequate amount of an aqueous medium forms a substantially homogenous paste.

The invention thus relates to a method for preparing a dry composition comprising the sequential steps of:
a. providing an agent in powder form and an aqueous medium,
b. mixing the agent in powder form and the aqueous medium to obtain a paste,
c. subjecting the paste to a reduced pressure thereby expanding the paste,
d. freezing the expanded paste, and
e. drying the paste.

The expanded dried paste reconstitutes efficiently upon addition of a liquid to form a flowable paste. Preferably, the paste forms independently of external stimuli, such as mixing or stirring of any kind, thus in one embodiment, the dry composition reconstitutes spontaneously upon addition of a liquid to the container holding the dry composition, i.e. no mechanical mixing is required for a paste to form.

The agent in powder form may be any agent in powder form capable of forming a paste when mixed with an aqueous medium. The agent may be cross-linked. Preferably, the agent is a biocompatible polymer suitable for use in haemostasis and/or wound healing, such as a cross-linked haemostatic agent in powder form, for example cross-linked gelatine powder.

Drying is preferably freeze-drying. Steps c) to d) may conveniently be performed directly in the freeze-dryer as one continuous process. Thus, suitable containers holding the paste of step b) may be placed in a freeze-dryer, wherein the paste is expanded by low vacuum, frozen to fix the expanded paste structure and freeze-dried until dry. FIGS. 3 to 14 show different embodiments of the process steps.

In a preferred aspect, the invention relates to a method for preparing a dry composition suitable for use in haemostasis and/or wound healing comprising the sequential steps of:
a. providing a biocompatible polymer in powder form, an aqueous medium, and optionally one or more hydrophilic compounds,
b. mixing the biocompatible polymer, the aqueous medium and optionally the one or more hydrophilic compounds to obtain a paste,
c. subjecting the paste to a reduced pressure thereby expanding the paste,
d. freezing the expanded paste, and
e. drying the paste.

The dried paste is preferably contained within a medical delivery device, such as a syringe. Upon addition of a suitable amount of an aqueous medium to the container holding the dried paste, a ready-to-use flowable paste forms spontaneously within seconds, i.e. no mechanical mixing is required for said paste to form. The flowable paste is substantially homogenous and can be applied directly to a site requiring haemostasis and/or wound healing.

The advantages of the dry composition and the reconstituted paste obtained by the methods of the present disclosure are numerous and include:
  Less time spent preparing the paste, e.g. bleeding can be stopped faster.
  Decreased risk of compromising the sterility of the paste during preparation due to less handling steps.
  Decreased risk of making mistakes during preparation due to the simplified preparation of the paste.
  Optimal consistency of paste obtained every time.
  Reliable and consistent reconstitution within a short time period.
  Bioactive agents, which are unstable in solution may be added to the paste prior to drying and will thus be present in the dry composition of the invention. For example, thrombin may be added to the paste prior to drying, thereby avoiding the time-consuming and error-prone thrombin dilution steps.
  Minimises Operation Room costs since preparation of the currently described product is so simple and fast that there is no reason to pre-prepare haemostatic flowables before surgery which may not be used.

All of the above factors lead to increased patient safety.

Agent in Powder Form

The agent in powder form may be any agent capable of forming a paste when mixed with an aqueous medium. A paste is formed when the powder particles are insoluble in water, i.e. when the powder particles are substantially insoluble in the aqueous medium they are mixed with. Thus the agent in powder form consists of substantially water-insoluble powder particles. Preferably, the agent is a cross-linked biocompatible polymer suitable for use in haemostasis and/or wound healing, such as a cross-linked haemostatic agent in powder form, for example cross-linked gelatine powder. Cross-linking renders the biocompatible polymer substantially insoluble in an aqueous medium.

In one embodiment, the paste of the present disclosure comprises one or more agents in powder form, such as a single biocompatible polymer or a combination of two or more biocompatible polymers.

In a preferred embodiment, the present disclosure relates to a method for preparing a dry composition being a dried paste composition, which reconstitutes spontaneously within seconds upon addition of a suitable amount of an aqueous medium to the container holding the dry composition to form a ready-to-use paste suitable for haemostatic and/or wound healing purposes, i.e. which can be delivered directly to a patient without any further mixing required.

The biocompatible polymer of the present disclosure may be a biologic or a nonbiologic polymer. Suitable biologic polymers include proteins, such as gelatin, collagen, albumin, hemoglobin, casein, fibrinogen, fibrin, fibronectin, elastin, keratin, and laminin; or derivatives or combinations thereof. Particularly preferred is the use of gelatin or collagen, more preferably gelatin. Other suitable biologic polymers include polysaccharides, such as glycosaminoglycans, starch derivatives, xylan, cellulose derivatives, hemicellulose derivatives, agarose, alginate, and chitosan; or derivatives or combinations thereof. Suitable non-biologic polymers will be selected to be degradable by either of two mechanisms, i.e. (1) break down of the polymeric backbone or (2) degradation of side chains which result in aqueous solubility. Exemplary nonbiologic polymers include synthetics, such as polyacrylates, polymethacrylates, polyacrylamides, polyvinyl resins, polylactide-glycolides, polycaprolactones, and polyoxyethylenes; or derivatives or combinations thereof. Also combinations of different kinds of polymers are possible.

In one embodiment the biocompatible polymer is biologically absorbable. Examples of suitable biologically absorbable materials include gelatine, collagen, chitin, chitosan, alginate, cellulose, oxidised cellulose, polyglycolic acid, polyacetic acid and combinations thereof. It will be understood that various forms thereof, such as linear or cross-linked forms, salts, esters and the like are also contemplated for the present disclosure. In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means.

In a preferred embodiment the polymer is cross-linked. Cross-linking usually renders the polymer substantially insoluble in an aqueous medium. Any suitable cross-linking methods known to a person of skill may be used including both chemical and physical cross-linking methods.

In one embodiment of the present disclosure the polymer has been cross-linked by physical means, such as by dry heat. The dry heat treatment is usually performed at temperatures between 100° C. and 250° C., such as about 110° C. to about 200° C. In particular the temperature may be in the range of 110-160° C., e.g. in the range of 110-140° C., or in the range of 120-180° C., or in the range of 130-170° C., or in the range of 130-160° C., or in the range of 120-150° C. The period of time for cross-linking may be optimised by a skilled person and is normally a period between about 10 minutes to about 12 hours, such as about 1 hour to about 10 hours, for example between about 2 hours to about 10 hours, such as between about 4 hours to about 8 hours, for example between about 5 hours to about 7 hours, such as about 6 hours.

In another embodiment, the polymer has been cross-linked by chemical means, i.e. by exposure to a chemical cross-linking agent. Examples of suitable chemical cross-linking agents include but are not limited to aldehydes, in particular glutaraldehyde and formaldehyde, acyl azïde, caboiimides, hexamethylene diisocyanate, polyether oxide, 1,4-butanedioldiglycidyl ether, tannic acid, aldose sugars, e.g. D-fructose, genipin and dye-mediated photo-oxidation. Specific compounds include but are not limited to 1-(3-dimethylaminopropyl)-3-ethylcarboiimide hydrochloride (EDC), dithiobis(propanoic dihydrazide) (DTP), 1-ethyl-3-(3-dimethylamino-propyl)-carbodiimide (EDAC).

In a preferred embodiment, the biocompatible polymer has been obtained from cross-linked sponges of gelatine or collagen, in particular cross-linked sponges of gelatine (such as the commercially available Spongostan® sponges and Surgifoam® sponges). The cross-linked sponges are micronised by methods known in the art to obtain a cross-linked biocompatible polymer in powder form, such as by rotary bed, extrusion, granulation and treatment in an intensive mixer, or milling (e.g. by using a hammer mill or a centrifugal mill).

Spongostan®/Surgifoam® available from Ethicon is a gelatine based cross-linked absorbable haemostatic sponge. It absorbs >35 g of blood/g and within 4-6 weeks it is completely absorbed in the human body.

In one embodiment, the agent in powder form comprises or consists of cross-linked gelatine particles obtained from a micronized porous gelatine sponge, which has been cross-linked by dry heat treatment.

Micronized porous gelatine sponges may be prepared by mixing an amount of soluble gelatine with an aqueous medium in order to create a foam comprising a discontinuous gas phase, drying said foam and crosslinking the dried foam by exposure to dry heat. The obtained crosslinked sponge can be micronized by methods known in the art. The gelatine foam usually has a gelatine concentration from about 1% to 70% by weight, usually from 3% to 20% by weight. Drying is usually performed at about 20° C. to about 40° C. for about 5 to 20 hours. The dried foam is usually crosslinked by exposure to a temperature of about 110° C. to about 200° C. for about 15 minutes to about 8 hours, such as at about 150° C. to about 170° C. for about 5 to 7 hours.

In another embodiment, the agent in powder form comprises or consists of cross-linked gelatine particles obtained from a gelatine hydrogel. A gelatine hydrogel may be prepared by dissolving an amount of gelatine in an aqueous buffer to form a non-cross-linked hydrogel, typically having a solids content from 1% to 70% by weight, usually from 3% to 10% by weight. The gelatin is cross-linked, for example by exposure to either glutaraldehyde (e.g. 0.01% to 0.05% w/w, overnight at 0 DEG to 15 DEG C. in aqueous buffer), sodium periodate (e.g. 0.05 M, held at 0 DEG C. to 15 DEG C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of gamma or electron beam radiation. The resulting crosslinked hydrogels may be fragmented and dried to obtain a gelatine powder. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). When cross-linking with glutaraldehyde, the cross-links are formed via Schiff bases which may be stabilized by subsequent reduction, e.g. by treatment with sodium borohydride. After cross-linking, the resulting granules may be washed in water and optionally rinsed in an alcohol and dried to obtain a gelatine powder. In one embodiment, crosslinked gelatine particles are prepared essentially as described in U.S. Pat. No. 6,066,325.

The cross-linked powder particles are in one embodiment less than approximately 1000 microns in size, i.e. so that they are able to pass through a 1×1 mm sieve.

Generally at least 90% of the powder particles have a diameter of between 1 µm and 1200 µm.

In one embodiment, the average particle diameter is between 1 µm and 1000 µm, such as between 10 µm and 800

μm, for example between 50 μm and 600 μm, such as between 100 μm and 500 μm, for example between 200 μm and 400 μm, such as about 300 μm.

In some applications it is desirable to have a smaller particle size, whereby a smoother paste can be obtained. Thus in one embodiment, the average particle diameter is less than 100 μm, such as less than 50 μm, for example less than 30 μm, such as less than 20 μm, for example less than 10 μm. One example of an application where a smoother paste is desirable is in the control of bone bleeding.

Particles of a certain size distribution can be achieved by passing a powdered composition through one or more sieves having a certain mesh size and collecting the powder which passes through and/or is retained by a certain mesh size. For example, powder particles having a size distribution between approximately 200 μm and 1000 μm can be obtained by collecting the powder which is able to pass through a 1×1 mm sieve but is retained by a 0.2×0.2 mm sieve.

In one embodiment, the paste obtained by mixing the agent in powder form and the aqueous medium comprises between about 10% to about 60% of the biocompatible polymer, for example about 10% to about 50% of the biocompatible polymer, such as about 10% to about 40% of the biocompatible polymer, for example about 10% to about 30% of the biocompatible polymer, such as about 12% to about 25% of the biocompatible polymer, for example about 14% to about 25% of the biocompatible polymer, such as about 15% to about 25% of the biocompatible polymer, for example about 16% to about 20% of the biocompatible polymer, such as about 17% to about 20% of the biocompatible polymer, for example about 18% to about 20% of the biocompatible polymer.

In one embodiment, the paste of the present disclosure comprises more than 10% of the biocompatible polymer, such as more than 15% of the biocompatible polymer, for example more than 16% of the biocompatible polymer, such as more than 17% of the biocompatible polymer, for example more than 18% of the biocompatible polymer, such as more than 19% of the biocompatible polymer, for example more than 20% of the biocompatible polymer.

In one embodiment, the paste of the present disclosure comprises less than 40% of the biocompatible polymer, such as less than 30% of the biocompatible polymer, for example less than 25% of the biocompatible polymer, such as less than 20% of the biocompatible polymer.

In a preferred embodiment, the paste of the present disclosure comprises between about 10% to about 30% of the biocompatible polymer, more preferred between about 15% to about 25% of the biocompatible polymer, such as about 20% of the biocompatible polymer.

After drying, the composition comprises between about 40% and 80% of the biocompatible polymer, such as between about 45% and 80% of the biocompatible polymer, for example between about 50% and 80% of the biocompatible polymer, such as between about 55% and 80% of the biocompatible polymer.

In one embodiment, the composition after drying comprises between about 40% and 80% of the biocompatible polymer, such as between about 45% and 75% of the biocompatible polymer, for example between about 50% and 70% of the biocompatible polymer.

In one embodiment, the dry composition of the present disclosure comprises more than 30% of the biocompatible polymer, such as more than about 40% of the biocompatible polymer, for example more than about 45% of the biocompatible polymer, such as more than about 50% of the biocompatible polymer, for example more than about 55% of the biocompatible polymer, such as more than about 60% of the biocompatible polymer, for example more than about 65% of the biocompatible polymer, such as more than about 70% of the biocompatible polymer, for example more than about 75% of the biocompatible polymer, such as more than about 80% of the biocompatible polymer.

In one embodiment, the dry composition of the present disclosure comprises less than about 80% of the biocompatible polymer, such as less than about 70% of the biocompatible polymer, for example less than about 65% of the biocompatible polymer, such as less than about 60% of the biocompatible polymer, for example less than about 55% of the biocompatible polymer, such as less than about 50% of the biocompatible polymer.

Aqueous Medium

An aqueous medium is used in the methods of the present disclosure for initially preparing the paste, which is subsequently vacuum expanded and dried, and for reconstituting the dried paste.

The aqueous medium of the present disclosure may be any aqueous medium suitable for preparing a paste known to a person of skill, e.g. water, saline or a buffered aqueous medium. The water may be WFI (Water For Injection). It is important that the aqueous medium is selected so that the reconstituted paste product is isotonic when intended for use on a human or animal subject, such as for haemostatic and/or wound healing purposes. The aqueous medium is preferably sterile.

The aqueous medium of the present disclosure is in one embodiment a saline solution.

In one embodiment, the aqueous medium is a calcium chloride solution.

In other embodiments, the aqueous medium is water.

The aqueous medium may also be a buffered aqueous medium suitable for use in a haemostatic paste. Any suitable buffering agent known to a person of skill may be used, such as one or more buffering agents selected from the group consisting of: Sodium citrate; Citric acid, Sodium citrate; Acetic acid, Sodium acetate; K2HPO4, KH2PO4; Na2HPO4, NaH2PO4; CHES; Borax, Sodium hydroxide; TAPS; Bicine; Tris; Tricine; TAPSO; HEPES; TES; MOPS; PIPES; Cacodylate; SSC; MES, or others. The pH of the buffered aqueous medium should be suitable for creating a haemostatic paste intended for human use and can be determined by the skilled person.

The aqueous medium is mixed with the agent in powder form in sufficient amounts to obtain a wet paste. For procedural efficiency, it is sometimes desirable that the paste prior to drying contains less water, i.e. is thicker, than a paste intended for e.g. surgical use so that less water has to be removed in the drying process.

When reconstituting the dried paste, the amount of aqueous medium is adjusted to the amount of the biocompatible polymer for a paste, of a suitable consistency to form.

In one embodiment, the paste of the present disclosure prior to drying comprises less than 99% of water, preferably less than 95% of water.

In one embodiment, the paste of the present disclosure prior to drying comprises between about 50% to about 90% of water, such as between about 55% to about 85% of water, for example between about 60% to about 80% of water, such as about 70% of water.

After drying, the dry composition comprises less than about 5% of water, such as less than about 3% of water, preferably less than about 2% of water, more preferred less than about 1.5% of water, even more preferred less than about 1% of water or even less. Hence, in one embodiment, the dry composition comprises from about 0.1 to about 5% water, such as from about 0.1% to about 2% water.

A low residual water content in the haemostatic composition after drying is desirable as it decreases the risk of microbial growth in the dry composition. Furthermore, a low residual water content is essential if the composition comprises bioactive agents that are unstable in aqueous conditions, such as e.g. thrombin. If thrombin is present in the composition of the present disclosure, the residual water content in the dried composition is preferably less than about 3% water, more preferred less than 2% water, such as less than 1% water.

In one embodiment, the residual water content in the dry composition is about 0.5% or less. Such low residual water content is possible with e.g. industrial freeze-drying apparatuses.

Hydrophilic Compounds

In one embodiment, the paste of the present disclosure comprises one or more hydrophilic compounds. Hydrophilic compounds usually contain polar or charged functional groups, rendering them soluble in water. Inclusion of one or more hydrophilic compounds in the paste prior to expansion and drying of said paste has a beneficial effect on the wettability of the paste, thus enhancing reconstitution efficiency of the dried paste.

In one embodiment, the hydrophilic compound is a hydrophilic polymer. The hydrophilic polymer may be natural or synthetic, linear or branched, and have any suitable length. Inclusion of a hydrophilic compound in the dry composition enhances the spontaneous reconstitution rate.

In one embodiment, the hydrophilic polymer is selected from the group consisting of Polyethylenimine (PEI), Poly (ethylene glycol) (PEG), Poly(ethylene oxide), Poly(vinyl alcohol) (PVA), Poly(styrenesulfonate) (PSS), Poly(acrylic acid) (PAA), Poly(allylamine hydrochloride) and Poly(vinyl acid). In one embodiment, the hydrophilic compound is PEG.

In one embodiment, the hydrophilic compound is selected from the group consisting of Cetylpyridinium Chloride, Docusate Sodium, Glycine, Hypromellose, Hypromellose, Phthalate, Lechitin, Phospholipids, Poloxamer, Polyoxyethylene Alkyl Ethers, Polyoxyethylene Castor Oil Derivatives, Polyoxyethylene Sorbitan Fatty Acid Esters, Polyoxyethylene Stearates, Polyvinyl Alcohol, Sodium Lauryl Sulfate, Sorbitan Esters (Sorbitan Fatty Acid Esters) and Tricaprylin.

In a preferred embodiment, the hydrophilic compound is a polyol. Thus, according to one embodiment of the invention, one or more polyols may be included in the paste prior to expansion and drying of the paste. Polyols greatly enhance the reconstitution rate of the dry paste composition and play a role in ensuring an optimal consistency of the reconstituted paste.

A polyol as defined herein is a compound with multiple hydroxyl functional groups. Polyols include sugars (mono-, di- and polysaccharides) and sugar alcohols and derivatives thereof.

Monosaccharides include but are not limited to glucose, fructose, galactose, xylose and ribose.

Disaccharides include but are not limited to sucrose (saccharose), lactulose, lactose, maltose, trehalose and cellobiose.

Polysaccharides include but are not limited to starch, glycogen, cellulose and chitin.

A sugar alcohol, also known as a polyalcohol is a hydrogenated form of carbohydrate, whose carbonyl group (aldehyde or ketone, reducing sugar) has been reduced to a primary or secondary hydroxyl group (hence the alcohol). Sugar alcohols have the general formula $H(HCHO)_{n+1}H$, whereas sugars have $H(HCHO)_n HCO$. Some common sugar alcohols which may be used in the method of the present disclosure include but are not limited to: Glycol (2-carbon), Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Dulcitol (6-carbon), Fucitol (6-carbon), Iditol (6-carbon), Inositol (6-carbon; a cyclic sugar alcohol), volemitol (7-carbon), Isomalt (12-carbon), Maltitol (12-carbon), Lactitol (12-carbon), Polyglycitol.

In one embodiment, the dry composition comprises a single hydrophilic compound, such as a single polyol.

In one embodiment of the invention, the dry composition comprises more than one hydrophilic compound, such as two, three, four, five, six or even more different hydrophilic compounds.

In a preferred embodiment, the hydrophilic compound is a polyol.

In one embodiment of the invention, the dry composition comprises two polyols, for example mannitol and glycerol or trehalose and a glycol.

In one embodiment of the invention, the dry composition comprises one or more sugar alcohols, such as one or more sugar alcohols selected from the group consisting of Glycol, Glycerol, Erythritol, Threitol, Arabitol, Xylitol, Ribitol, Mannitol, Sorbitol, Dulcitol, Fucitol, Iditol, Inositol, volemitol, Isomalt, Maltitol, Lactitol, Polyglycitol.

In one embodiment, the dry composition comprises one or more sugar alcohols and one or more sugars, such as one sugar alcohol and one sugar.

In one embodiment, the dry composition comprises one sugar alcohol and optionally one or more additional hydrophilic compounds, such as one or more polyols, which may be either sugar alcohols or sugars.

In one embodiment, the dry composition does not comprise a sugar as the only polyol.

In one embodiment of the invention, the dry composition comprises mannitol.

In one embodiment of the invention, the dry composition comprises sorbitol.

In one embodiment of the invention, the dry composition comprises glycerol.

In one embodiment of the invention, the dry composition comprises trehalose.

In one embodiment of the invention, the dry composition comprises glycol, such as propylene glycol.

In one embodiment of the invention, the dry composition comprises xylitol.

In one embodiment of the invention, the dry composition comprises maltitol.

In one embodiment of the invention, the dry composition comprises sorbitol.

In one embodiment the paste according to the invention prior to drying comprises from about 1% to about 40% of one or more hydrophilic compounds, for example from about 1% to about 30% of one or more hydrophilic compounds, such as from about 1% to about 25% of one or more hydrophilic compounds, for example from about 1% to about 20% of one or more hydrophilic compounds, such as from about 1% to about 15% of one or more hydrophilic compounds, such as from about 1% to about 14% of one or more hydrophilic compounds, for example from about 1% to about 13% of one or more hydrophilic compounds, such as from about 1% to about 12% of one or more hydrophilic compounds, for example from about 1% to about 11% of one or more hydrophilic compounds, such as about 1% to about 10% of one or more hydrophilic compounds.

In one embodiment the paste according to the invention prior to drying comprises from about 2% to about 40% of one or more hydrophilic compounds, for example from about 2% to about 30% of one or more hydrophilic compounds, such as from about 2% to about 25% of one or more hydrophilic compounds, for example from about 2% to about 20% of one or more hydrophilic compounds, such as from about 2% to about 18% of one or more hydrophilic compounds, for example from about 2% to about 17% of one or more hydrophilic compounds, such as from about 2% to about 16% of one or more hydrophilic compounds, for example from about 2% to about 15% of one or more hydrophilic compounds, such as from about 2% to about 14% of one or more hydrophilic compounds, for example from about 2% to about 13% of one or more hydrophilic compounds, such as from about 2% to about 12% of one or more hydrophilic compounds, for example from about 2% to about 11% of one or more hydrophilic compounds, such as about 2% to about 10% of one or more hydrophilic compounds.

In one embodiment the paste according to the invention prior to drying comprises from about 3% to about 40% of one or more polyols, for example from about 3% to about 30% of one or more polyols, such as from about 3% to about 25% of one or more polyols, for example from about 3% to about 20% of one or more polyols, such as from about 3% to about 18% of one or more polyols, for example from about 3% to about 17% of one or more polyols, such as from about 3% to about 16% of one or more polyols, for example from about 3% to about 15% of one or more polyols, such as from about 3% to about 14% of one or more polyols, for example from about 3% to about 13% of one or more polyols, such as from about 3% to about 12% of one or more polyols, for example from about 3% to about 11% of one or more polyols, such as about 3% to about 10% of one or more polyols.

In one embodiment the paste according to the invention prior to drying comprises from about 4% to about 40% of one or more polyols, for example from about 4% to about 30% of one or more polyols, such as from about 4% to about 25% of one or more polyols, for example from about 4% to about 20% of one or more polyols, such as from about 4% to about 18% of one or more polyols, for example from about 4% to about 17% of one or more polyols, such as from about 4% to about 16% of one or more polyols, for example from about 4% to about 15% of one or more polyols, such as from about 4% to about 14% of one or more polyols, for example from about 4% to about 13% of one or more polyols, such as from about 4% to about 12% of one or more polyols, for example from about 4% to about 11% of one or more polyols, such as about 4% to about 10% of one or more polyols.

In one embodiment, the paste according to the invention prior to drying comprises more than about 5% of one or more hydrophilic compounds, hence in one embodiment the paste according to the invention prior to drying comprises from about 5% to about 40% of one or more hydrophilic compounds, for example from about 5% to about 30% of one or more hydrophilic compounds, such as from about 5% to about 25% of one or more hydrophilic compounds, for example from about 5% to about 20% of one or more hydrophilic compounds, such as from about 5% to about 18% of one or more hydrophilic compounds, for example from about 5% to about 17% of one or more hydrophilic compounds, such as from about 5% to about 16% of one or more hydrophilic compounds, for example from about 5% to about 15% of one or more hydrophilic compounds, such as from about 5% to about 14% of one or more hydrophilic compounds, for example from about 5% to about 13% of one or more hydrophilic compounds, such as from about 5% to about 12% of one or more hydrophilic compounds, for example from about 5% to about 11% of one or more hydrophilic compounds, such as about 5% to about 10% of one or more hydrophilic compounds.

In one embodiment the paste according to the invention prior to drying comprises from about 6% to about 40% of one or more hydrophilic compounds, for example from about 6% to about 30% of one or more hydrophilic compounds, such as from about 6% to about 25% of one or more hydrophilic compounds, for example from about 6% to about 20% of one or more hydrophilic compounds, such as from about 6% to about 18% of one or more hydrophilic compounds, for example from about 6% to about 17% of one or more hydrophilic compounds, such as from about 6% to about 16% of one or more hydrophilic compounds, for example from about 6% to about 15% of one or more hydrophilic compounds, such as from about 6% to about 14% of one or more hydrophilic compounds, for example from about 6% to about 13% of one or more hydrophilic compounds, such as from about 6% to about 12% of one or more hydrophilic compounds, for example from about 6% to about 11% of one or more hydrophilic compounds, such as about 6% to about 10% of one or more hydrophilic compounds.

In one embodiment the paste according to the invention prior to drying comprises from about 10% to about 40% of one or more hydrophilic compounds, for example from about 10% to about 30% of one or more hydrophilic compounds, such as from about 10% to about 25% of one or more hydrophilic compounds, for example from about 10% to about 20% of one or more hydrophilic compounds, such as from about 10% to about 18% of one or more hydrophilic compounds, for example from about 10% to about 17% of one or more hydrophilic compounds, such as from about 10% to about 16% of one or more hydrophilic compounds, for example from about 10% to about 15% of one or more hydrophilic compounds.

In one embodiment, the paste according to the invention prior to drying comprises more than about 1% of one or more hydrophilic compounds, such as more than about 2% of one or more hydrophilic compounds, for example more than about 3% of one or more hydrophilic compounds, such as more than about 4% of one or more hydrophilic compounds, for example more than about 5% of one or more hydrophilic compounds, such as more than about 6% of one or more hydrophilic compounds, for example more than about 7% of one or more hydrophilic compounds, such as more than about 8% of one or more hydrophilic compounds, for example more than about 9% of one or more hydrophilic compounds, such as more than about 10% of one or more hydrophilic compounds.

In one embodiment, the paste according to the invention prior to drying comprises less than about 20% of one or more hydrophilic compounds, such as less than about 18% of one or more hydrophilic compounds, for example less than about 17% of one or more hydrophilic compounds, such as less than about 16% of one or more hydrophilic compounds, for example less than about 15% of one or more hydrophilic compounds, such as less than about 14% of one or more hydrophilic compounds, for example less than about 13% of one or more hydrophilic compounds, such as less than about 12% of one or more hydrophilic compounds, for example less than about 11% of one or more hydrophilic compounds, such as less than about 10% of one or more hydrophilic compounds.

After drying, the dry composition comprises from about 10% to about 60% of one or more hydrophilic compounds, such as from about 10% to about 50% of one or more hydrophilic compounds, for example from about 10% to about 50%, such as from about 10% to about 45% of one or more hydrophilic compounds, for example from about 10% to about 40%, such as from about 10% to about 35% of one or more hydrophilic compounds, for example from about 10% to about 30% of one or more hydrophilic compounds.

In one embodiment, the dry composition comprises from about 15% to about 60% of one or more hydrophilic compounds, such as from about 15% to about 50% of one or more hydrophilic compounds, for example from about 15% to about 50%, such as from about 15% to about 45% of one or more hydrophilic compounds, for example from about 15% to about 40%, such as from about 15% to about 35% of one or more hydrophilic compounds, for example from about 15% to about 30% of one or more hydrophilic compounds.

In one embodiment, the dry composition comprises from about 20% to about 60% of one or more hydrophilic compounds, such as from about 20% to about 50% of one or more hydrophilic compounds, for example from about 20% to about 50%, such as from about 20% to about 45% of one or more hydrophilic compounds, for example from about 20% to about 40%, such as from about 20% to about 30% of one or more hydrophilic compounds.

In one embodiment, the dry composition comprises from about 25% to about 60% of one or more hydrophilic compounds, such as from about 25% to about 50% of one or more hydrophilic compounds, for example from about 25% to about 45% of one or more hydrophilic compounds, such as from about 25% to about 40% of one or more hydrophilic compounds, for example from about 25% to about 35% of one or more hydrophilic compounds, such as from about 25% to about 30% of one or more hydrophilic compounds.

In one embodiment, the dry composition comprises from about 27% to about 60% of one or more hydrophilic compounds, such as from about 27% to about 50% of one or more hydrophilic compounds, for example from about 27% to about 45% of one or more hydrophilic compounds, such as from about 27% to about 40% of one or more hydrophilic compounds, for example from about 27% to about 35% of one or more hydrophilic compounds, such as from about 27% to about 30% of one or more hydrophilic compounds.

In one embodiment, the dry composition comprises from about 30% to about 60% of one or more hydrophilic compounds, such as from about 30% to about 50% of one or more hydrophilic compounds, for example from about 30% to about 45% of one or more hydrophilic compounds, such as from about 30% to about 40% of one or more hydrophilic compounds, for example from about 30% to about 35% of one or more hydrophilic compounds.

In one embodiment, the dry composition comprises less hydrophilic compounds than biocompatible polymer, i.e. the hydrophilic compounds:biocompatible polymer ratio is less than 1:1, such as less than or about 0.9:1, for example less than or about 0.8:1, such as less than or about 0.7:1, for example less than or about 0.6:1, such as less than or about 0.5:1, such as less than or about 0.4:1, for example less than or about 0.3:1, such as less than or about 0.2:1, for example less than or about 0.1:1. The hydrophilic compounds:biocompatible polymer ratio is the same in the paste prior to drying.

In one embodiment, the hydrophilic compounds:biocompatible polymer ratio is between about 0.1:1 and 1:1; such as between about 0.2:1 and 1:1, for example between about 0.3:1 and 1:1, such as between about 0.4:1 and 1:1. In one embodiment, the hydrophilic compounds:biocompatible polymer ratio is between about 0.1:1 and 0.8:1; such as between about 0.1:1 and 0.7:1, for example between about 0.1:1 and 0.6:1, such as between about 0.1:1 and 0.5:1, for example between 0.1:1 and 0.45:1. Even more preferred, the hydrophilic compounds:biocompatible polymer ratio is between about 0.15:1 and 0.8:1; such as between about 0.15:1 and 0.7:1, for example between about 0.15:1 and 0.6:1, such as between about 0.15:1 and 0.5:1, for example between about 0.15:1 and 0.5:1, such as between 0.15:1 and 0.45:1. In a preferred embodiment, the hydrophilic compounds:biocompatible polymer ratio is between about 0.2:1 and 0.8:1; such as between about 0.2:1 and 0.7:1, for example between about 0.2:1 and 0.6:1, such as between about 0.2:1 and 0.5:1, for example 0.2:1 and 0.45:1.

In one embodiment, the hydrophilic compounds:biocompatible polymer ratio is between about 0.3:1 and 0.8:1; such as between about 0.3:1 and 0.7:1, for example between about 0.3:1 and 0.6:1, such as between about 0.3:1 and 0.5:1, for example between about 0.35:1 and 0.5:1, such as between about 0.35:1 and 0.45:1.

In one embodiment the hydrophilic compound of the present disclosure is not polyethylene glycol (PEG).

Further Compounds

The dry composition of the invention may further comprise one or more of the following: DMSO (dimethyl sulfoxide), 2-Methyl-2,4-pentanediol (MPD) and/or one or more of the compounds mentioned in the table below.

| Bulking agent | Buffering agent | Solubilising agent | Miscellaneous |
| --- | --- | --- | --- |
| Sugars/Sugar alcohols: | Citric acid | Complexing agent: | Tonicifying agent: |
| Mannitol | Sodium citrate | Ethylediamine tetra acetic | Sodium chloride |
| Lactose | Potassium citrate | acid (EDTA) | Sucrose |
| Sucrose | Tartaric acid | Alpha cyclodextrin | Mannitol |
| Trehalose | Sodium phosphate | Hydroxypropyl-β-cyclodextrin (HP-β-CD) | Dextrose |
| Sorbitol | Tris base | | |
| Glucose | Tris HCl | | |
| Raffinose | Tris acetate | | |
| | Zinc chloride | | |
| | Sodium acetate | | |
| | Potassium acetate | | |
| | Arginine | | |

-continued

| Bulking agent | Buffering agent | Solubilising agent | Miscellaneous |
| --- | --- | --- | --- |
| Amino acids:<br>Arginine<br>Glycine<br>Histidine | pH adjusting agent:<br>Hydrochloric acid<br>Sodium hydroxide<br>Meglumine | Surfactants:<br>polysorbate 80 | Antimicrobial agents:<br>Benzalkonium chloride<br>benzyl alcohol<br>phenol<br>m-cresol<br>methyl paraben<br>ethyl paraben |
| Polymer:<br>Dextran<br>Polyethylene glycol | | Co-solvents:<br>Tert-butyl alcohol<br>Iso-propyl alcohol<br>Dichloromethane<br>Ethanol<br>Acetone<br>Glycerol | Collapse temperature modifier:<br>Dextran<br>Hydroxyethyl starch<br>Ficoll<br>gelatin |

In one embodiment, the dry composition of the present disclosure comprises one or more antimicrobial agents, such as one or more antibacterial agents.

In one embodiment, the dry composition of the present disclosure comprises benzalkonium chloride.

In one embodiment, the dry composition of the present disclosure does not comprise an antimicrobial agent.

In one embodiment, the dry composition further comprises an extrusion enhancer, i.e. a compound capable of facilitating extrusion of a paste from a syringe.

It has previously been shown that the provision of certain extrusion enhancers, such as albumin in an appropriate amount, enables the use of higher gelatine concentrations as it decreases the amount of force needed to extrude the gelatine paste composition from e.g. a syringe. The use of higher gelatine concentrations may in turn improve the haemostatic properties of such products. It is necessary to provide the extrusion enhancers in appropriate amounts. The amounts are preferably high enough so as to obtain the extrusion effect, i.e. to enable a flowable paste even for relatively high amounts of the biocompatible polymer, e.g. cross-linked gelatine, so that the haemostatic paste composition can be accurately applied by a surgeon using e.g. a syringe comprising an applicator tip; on the other hand, the amounts shall be as low as to prevent negative functional properties of the haemostatic composition.

The extrusion enhancer is preferably albumin, especially human serum albumin.

In the paste composition of the present invention before vacuum expansion and drying, the extrusion enhancer, such as albumin, is preferably present in an amount of between about 0.1% to about 10%, such as between about 0.2% to about 8%, for example between about 0.3% to about 7%, preferably between about 0.5% to about 5%, more preferred between about 1% to about 4%.

In the dry paste composition of the present invention, the extrusion enhancer, such as albumin, is preferably present in an amount of between about 0.3% to about 30%, such as between about 0.5% to about 25%, for example between about 1% to about 20%, preferably between about 2% to about 15%.

In one embodiment, the extrusion enhancer is not present in the dry composition, but is instead introduced into the paste composition during reconstitution. For example the extrusion enhancer may be present in the aqueous medium used for reconstitution of the paste, thereby obtaining a wet paste composition comprising the extrusion enhancer.

In one embodiment, the reconstituted wet paste compositions according to the present invention have a mean extrusion force (e.g. by employing the test method described in example 1 of WO 2013/060770) of 40 N or below, preferably below 35 N, especially preferred below 30 N or even below 20 N.

Another class of extrusion enhancers according to the present invention are phospholipids, such as phosphatidylcholine and -serine, or complex mixtures such as lecithins or soy bean oils.

Bioactive Agent

In one embodiment of the invention, the dry composition comprises one or more bioactive agents, i.e. one or more bioactive agents are included in the paste prior to expansion and drying. It is essential that the bioactive agent retains its bioactivity throughout the process, i.e. that the agent has retained its biological function in the final reconstituted paste. Many bioactive agents are unstable in solution, particularly enzymes and other proteins that may be degraded or lose their secondary structure when water is present.

In one embodiment the bioactive agent stimulates wound healing and/or haemostasis, such as thrombin.

Conventionally, a thrombin solution is mixed with a dry or pre-wetted gelatine powder to make a haemostatic paste directly at the surgical site at the time of need of the haemostatic paste, e.g. by using commercially available haemostatic kits such as Floseal and Surgiflo. The thrombin solution must be made just prior to making the paste as thrombin in solution is very unstable and will self-degrade rapidly. The making of a thrombin solution at the surgical site is time consuming and involves a risk of making mistakes regarding the correct dilution of thrombin.

The present disclosure allows for the addition of thrombin to the paste prior to drying, thereby resulting in a dry haemostatic composition comprising thrombin, which upon reconstitution with a suitable aqueous medium, such as water, will comprise a desired amount of thrombin without the need for time-consuming and error-prone thrombin dilution steps and addition at the surgical site. That thrombin may be included in the dry composition of the present disclosure thus constitutes a clear advantage over conventional methods for making haemostatic pastes.

The present inventors have shown that thrombin may be included in a paste and dried by freeze-drying according to the present disclosure with essentially no loss of thrombin activity measured in the reconstituted paste.

Thrombin may be added to the paste of the present disclosure prior to drying in an amount sufficient to ensure effective haemostasis of the reconstituted dry composition.

In one embodiment thrombin is added at a concentration in the range of about 100 IU/ml paste to about 500 IU/ml paste, such as about 150 IU/ml paste to about 450 IU/ml paste, for example about 200 IU/ml paste to about 400 IU/ml paste, such as about 250 IU/ml paste to about 350 IU/ml paste.

In one embodiment, thrombin is added to the paste prior to drying at a concentration in the range of about 50 IU/g paste to about 5000 IU/g paste, preferably between about 100 IU/g paste to about 1000 IU/g paste, such as between about 200 IU/g paste to about 800 IU/g paste. In such embodiments, the dry composition will comprise thrombin. In another embodiment, the dry composition does not comprise thrombin and thrombin may be added upon reconstitution of the dry composition by reconstituting the dry paste composition with a liquid comprising thrombin.

The one or more bioactive agents can be e.g. thrombin or thrombin in combination with fibrinogen, or thrombin and fibrinogen in combination with Factor XIII, or thrombin and fibrinogen and Factor XIII in combination with tranexamic acid.

Thrombin is a "trypsin-like" serine protease protein that in humans is encoded by the F2 gene. Prothrombin (coagulation factor II) is proteolytically cleaved to form thrombin in the coagulation cascade, which ultimately results in the stemming of blood loss. Thrombin in turn acts as a serine protease that converts soluble fibrinogen into insoluble strands of fibrin, as well as catalyzing many other coagulation-related reactions. In the blood coagulation pathway, thrombin acts to convert factor XI to XIa, VIII to VIIIa, V to Va, and fibrinogen to fibrin.

A preferred bioactive agent according to the invention is thrombin. In one embodiment, the thrombin is added as prothrombin.

In one embodiment, the dry composition comprises one or more bioactive agents that stimulate bone and/or tendon and/or tissue healing such as one or more growth factors selected from the group consisting of matrix metalloproteinases (MMPs), insulin-like growth factor 1 (IGF-I), platelet-derived growth factor (PDGF), vascular endothelial growth factor (VEGF), basic fibroblast growth factor (bFGF) and transforming growth factor beta (TGF-β).

In one embodiment, the dry composition comprises one or more Bone Morphogenetic Proteins (BMPs). Bone morphogenetic proteins (BMPs) are a subgroup of the TGF-β superfamily. Bone Morphogenetic Proteins (BMPs) are a group of growth factors also known as cytokines and as metabologens. Originally discovered by their ability to induce the formation of bone and cartilage, BMPs are now considered to constitute a group of pivotal morphogenetic signals, orchestrating tissue architecture throughout the body.

In one embodiment, the dry composition of the present disclosure comprises one or more matrix metalloproteinases (MMPs). MMPs are zinc-dependent endopeptidases. MMPs have a very important role in the degradation and remodeling of the extracellular matrix (ECM) during the healing process after an injury. Certain MMPs including MMP-1, MMP-2, MMP-8, MMP-13, and MMP-14 have collagenase activity, meaning that, unlike many other enzymes, they are capable of degrading collagen I fibrils.

These growth factors all have different roles during the healing process. IGF-1 increases collagen and proteoglycan production during the first stage of inflammation, and PDGF is also present during the early stages after injury and promotes the synthesis of other growth factors along with the synthesis of DNA and the proliferation of cells. The three isoforms of TGF-β (TGF-β1, TGF-β2, TGF-β3) are known to play a role in wound healing and scar formation. VEGF is well known to promote angiogenesis and to induce endothelial cell proliferation and migration.

In one embodiment, the dry composition of the present disclosure comprises flakes or particles of extracellular matrix (ECM). ECM is the extracellular part of animal tissue that usually provides structural support to the animal cells in addition to performing various other important functions. ECM has been shown to have very beneficial effect in healing as it facilitates functional tissue regeneration.

The variety of biological agents that can be used in conjunction with the paste of the invention is vast. In general, biological agents which may be administered via haemostatic compositions of the invention include, without limitation, antiinfectives, such as antibiotics and antiviral agents; analgesics and analgesic combinations; antihelmintics; antiarthritics; anticonvulsants; antidepressants; antihistamines; antiinflammatory agents; antimigraine preparations; antineoplastics; antiparkinsonism drugs; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; hormones, such as estradiol and other steroids, including corticosteroids; immunosuppressives; muscle relaxants; parasympatholytics; psychostimulants; naturally derived or genetically engineered proteins, polysaccharides, glycoproteins, or lipoproteins; oligonucleotides, antibodies, antigens, cholinergics, chemotherapeutics, radioactive agents, osteoinductive agents, cystostatics heparin neutralizers, procoagulants and haemostatic agents, such as prothrombin, thrombin, fibrinogen, fibrin, fibronectin, heparinase, Factor X/Xa, Factor VII/VIIa, Factor VIII/VIIIa, Factor IX/IXa, Factor XI/XIa, Factor XII/XIIa, Factor XIII/XIIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents and synthetic peptides having haemostatic activity.

Making the Paste

According to the method of the invention, the agent in powder form, for example a biocompatible polymer, and optionally one or more hydrophilic compounds are mixed with a suitable amount of an aqueous medium to obtain a paste. The mixing may be performed in any suitable way known to a person of skill, e.g. by mixing the contents manually or by using an electrical mixing apparatus, such as a hand mixer, a kitchen mixer or an industrial mixer.

The powder particles are usually substantially insoluble in the aqueous medium allowing for a paste to form. Cross-linking generally renders biocompatible polymers, such as gelatine, insoluble in water.

Mixing of the paste in the mixing vessel introduces a discontinuous gas phase substantially homogenously dispersed through the paste, i.e. the mixed paste will have pores or compartments comprising an expandable gas, such as air.

In one embodiment, the paste is made by mixing an aqueous medium, a gas and an amount of powder particles in a mixing vessel under conditions resulting in the formation of a paste having a discontinuous gas phase substantially homogenously dispersed through the paste. The gas may for example be air, nitrogen, carbon dioxide, xenon, argon or mixtures thereof.

In a particular embodiment, the paste is prepared by the following steps:
- introducing a volume of a liquid into a mixing vessel equipped with a means for mixing said liquid,
- introducing a volume of a gas into said volume of liquid while said means for mixing is operating under conditions effective to mix said liquid and said gas together to form a foam comprising a discontinuous gas phase comprising said gas dispersed in a continuous liquid phase comprising said liquid,
- introducing into said foam an amount of powder particles of a biocompatible polymer suitable for use in hemostasis and which is substantially insoluble in said liquid; and
- mixing said foam and said powder particles together under conditions effective to form a substantially homogenous paste composition comprising said discontinuous gas phase and said particles substantially homogenously dispersed throughout said liquid phase, thereby forming said flowable paste composition.

In one embodiment, the substantially homogenous paste composition comprises a continuous liquid phase, i.e. a liquid phase which is released when applying force to the paste when the paste is contained in an enclosed space.

In one embodiment, the powder particles comprise pores and channels of a size sufficient to hold water by capillary forces. When a paste is made using such particles, water can be released from the paste upon application of force to the paste when the paste is contained in a confined space.

The obtained paste is then transferred into a container suitable for vacuum expansion, freezing and drying of the paste. Preferably, the container into which the paste is transferred is also suitable for reconstituting and applying the reconstituted paste composition, e.g. to a site requiring hemostasis.

The mixing of the paste can generally be performed at room temperature (20-25° C.). However, if thrombin or other sensitive agents, such as other enzymes are included in the paste, it is advisable to perform the mixing of the paste at chilled temperatures and/or within a short time period to avoid or decrease the proteolytic activity of thrombin, as it is well-known that thrombin is liable to self-degradation when wet. Hence, when thrombin or other sensitive bioactive agents are to be included in the paste, the mixing of the paste is usually performed at temperatures below room temperature, such as at about 2° C. to about 25° C., for example at about 2° C. to about 15° C., such as about 2° C. to about 10° C., preferably at about 4° C.

Another or an additional way of preserving the thrombin bioactivity in the paste is to keep the time that thrombin is in a wet state, i.e. the mixing time, at a minimum. Hence, when thrombin or other proteolytic enzymes are to be included in the paste, the mixing of the paste is usually performed within about 5 minutes to about 10 hours, such as about 5 minutes to about 5 hours, for example about 5 minutes to about 2 hours, preferably about 5 minutes to about 1 hour, such as within about 5 minutes to about 30 minutes.

The inventor of the present application has found that it is not essential to perform the mixing of the paste at low temperatures to avoid loss of thrombin activity as no detectable decrease in thrombin activity was discovered when mixing of the paste was performed at ambient temperatures.
Containers Any suitable container known to a person of skill may be used for preparing the paste and holding the paste of the present disclosure while drying, such as vials, jars, tubes, trays, cartridges or syringes.

In one embodiment, the paste is prepared in one container in bulk and transferred/aliquoted into another container for expansion, freezing and drying, wherein said other container is selected from an applicator, such as a syringe, a vial, a jar, a tube, a tray and a cartridge. Preferably, the other container is a medical delivery device suitable for dispensing flowable haemostatic compositions to a patient in need thereof. In one embodiment the container holding the paste composition during expansion, freezing and drying is a syringe.

A "jar" according to the invention is a rigid, approximately cylindrical container with a wide mouth opening. Jars may comprise a re-closable closure unit/lid applied to the mouth of the jar.

The containers may be made from any suitable material such as plastic, glass, ceramic or metal, such as stainless steel.

Examples of suitable plastic materials include but are not limited to polyethylene, polypropylene, polystyrene, polyvinyl chloride, and polytetrafluoroethylene (PTFE).

In one embodiment, the paste is filled into and dried within an applicator suitable for dispensing flowable haemostatic compositions.

In one embodiment, the present disclosure relates to a container comprising:
a. a product chamber comprising a dry composition capable of forming a paste upon addition of an aqueous medium, wherein the pressure within the product chamber is less than the pressure outside the product chamber, and
b. a valve.

Preferably, the dry composition reconstitutes spontaneously upon addition of an aqueous medium to the dry composition being present in the container.

In embodiments where the container does not comprise a bypass, gaseous communication during vacuum expansion and drying occurs through the valve.

The dry composition of the present disclosure may be prepared in various shapes, forms and sizes depending on the shape of the container used. They may be e.g. in the form of plugs, disks, rods, tubes, conical cylinders, spheres, half spheres, tablets, pellets, granules or sheets.
Medical Delivery Device In one embodiment, the paste is filled into and dried within a medical delivery device suitable for dispensing flowable haemostatic compositions, such as a syringe. The transfer takes place before vacuum expansion of the paste.

Figure 5:
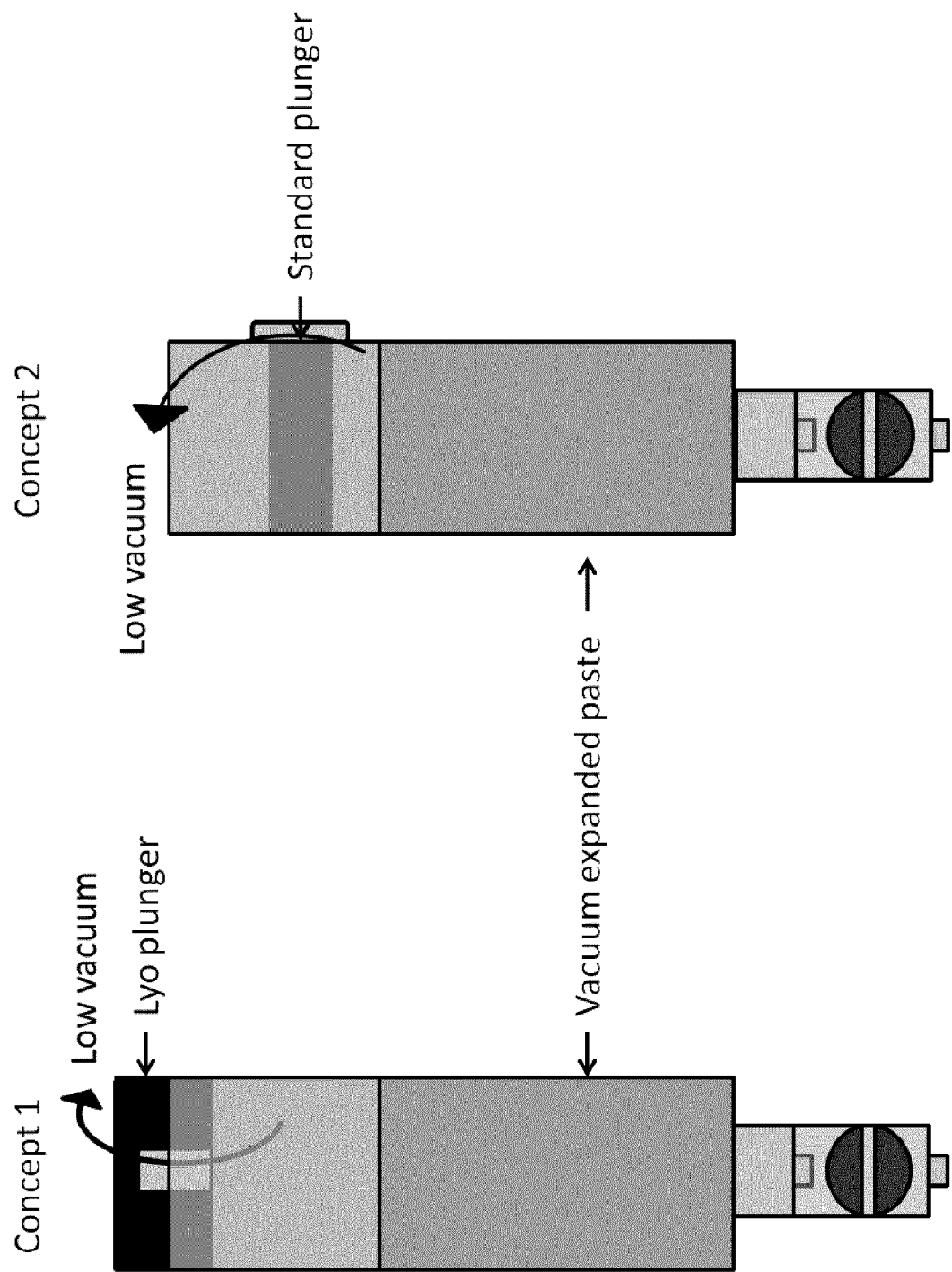
Figure 6:
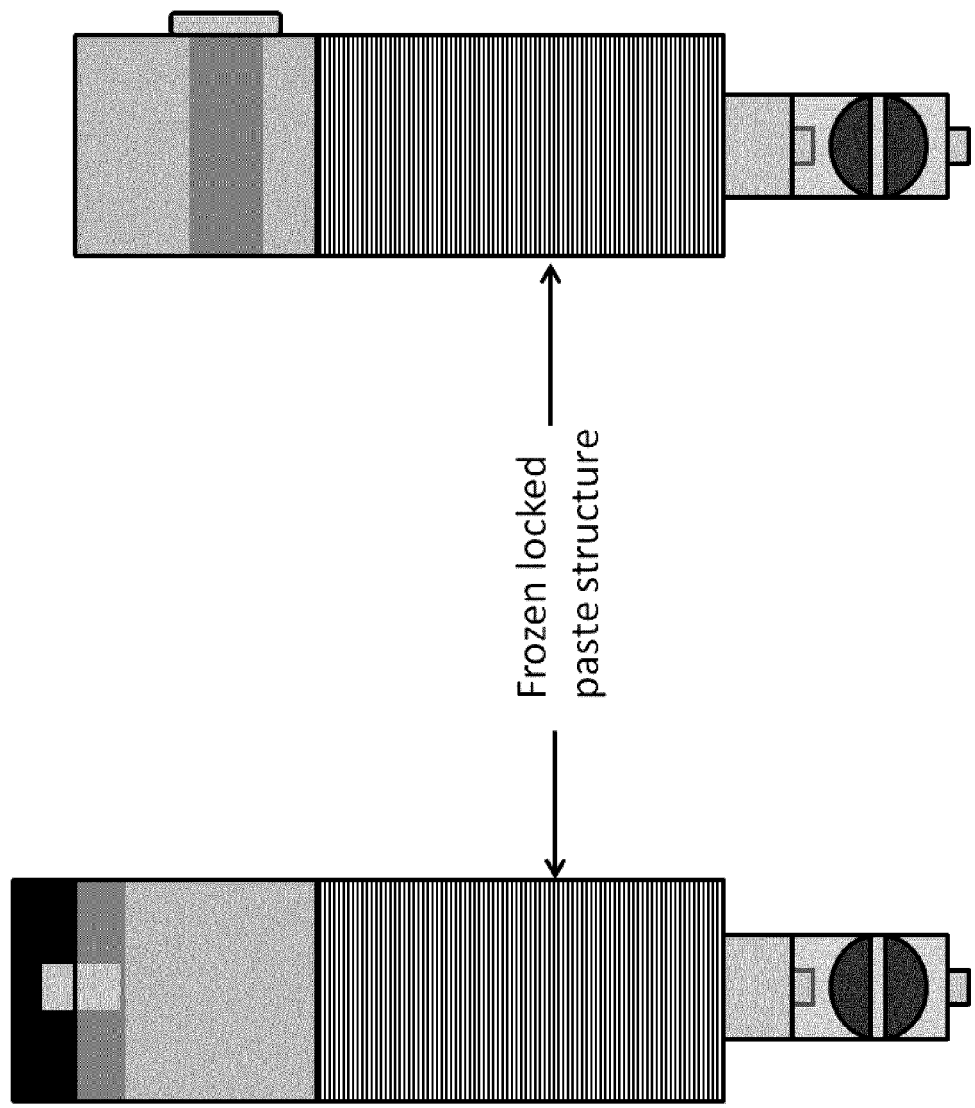
Figure 7:
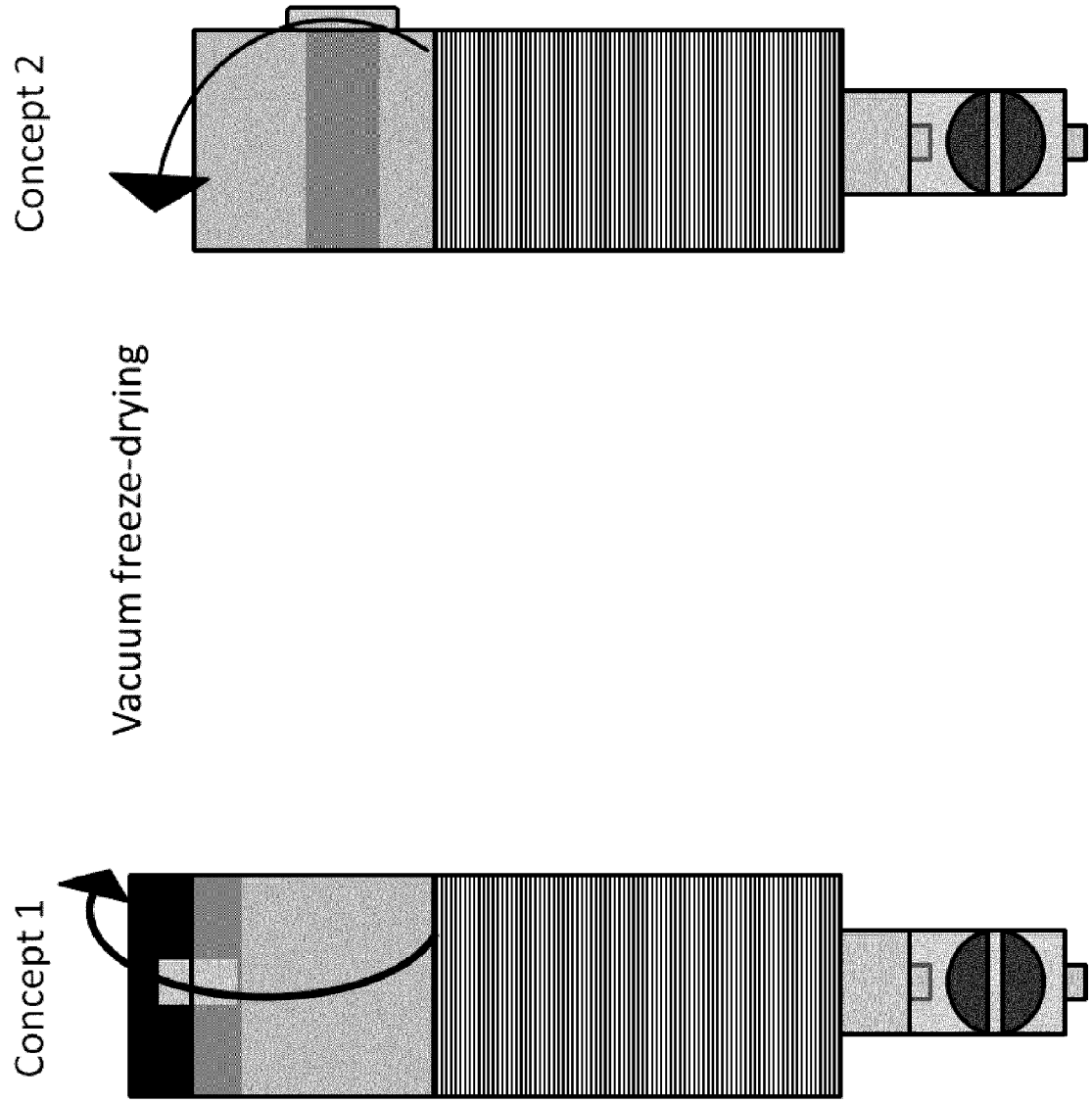
Figure 8:
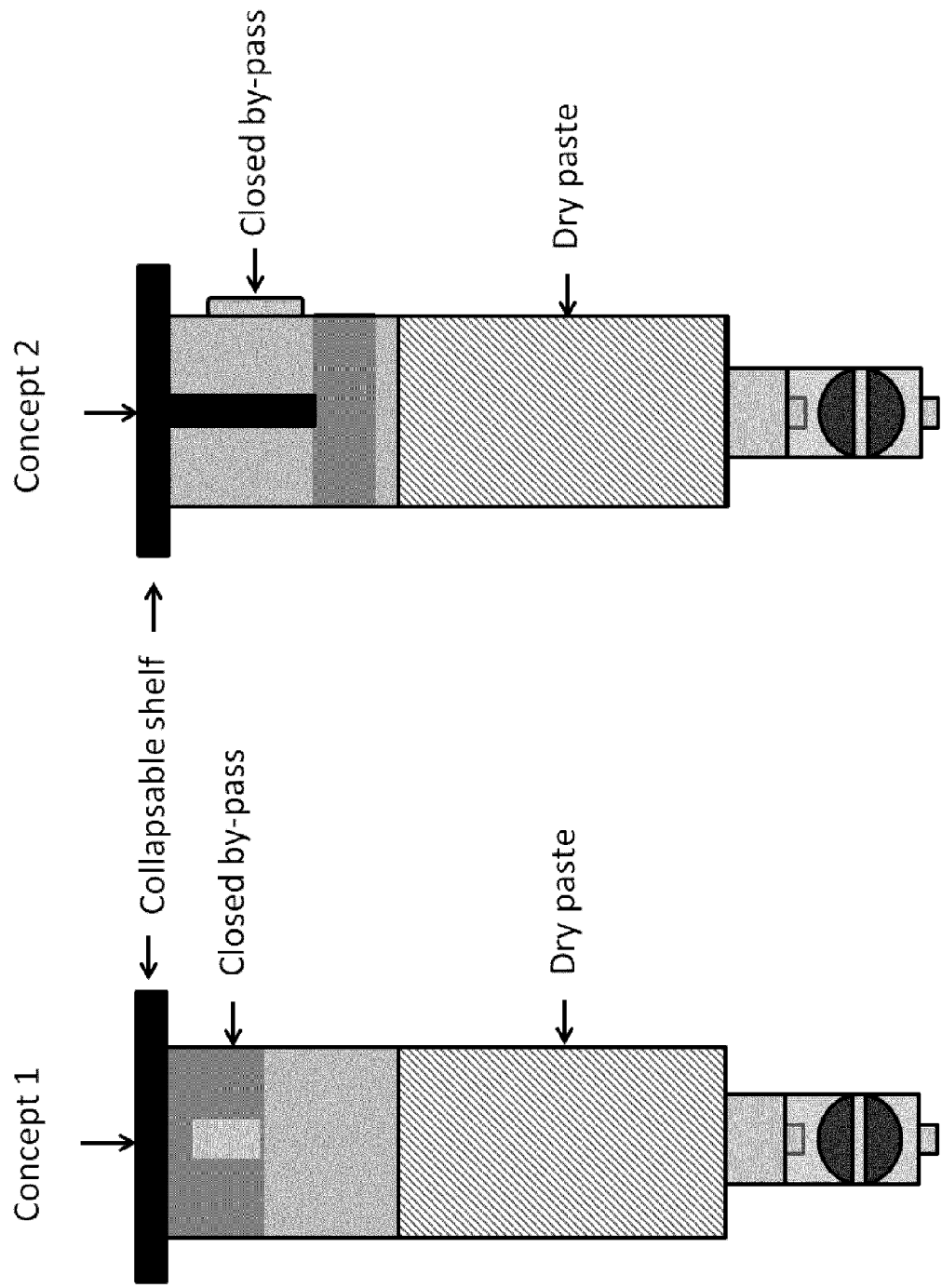
Figure 9:
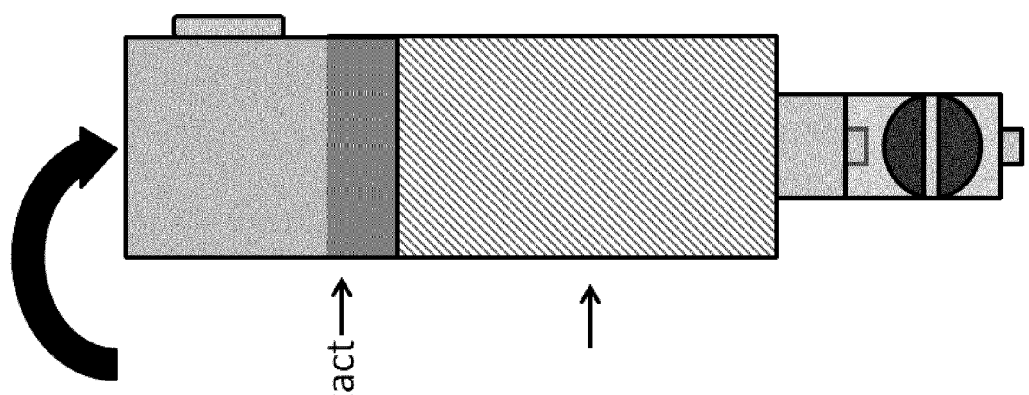
Figure 9:
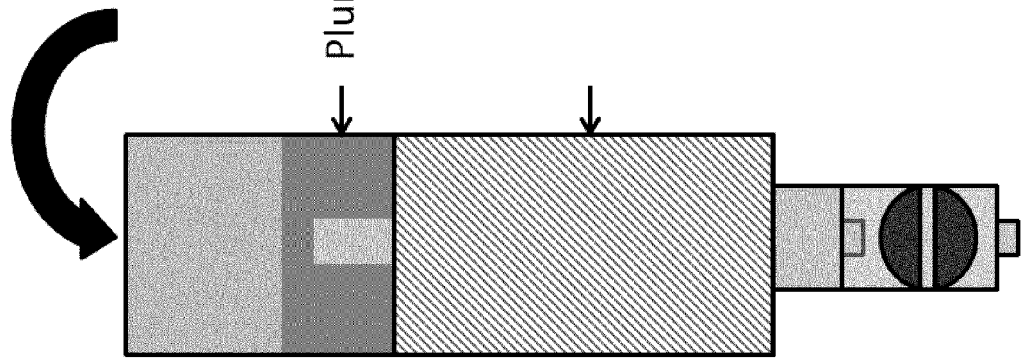
Figure 10:
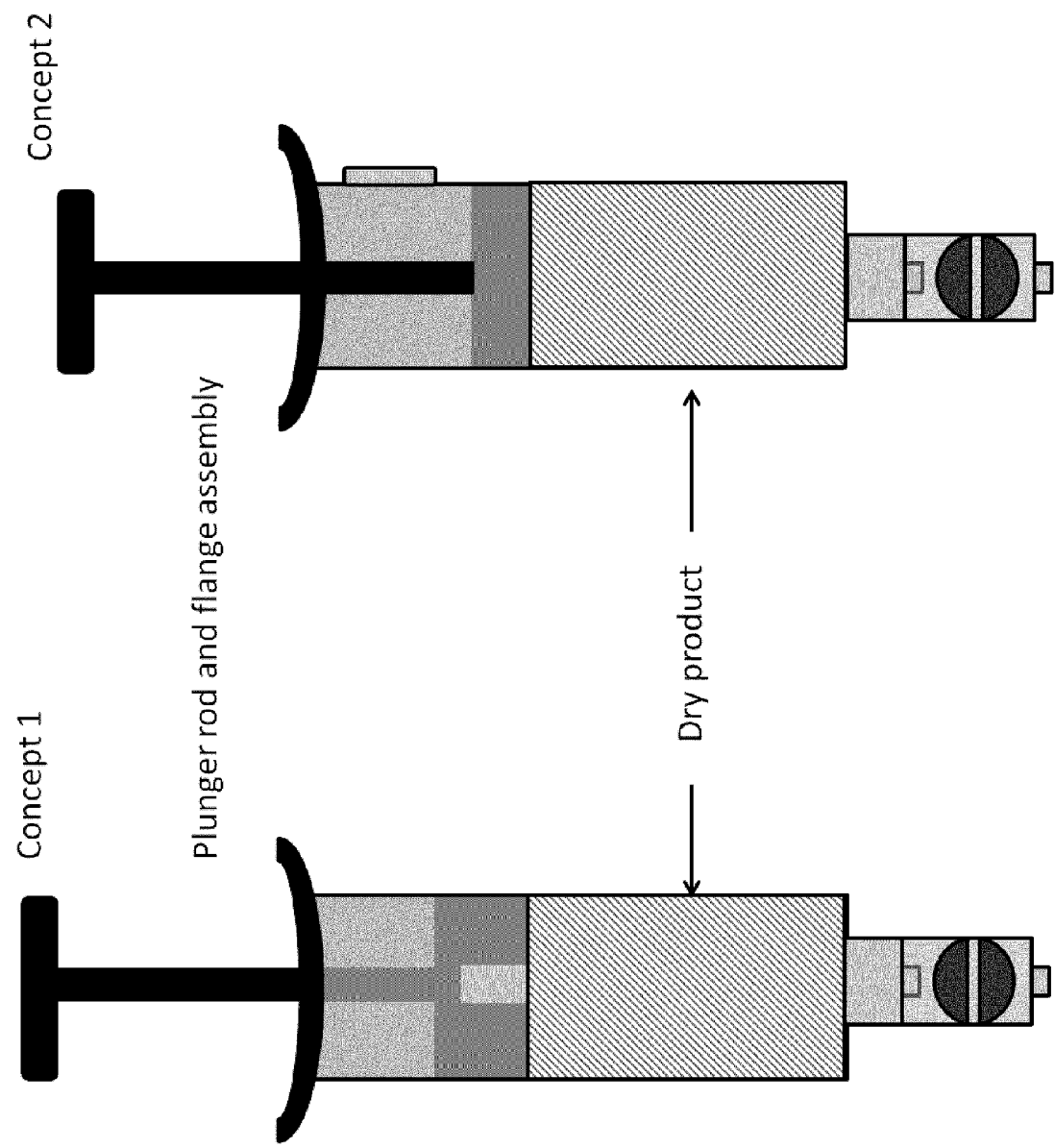
Figure 11:
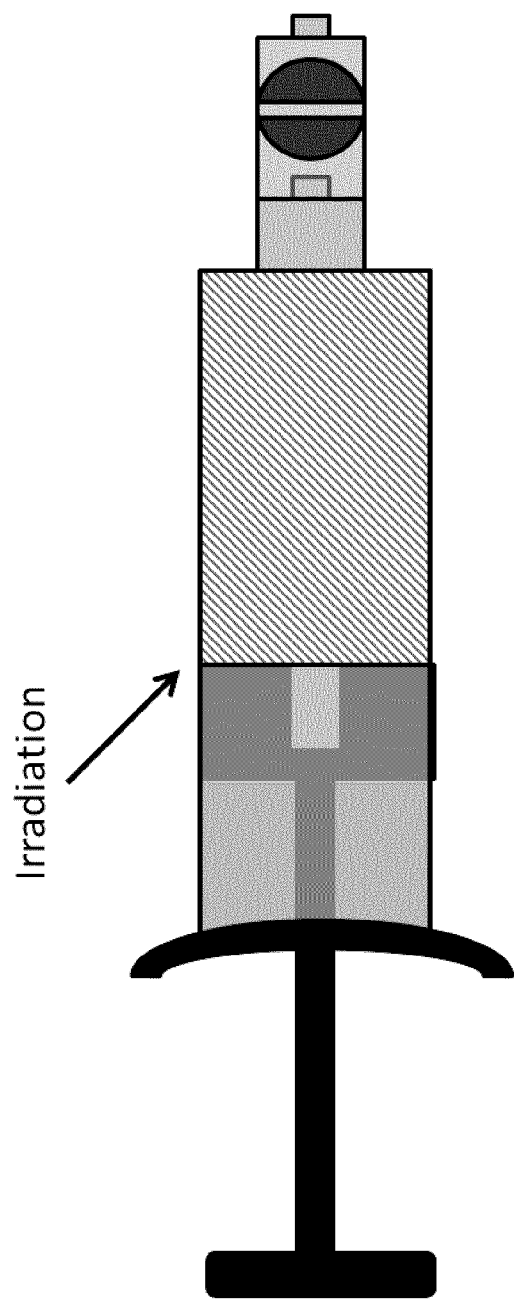

In one embodiment, the medical delivery device is a single-use syringe comprising a valve. In one embodiment, the syringe comprises a lyophilisation bypass channel being a gaseous communication between the product chamber of the syringe and the outside of the container, i.e. the external environment. The bypass may be in an open state allowing for gaseous communication between the product chamber and the outside, and a closed state. The bypass may be located anywhere allowing for gaseous communication between the product chamber and the external environment e.g. in the syringe body or in the plunger as shown in FIG. 5. If the syringe comprises a bypass in the syringe body (FIG. 5, concept 2), the syringe may be fitted with a standard plunger.

One embodiment of the present disclosure relates to a syringe for retaining a freeze-dried paste, such as the presently disclosed dry paste composition, in a vacuum comprising a barrel comprising a vacuum chamber for containing the paste having an open proximal end and a distal end having a first fluid opening, a connector portion having a second fluid opening and adapted for connection to a liquid receptacle, and a pressure chamber connecting the connector portion and the distal end of the vacuum chamber, a pressure valve located in the pressure chamber and adapted to seal the first and/or second fluid openings in a first position and form a fluid passageway between the first and second fluid openings in a second position, a plunger configured to be axially displaced in the vacuum chamber through the open proximal end, and one or more vacuum bypass channels. The syringe is preferably a single-use disposable syringe.

When freeze-drying the paste the vacuum that can be created in the vacuum chamber is important to expand the paste. And by retaining the dry paste in a vacuum in the vacuum chamber of the syringe, i.e. at a pressure level lower than surrounding ambient pressure, addition of liquid upon preparation and use of the paste is eased, because the liquid is sucked into the vacuum chamber due to the reduced pressure in the vacuum chamber.

The barrel may be provided with a flange at the proximal end of the vacuum chamber in order to ease handling of the syringe when operating the plunger. Furthermore, the inside volume of the vacuum chamber and/or the pressure chamber may advantageously be cylindrical.

The connector portion may be a connector portion of a standard type, such as a Luer lock or Luer slip connector, preferably a male Luer lock or Luer slip connector. The connector portion may be provided with a threaded portion for secure connection with matching connector. This threaded portion may be provided at the inside of the connector portion as illustrated in FIGS. 18a, 18b, 20a and 20b.

Figure 18A:
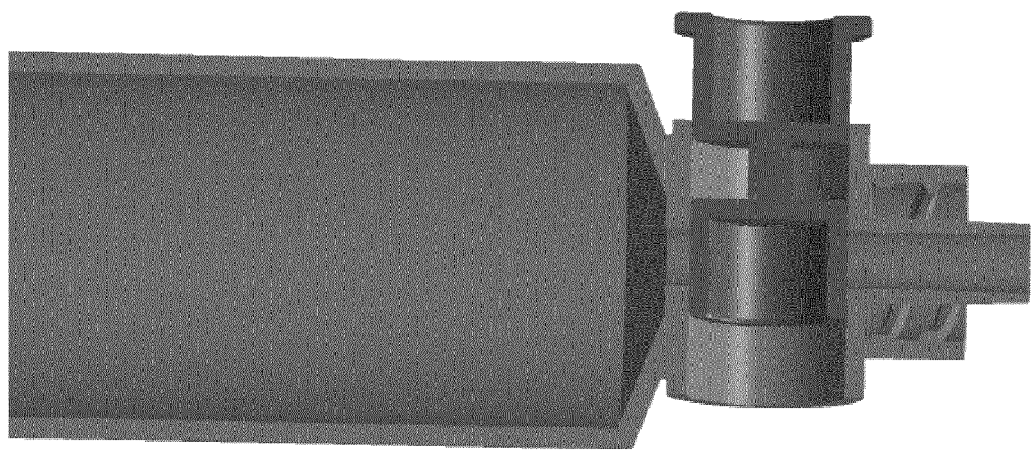
FIGS. 18a-b are cut-through side view illustrations of the barrel of one embodiment of the presently disclosed syringe, with the pressure valve in two different positions.
Figure 18B:
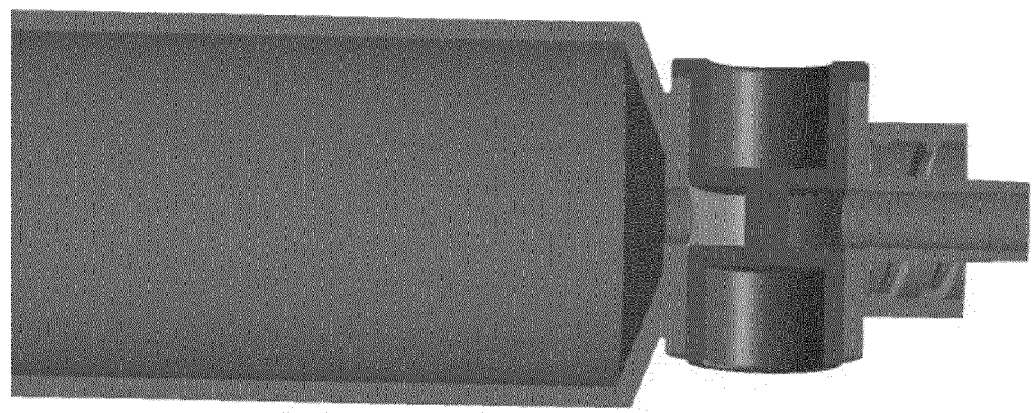

In one embodiment of the presently disclosed syringe the pressure valve comprises a groove. This groove may form the fluid passageway in the second position of the pressure valve. One example is illustrated in FIGS. 18a and 18b. As also illustrated in FIGS. 18a and 18b the pressure valve 5 may comprise two cylindrical sections axially divided by a groove 12, and wherein the void formed by the groove 12 forms the fluid passageway in the second position of the pressure valve 5. In this configuration the pressure valve may be rotation symmetric along the longitudinal axis of the pressure valve as seen from FIG. 18, i.e. the pressure valve may be rotated inside the pressure chamber without interfering with the function of the pressure valve, i.e. in the first position of the pressure valve the vacuum chamber is sealed independent of the rotational position of the pressure valve, and in the second position of the pressure valve a fluid connection is formed between the vacuum chamber and the connector portion independent of the rotational position of the pressure valve.

The pressure valve may be provided in a rubbery material and/or with a rubbery surface to provide for the sealing of the first and second fluid openings in the first position of the pressure valve.

The pressure chamber is preferably located between the vacuum chamber and the second fluid opening. Furthermore, the pressure valve is preferably located in the pressure chamber and adapted to seal the first and second fluid openings in a first position in the pressure chamber and form/create a fluid passageway between the first and second fluid openings in a second position in the pressure chamber, e.g. the pressure valve is preferably located in the pressure chamber, e.g. inside the pressure chamber, in both the first and second positions. I.e. preferably the pressure valve stays inside the pressure chamber during control of the fluid passage between the first and second fluid openings.

In one embodiment of the presently disclosed syringe the pressure chamber comprises a proximal end abutting the distal end of the vacuum chamber and a distal end abutting a proximal end of the connector portion. Further, the connector portion may comprise a proximal end abutting a distal end of the pressure chamber and a distal end adapted for connection to a liquid receptacle. The second fluid opening may form an elongated channel through the connector portion, e.g. as illustrated in FIGS. 18 and 20. As also seen from these figures the second fluid opening may comprise a proximal end abutting a distal end of the pressure chamber and a distal end for inlet and outlet of fluid. Hence, the pressure valve may be adapted to seal a distal end of the first fluid opening and a proximal end of the second fluid opening in said first position.

Thus, with the presently disclosed syringe the liquid for reconstitution of a paste in the vacuum chamber can be provided from the distal end of the syringe, via the second fluid opening in the connector portion and through the pressure chamber and into the vacuum chamber. Delivery of the reconstituted paste is also provided through the distal end of the syringe. This solution is possible because of the provision of the dedicated pressure chamber with the pressure valve located between the vacuum chamber and the distal fluid opening, whereby it may be possible to control the blockage and opening of the fluid passageway between the first and second fluid openings without removing the pressure valve from the pressure chamber and also without access to the second fluid opening. Thus, an external liquid receptacle may be connected to the connector portion of the syringe while the pressure valve is in the first position, i.e. the fluid passageway is blocked (sealed). Switching the pressure valve to the second position opens the fluid passageway and liquid can pass from the liquid receptacle to the vacuum chamber of the syringe for reconstitution of the paste. The presently disclosed syringe is therefore safe, easy and quick to use when reconstituting a dry paste, such as a haemostatic paste.

In a further embodiment of the presently disclosed syringe the first and second positions of the pressure valve are radially displaced with respect to the longitudinal axis of the syringe. Furthermore, the pressure valve may protrude from the pressure chamber in the first position of the pressure valve. And further, the pressure valve may be flush with the pressure chamber in the second position of the pressure valve, e.g. fully incorporated in the pressure chamber. The pressure valve may be provided with a valve flange at an end of the pressure valve protruding from the pressure chamber. This valve flange may protrude from the pressure chamber in said first position, and the valve flange may be flush with the pressure chamber in said second position. The valve flange may then have the function as a stop flange for the pressure valve, i.e. the pressure valve may be configured such that the valve flange abuts the pressure chamber in the second position of the pressure valve.

Figure 12:
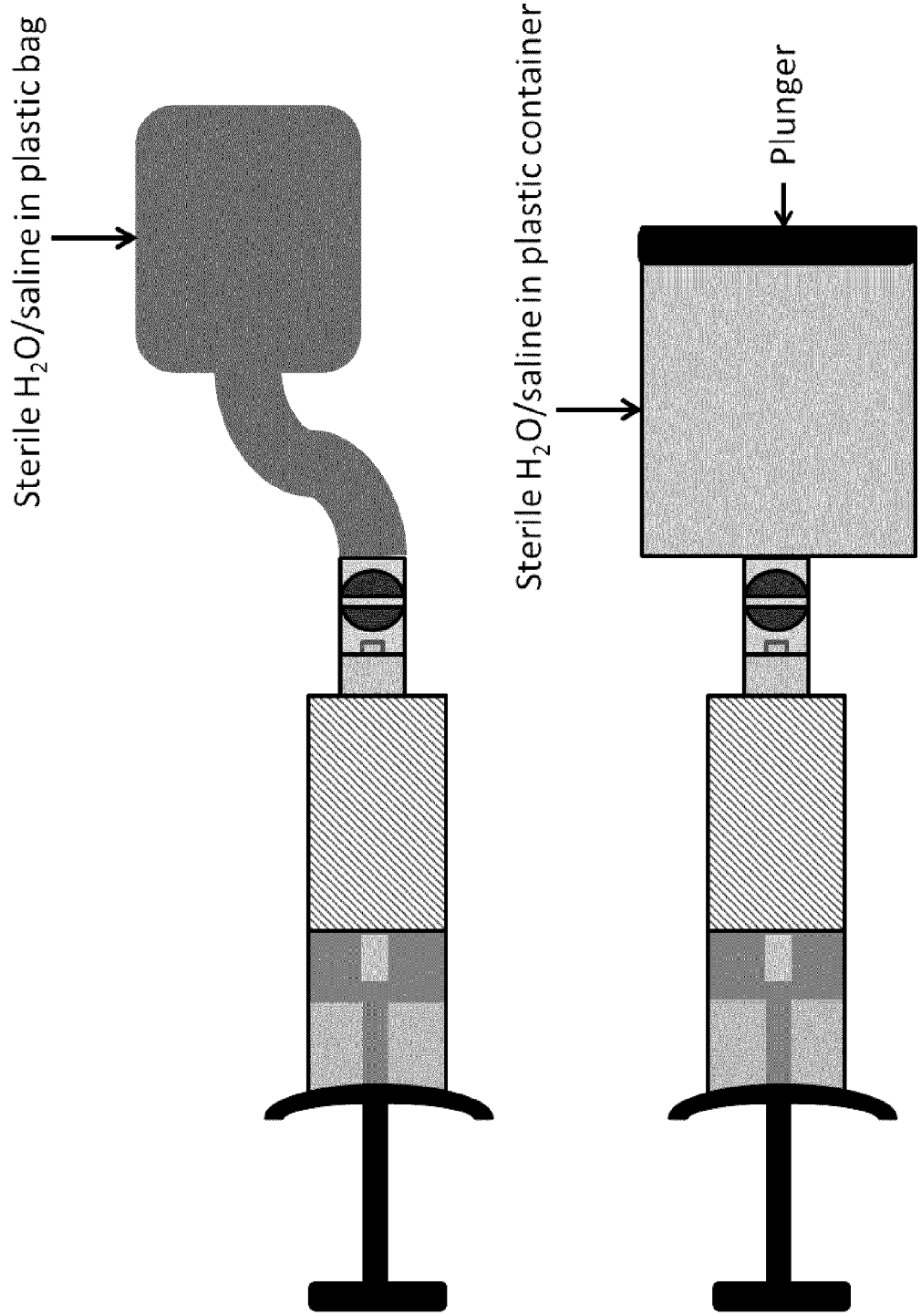
Figure 13:
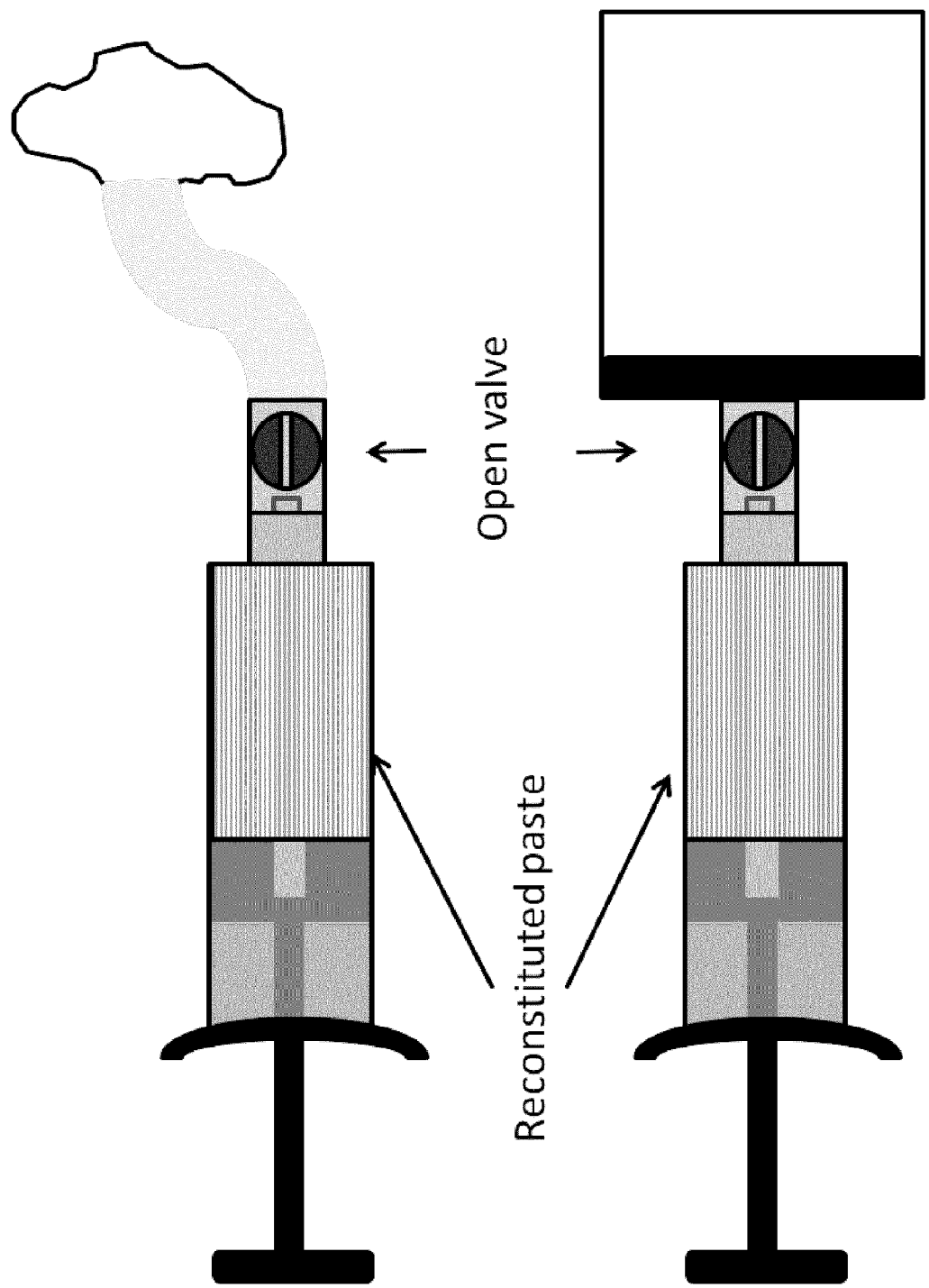

In yet another embodiment of the presently disclosed syringe the first and second positions of the pressure valve are rotatably displaced, e.g. as illustrated in FIGS. 3-13, with the closed position in FIGS. 3-12 and the open position in FIG. 13. As also exemplified in these figures the pressure valve may comprise a through-going channel forming the fluid passageway in the second position of the pressure valve. Furthermore the pressure valve may comprise a cylindrical section with a through-going radial channel forming the fluid passageway in the second position of the pressure valve.

In a further embodiment the pressure valve and the pressure chamber are configured such that the second position of the pressure valve is a locked position. The pressure valve may be axially and/or rotatably locked in this locked position. This may help to ensure that once the pressure valve has been moved to the second position, it stays there, thereby ensuring that paste can be expelled from the syringe when needed. The pressure valve and the pressure chamber may further be configured such the first position is a partly locked position, e.g. the pressure valve cannot be removed from/out of the pressure chamber but can only be moved into the second position. This may help to ensure that the vacuum is retained inside the vacuum chamber.

In a further embodiment of the presently disclosed syringe the pressure valve comprises an aperture, and this aperture preferably forms at least a part of the fluid passageway in the second position of the pressure valve. I.e. preferably this aperture extends transversally through the pressure valve such that the aperture extends in the longitudinal direction of the barrel when inserted in the pressure chamber.

In a further embodiment the pressure valve and the pressure chamber are configured such that the pressure valve is radially limited in said first position, such as radially limited outwards with respect to the longitudinal axis of the barrel. This radial limitation may be provided by means of one or more protrusions on the pressure valve and/or inside the pressure chamber. E.g. the pressure valve comprises one or more protrusions, preferably extending sideways, such as radial to the fluid passageway. The limitation may also be provided by means of a narrowing of an inner side wall of the pressure chamber and this narrowing may be adapted to limit a radial displacement of the pressure valve in the first position, e.g. this narrowing may be adapted to match one or more protrusions of the pressure valve, such that this or these protrusions abuts the narrowing in the first position of the pressure valve. A narrowing may be provided by means of one or more "shoulders" of an inner side wall of the pressure chamber, as exemplary illustrated in FIGS. 19c and 19d.

In a further embodiment the pressure valve protrudes transversely and/or radially from the pressure chamber in said first position and wherein the pressure valve is flush with or totally submerged into the pressure chamber in said second position. The pressure valve may be provided with a top surface, wherein said top surface may be flush with a top surface of the pressure chamber in said first position. These top surfaces may be rounded and/or matched to each other as illustrated in FIGS. 19 and 20.

The pressure valve and the pressure chamber may be configured such that the pressure valve can be inserted from one side of the pressure chamber, such as through only one side of the pressure chamber, e.g. through an opening of the pressure chamber, e.g. a bottom opening of the pressure chamber where a top opening of the pressure chamber may be where through the pressure valve extends when in the first position.

The presently disclosed syringe is preferably configured such that the dry paste composition may be freeze dried inside the vacuum chamber. Said one or more vacuum bypass channels may be configured to provide a fluid, such as a gaseous, communication between the vacuum chamber and the surroundings/the ambient atmosphere, i.e. the vacuum bypass channel(s) may function as the lyophilisation bypass channel as described herein. In one embodiment the syringe is configured such that the plunger sealably engages the vacuum chamber in at least a first axial position of the plunger inside the vacuum chamber, and such that fluid communication is established across the plunger in at least a second axial position of the plunger inside the vacuum chamber via said one or more vacuum bypass channels. I.e. a vacuum can be established and the composition can be freeze dried in the second position of the plunger, whereas the vacuum in the vacuum chamber can be retained in the first position of the plunger. However, alternatively said one or more vacuum bypass channels are configured such that a fluid communication can be provided directly between the vacuum chamber and the ambient atmosphere independent of the position of the plunger, e.g. via a (second) pressure valve located directly at the vacuum chamber. Alternatively said one or more vacuum bypass channels may be formed in the plunger.

Hence, the one or more vacuum bypass channels may be configured to break the sealing between the vacuum chamber and the plunger at a predefined axial position of the plunger inside the vacuum chamber. Furthermore, said one or more vacuum bypass channels may be formed in the vacuum chamber. E.g. said one or more vacuum bypass channels may be one or more longitudinal grooves formed in the inner surface, e.g. at the proximal end of the vacuum chamber.

Figure 17A:
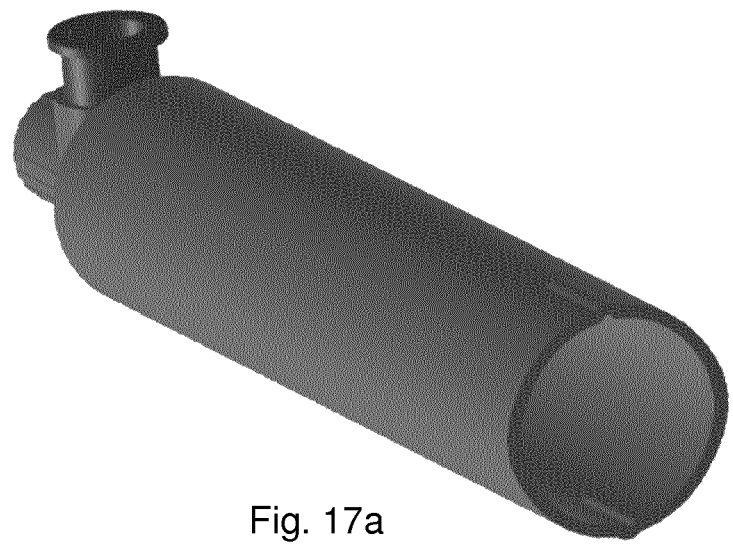
FIGS. 17a-b show perspective proximal views of two different embodiments of the barrel of the presently disclosed syringe.
Figure 17B:
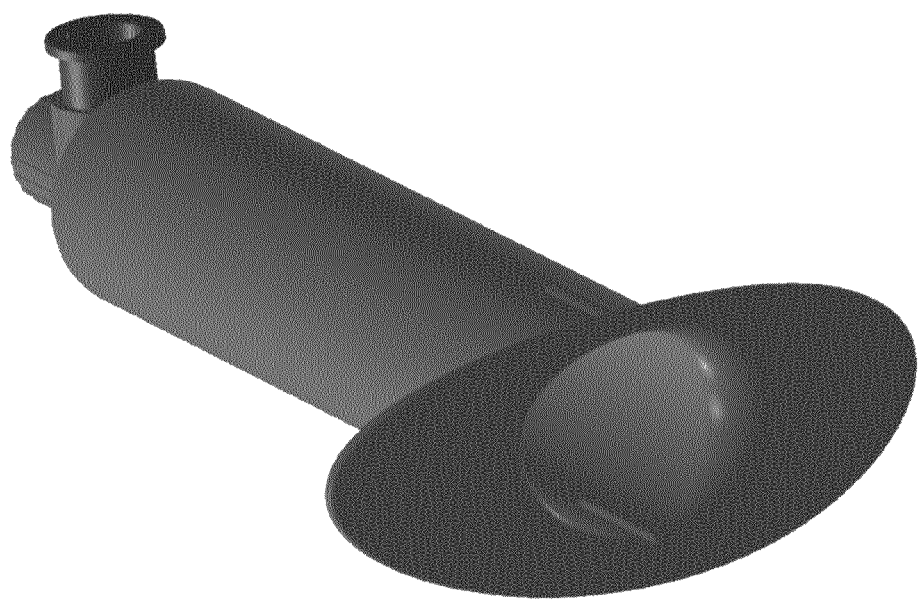

In one embodiment of the presently disclosed syringe the barrel is formed in a single piece of material. The barrel may advantageously be suitable and/or adapted for manufacture by means of single cycle injection moulding, i.e. the barrel may advantageously be manufactured by means of single cycle injection moulding. I.e. the vacuum chamber, the pressure chamber and the connector portion may be integrated and/or incorporated to form a single element, e.g. as illustrated in FIGS. 16-18. This may help to ensure that a vacuum can be established and retained inside the vacuum chamber.

However, alternatively the vacuum chamber, the pressure chamber and the connector portion may be formed as separate elements and configured to be assembled during manufacture of the syringe.

Further, the pressure chamber and the connector portion may be formed as one element and configured to be assembled with the vacuum chamber during manufacture of the syringe. Alternatively the vacuum chamber and the pressure chamber may be formed as one element and configured to be assembled with the connector portion during manufacture of the syringe.

A barrel 1, 1' of the presently disclosed syringe is exemplified in FIGS. 16-18. The barrel 1 in FIG. 16a is provided with a vacuum chamber, a pressure chamber 3, a connector portion 4 and a flange 8 formed in a single piece and suitable for manufacture by single cycle injection moulding. The pressure valve 5 inserted in the pressure chamber 3 is provided with a valve flange 6. In FIG. 16a the pressure valve is located in a first position whereas in FIG. 16b the pressure valve has been displaced to a second position. This is more clearly seen in FIGS. 16c (first position of pressure valve) and 16d (second position). In the second position of the pressure valve 5 the valve flange 6 abuts the pressure chamber 3.

The cut-through illustrations in FIGS. 18a and 18b more clearly shows the configuration of the pressure valve 5. In the first position in FIG. 18a the pressure valve blocks the fluid communication between the outlet 11 of the internal volume 2' of vacuum chamber 2 and the outlet 7 of the connector portion 4. In the second position of the pressure valve 5 in FIG. 18b a fluid communication is provided (as illustrated by the dotted line/arrow) between the surroundings and the internal volume 2' of the vacuum chamber 2 via the pressure chamber 3 and the outlet 7 of the connector portion 4, i.e. liquid can enter the vacuum chamber 2' to mix with a dry composition, e.g. to form a wet paste that subsequently can be controllably released via the outlet 7 by operating a plunger (not shown) arranged in the barrel 1, 1'. The barrel 1' in FIG. 17a does not have a flange.

As seen from FIG. 18 the pressure valve 5 is formed like a cylinder with a circumferential groove 12 that forms the fluid opening in the second position of the pressure valve. I.e. the pressure valve 5 is formed like two hollow cylinders that are attached to each other by means of the centrally located rod 13. Even though the rod 13 is located centrally in the fluid passageway, liquid that enters the vacuum chamber 2 via the outlet 7, and paste that is released from the barrel 1, 1' through the outlet 7 can easily pass the rod 13. The pressure valve 5 as illustrated in FIG. 18 is rotation symmetric.

The connector portion 4 is provided with an internal thread 10, most clearly seen in FIG. 18. This may help to provide a secure, tight and tamper-free connection with an external liquid container (having a connector portion with a matching thread) prior to suction of liquid into the vacuum chamber when the (wet) paste is to be formed.

Vacuum bypass channels 9 are provided in FIGS. 16-18 as longitudinally extending grooves in the proximal end of the vacuum chamber 2. When the plunger (not shown) is arranged in the barrel 1, 1' below these vacuum channels the plunger sealably engages the vacuum chamber. However, when the distal part of the plunger is flush with the bypass vacuum channels 9, this sealing is not tight, because a fluid, and in particular air, connection is established between the vacuum chamber 2' and the surrounding atmosphere across the plunger via the vacuum bypass channels 9. I.e. during free-drying of paste inside the vacuum chamber 2' suction applied at the proximal end of the barrel can establish a vacuum inside the pressure chamber 2' and thereby expand the dry paste. At the end of the freeze-drying and expansion process, the plunger can be displaced to a position below the vacuum bypass channels, thereby sealably engaging the vacuum chamber 2 and subsequently retaining the freeze-dried paste in a vacuum.

Figure 19A:
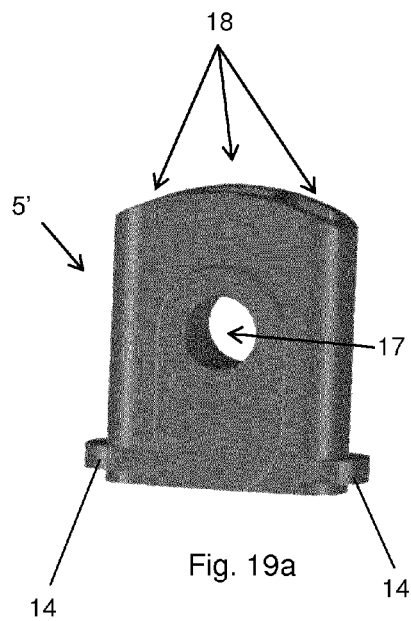
FIG. 19a shows another embodiment of a pressure valve.
Figure 19B:
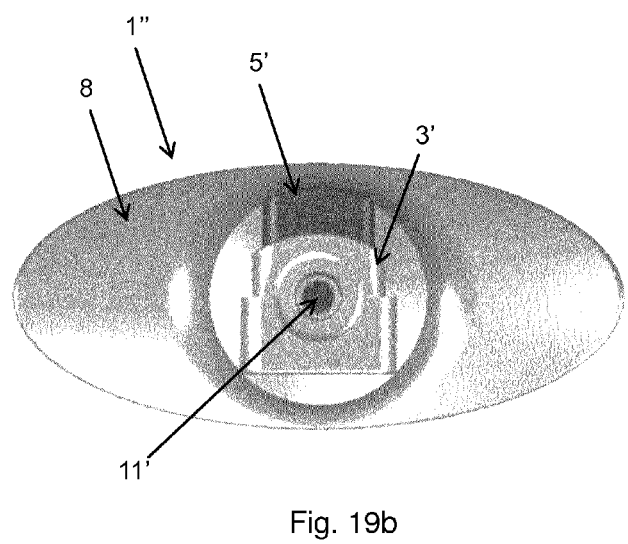
Figure 19C:
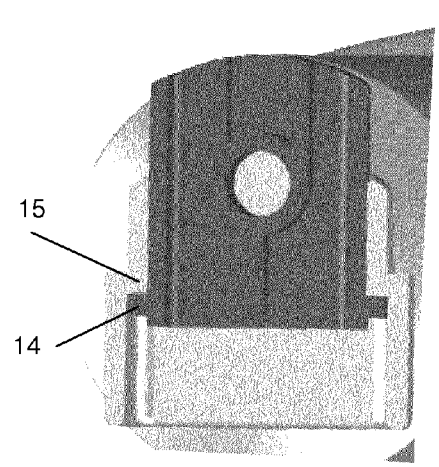
FIGS. 19c-d show cut-through frontal view of the configuration of the pressure valve from FIG. 19a inside the pressure chamber from FIG. 19b.
Figure 19D:
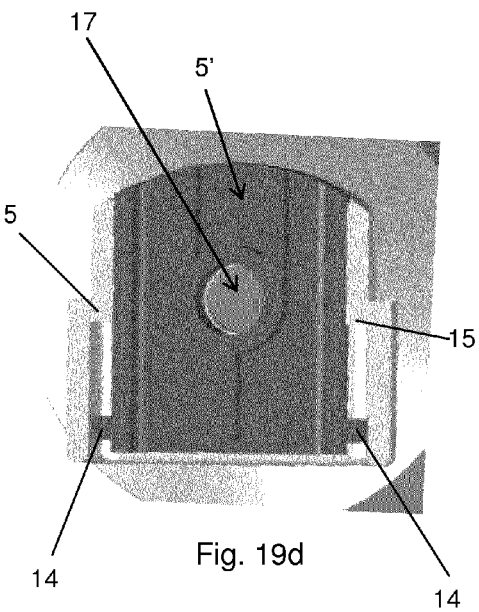

Another exemplary barrel 1" of the presently disclosed syringe is exemplified in FIG. 20 having another embodiment of the pressure valve 5' and the pressure chamber 3' as illustrated in greater detail in FIG. 19, with FIG. 19a showing a close-up of the pressure valve alone. This pressure valve 5' is slim and provided in a substantially rectangular shape. An aperture 17 forms the fluid passageway in the second position of pressure valve inside the pressure chamber 3'. The outside shape of the pressure valve 5' matches the inside shape of the pressure chamber 3'. FIG. 19b shows the pressure valve 5' inside the pressure chamber 3' in the first position of the pressure valve 5', where the fluid passageway is blocked and a vacuum can be retained inside the vacuum chamber 2. In FIG. 19b the pressure valve 5' is seen to protrude upwards from the pressure chamber 3', i.e. it protrudes radially from the pressure chamber 3' with respect to the longitudinal axis of the barrel 2. In FIGS. 19c and 19d the pressure chamber 3' has been cut-through such that the configuration of the pressure valve 5' inside the pressure chamber 3' can be seen. In FIG. 19c the pressure valve 5' is in the first position, i.e. extending radially from the pressure chamber 3'. The pressure valve 5' and the pressure chamber 3' are configured such that the pressure valve is radially limited in this first position by means of protrusions 14 on the pressure valve 5' that abuts a narrowing 15 of the inner side wall of the pressure chamber 3', i.e. the pressure valve 5' cannot extend further outwards when in the first position. This helps to ensure that the pressure valve 5' is not accidentally removed from the pressure chamber 3' thereby possibly breaking a vacuum sealing inside the vacuum chamber 2. In FIG. 19d the pressure valve 5' is in the second position. The pressure valve 5' is now completely submerged in the pressure chamber 3'. The rounded top surface of the pressure valve 5' matches a corresponding rounded top surface of the pressure chamber 3' such that the upper surfaces of the pressure valve 5' and the pressure chamber 3' are flush with each other.

Figure 20A:
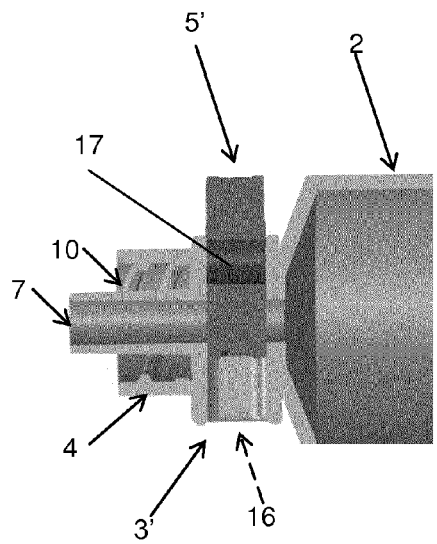
FIGS. 20a-b are cut-through side view illustrations of the pressure valve from FIG. 19a inside the pressure chamber from FIG. 19.
Figure 20C:
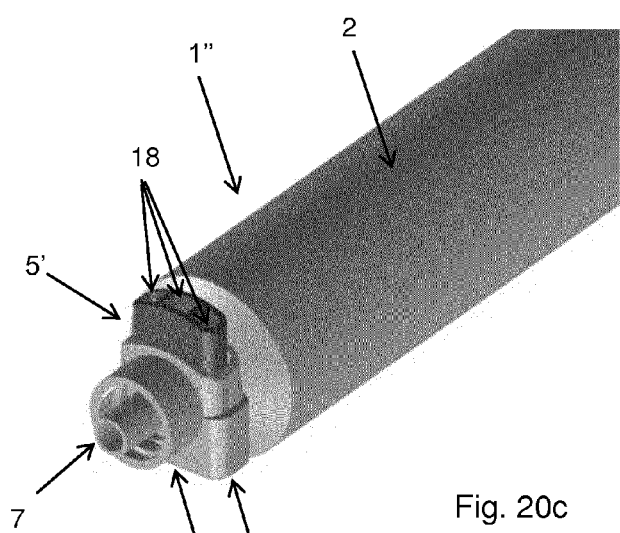
FIGS. 20c-d are perspective view illustrations of the barrel with the pressure valve and pressure chamber from FIG. 19.
Figure 20B:
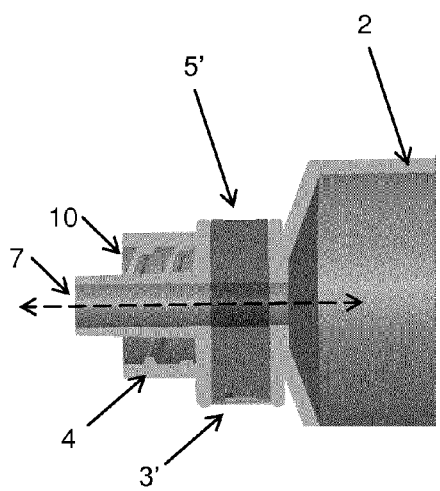
Figure 20D:
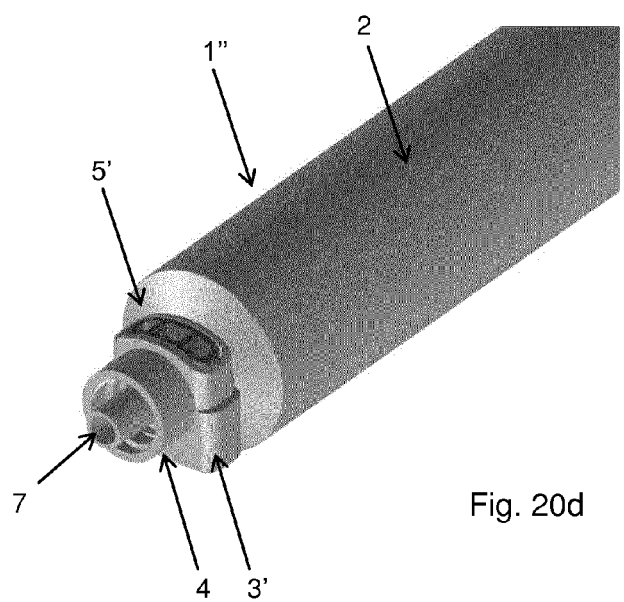

FIGS. 20a-b show cut-through side view illustrations of the pressure valve 5' inside the pressure chamber 3' with the first position of the pressure valve in FIG. 20a and the second position in FIG. 20b. As seen in FIG. 20a the fluid passageway 7 is blocked by the pressure valve 5', whereas in FIG. 20b the aperture 17 of the pressure valve 5' establishes a fluid connection as indicated by the stippled horizontal arrow in FIG. 20b. FIG. 20b also illustrates how the pressure valve 5' does not protrude from the pressure chamber 3' in this second position. This helps to ensure that once the fluid passageway has been established by the pressure valve 5' in the second position, the position of the pressure valve 5' is not easily changed because it is submerged inside the pressure chamber 3'.

A stippled arrow in FIG. 20a indicates the opening 16 where through the pressure valve 5' can be inserted into the pressure chamber 3'. The barrel 1" is also suitable for single cycle injection molding. After manufacture the pressure valve 5' can be inserted through the opening 16. The pressure valve 5' in itself is also suitable for single cycle injection molding. The three top holes 18 indicated in FIGS. 19a and 20c are provided to make the pressure valve 5' suitable for injection molding.

Haemostatic Sheet

In one embodiment the dry composition is in the form of a sheet, i.e. a substantially flat composition.

A dry composition in the form of a sheet may be obtained by spreading the paste of the invention thinly and evenly on a surface, vacuum expanding the paste, freezing and drying of the paste to obtain a substantially flat dry sheet composition. A dry composition in the form of a sheet will upon contact with a liquid reconstitute spontaneously to form a paste. Thus, a dry composition in the form of a sheet has the advantages of both traditionally used surgical sponges in that it can cover relatively large areas and the advantage of a paste in that it conforms easily to uneven surfaces upon wetting.

The dry composition in the form of a sheet is soft and flexible.

In one embodiment the invention relates to a dry composition in the form of a sheet for use in haemostasis and/or wound healing.

In one embodiment, the sheet is not pre-wetted before use, i.e. before application to a wound. In this case, the sheet will reconstitute in situ on the bleeding wound upon contact with blood, wound exudate, and/or other bodily fluids.

The height of the dry sheet composition is in one embodiment between about 0.5 mm and about 10 mm, preferably between about 1 mm and 5 mm, more preferred between about 1 mm and 3 mm, such as about 2 mm.

The size (width and depth) of the dry sheet composition depends on the intended use of the sheet and can be selected by the skilled person. The dry sheet material may e.g. be rectangular, square or circular. For example, the dry sheet composition may e.g. be in the form of a rectangle of approximately 5 cm×10 cm, 2 cm×6 cm, 6 cm×8 cm or 8 cm×12 cm.

In one embodiment, the dry sheet composition is cut into the desired shape prior to use.

Vacuum

According to the method of the present disclosure, the paste is expanded by subjecting the paste to a reduced pressure, i.e. to pressures below ambient pressure, i.e. usually less than 1000 mbar (a low vacuum). Vacuum expansion results in an increase in the total volume of the paste by expansion of entrapped air or another gas within interstitial pores or compartments of the wet paste.

The pressure of the vacuum is selected so that the paste expands to a sufficient degree without collapsing. Thus, the pressure must not be too low, which will result in the paste collapsing. Vacuum expansion of the paste may e.g. be performed in a freeze-dryer.

Vacuum expansion of the paste is a result of one of the universal laws of physics: the ideal gas law, which governs that the volume of a gas will increase upon a decrease in pressure. The ideal gas law equation is:

$$PV=nRT$$

where P is the pressure of the gas, V is the volume of the gas, n is the amount of substance of gas (in moles), T is the temperature of the gas and R is the ideal, or universal, gas constant.

Subjecting a wet paste to a sub-atmospheric pressure results in an expansion of the air or other gas within the interstitial spaces (pores) of the paste, which in turn leads to an increase in the total volume of the paste and a decrease in the density of the paste. After drying of the paste composition to achieve a dry paste composition, the increased pore size results in increased permeability and wettability and thus an increased reconstitution rate of the dry composition. Thus, in one embodiment, the present disclosure relates to a method for adapting paste volume by adjusting paste density by subjecting a wet paste to a reduced pressure.

In one embodiment the density of the paste is decreased by at least a factor 0.95 as a result of the vacuum expansion, such as at least a factor 0.90, for example at least a factor 0.85, such as at least a factor 0.80, for example at least a factor 0.75, such as at least a factor 0.70, for example at least a factor 0.65, such as at least a factor 0.60, for example at least a factor 0.55, such as at least a factor 0.50 as a result of the vacuum expansion. Preferably, the density of the paste is decreased by at least a factor 0.8 as a result of the vacuum expansion.

In one embodiment the density of the paste is decreased by about a factor 0.75 as a result of the vacuum expansion.

Prior to vacuum expansion of the paste, the density of the wet paste may e.g. be in the range of about 0.5 g/ml to about 1 g/ml, such as between about 0.6 g/ml to about 0.9 g/ml, for example between about 0.7 g/ml to about 0.8 g/ml.

For example, the density of a gelatine paste prior to expansion is usually within the range of about 0.60 g/ml to about 0.80 g/ml, such as about 0.65 g/ml to about 0.75 g/ml, such as about 0.7 g/ml.

After vacuum expansion, the density of the wet paste may e.g. be in the range of about 0.1 g/ml to about 0.8 g/ml, more preferred between about 0.2 g/ml to about 0.7 g/ml, for example about 0.2 g/ml to about 0.6 g/ml, such as about 0.2 g/ml to about 0.5 g/ml.

For example, the density of a gelatine paste after expansion is usually within the range of about 0.2 g/ml to about 0.6 g/ml, more preferred between about 0.3 g/ml to about 0.6 g/ml, such as between about 0.4 g/ml to about 0.5 g/ml.

The volume of the paste, by subjecting the paste to a reduced pressure, is approximately increased by at least about a factor 1.05, such as at least a factor 1.1, for example at least a factor 1.2, such as at least a factor 1.3, for example at least a factor 1.4, such as at least a factor 1.5, for example at least a factor 1.6, such as at least a factor 1.7, for example at least a factor 1.8, such as at least a factor 1.9, for example at least a factor 2.0.

In one embodiment, the volume of the paste is increased by from about a factor 1.05 to about a factor 2.0, such as about a factor 1.1 to about a factor 1.8, for example about a factor 1.2 to about a factor 1.6 as a result of the vacuum expansion of the wet paste.

After drying, the density of the dried paste composition is further decreased due to removal of the water. After drying of the vacuum expanded wet paste, the density of the dry paste composition is thus usually within the range of about 0.1 mg/ml to about 100 mg/ml, more preferred between about 1 mg/ml to about 50 mg/ml, such as between about 5 mg/ml to about 40 mg/ml.

For example, a dry vacuum expanded composition comprising gelatine prepared by the method of the present disclosure usually has a density of between about 1 mg/ml to about 40 mg/ml, such as between about 5 mg/ml to about 35 mg/ml, for example between about 10 mg/ml to about 35 mg/ml.

In one embodiment, the density of the vacuum expanded dry composition is within the range of about 1 mg/ml to about 40 mg/ml, more preferred between about 5 mg/ml to about 40 mg/ml, such as between about 5 mg/ml to about 38 mg/ml, for example between about 5 mg/ml to about 36 mg/ml, such as between about 5 mg/ml to about 34 mg/ml, for example between about 5 mg/ml to about 32 mg/ml, such as between about 5 mg/ml to about 30 mg/ml, for example between about 5 mg/ml to about 28 mg/ml, such as between about 5 mg/ml to about 26 mg/ml, for example between about 5 mg/ml to about 24 mg/ml, such as between about 5 mg/ml to about 22 mg/ml, for example between about 5 mg/ml to about 20 mg/ml.

In one embodiment, the paste is subjected to a reduced pressure of at least 10 mbar less than ambient pressure, for example at least 50 mbar less than ambient pressure, such as at least 100 mbar less than ambient pressure, for example at least 150 mbar less than ambient pressure, such as at least 200 mbar less than ambient pressure, for example at least 250 mbar less than ambient pressure, such as at least 300 mbar less than ambient pressure, for example at least 350 mbar less than ambient pressure, such as at least 400 mbar less than ambient pressure, for example at least 450 mbar less ambient pressure, such as at least 500 mbar less than ambient pressure, for example at least 550 mbar less ambient pressure, such as at least 600 mbar less than ambient pressure, for example at least 650 mbar less ambient pressure, such as at least 700 mbar less than ambient pressure, for example at least 750 mbar less than ambient pressure, such as at least 800 mbar less than ambient pressure, for example at least 850 mbar less than ambient pressure, such as at least 900 mbar less ambient pressure.

The pressure of the vacuum is preferably selected so that the pressure is at least 50 mbar less than ambient pressure but no more than 900 mbar less than ambient, such as at least 100 mbar less than ambient pressure but no more than 800 mbar less than ambient pressure.

The pressure of the vacuum is preferably selected so that the pressure is no more than 1000 mbar less than ambient pressure, such as no more than 900 mbar less than ambient pressure, for example no more than 800 mbar less than ambient pressure, such as no more than 700 mbar less than ambient pressure, for example no more than 600 mbar less than ambient pressure, such as no more than 500 mbar less than ambient pressure.

In one embodiment, the pressure of the vacuum is between less than 1000 mbar and 100 mbar, such as between 950 mbar and 100 mbar, for example between 900 mbar and 100 mbar, such as between 850 mbar and 100 mbar, for example between 800 mbar and 100 mbar, such as between 750 mbar and 100 mbar, for example between 700 mbar and 100 mbar, such as between 650 mbar and 100 mbar, for example between 600 mbar and 100 mbar, such as between 550 mbar and 100 mbar, for example between 500 mbar and 100 mbar, such as between 450 mbar and 100 mbar, for example between 400 mbar and 100 mbar, such as between 350 mbar and 100 mbar, for example between 300 mbar and 100 mbar, such as between 250 mbar and 100 mbar, for example between 200 mbar and 100 mbar.

In one embodiment, the pressure of the vacuum is between less than 1000 mbar and 200 mbar, such as between 1000 mbar and 250 mbar, for example between 1000 mbar and 300 mbar, such as between 1000 mbar and 350 mbar, for example between 1000 mbar and 400 mbar, such as between 1000 mbar and 450 mbar, for example between 1000 mbar and 500 mbar, such as between 1000 mbar and 550 mbar, for example between 1000 mbar and 600 mbar, such as between 1000 mbar and 650 mbar, for example between 1000 mbar and 700 mbar, such as between 1000 mbar and 750 mbar, for example between 1000 mbar and 800 mbar, such as between 1000 mbar and 850 mbar, for example between 1000 mbar and 900 mbar, such as between 1000 mbar and 950 mbar.

In a preferred embodiment, the pressure of the vacuum is between about 900 mbar and 500 mbar.

The expansion rate depends on the vacuum pump and the size of the vacuum chamber, i.e. how fast pressure in the chamber can be decreased to the desired level. The low vacuum levels according to the present disclosure are achieved almost instantaneously, thus expansion of the paste occurs essentially instantaneously after starting the vacuum pump.

Vacuum expansion is usually performed at a temperature above the freezing point of the paste. In one embodiment, vacuum expansion is performed at ambient temperature or at temperatures below ambient temperature, such as at temperatures of about 0° C. to about 25° C., such as at about 2° C. to about 20° C., for example about 2° C. to about 15° C., such as at about 2° C. to about 10° C., such as about 4° C. to about 20° C., for example about 4° C. to about 15° C., such as at about 4° C. to about 10° C. When the paste comprises sensitive bioactive agents, such as thrombin, vacuum expansion is preferably performed at temperatures below ambient temperatures.

Freezing of the Paste

When the paste of the invention has been expanded to a desired degree, the paste is usually frozen by subjecting the paste to a temperature below 0° C. for a period of time sufficient for the paste to freeze. Freezing occurs without releasing the vacuum and freezing of the paste thus locks the expanded paste structure in place. Thus, further changes in pressure hereafter will not affect the volume of the frozen paste. The freezing is preferably performed in a freeze-dryer.

The temperature selected for freezing the paste depends on the freezing point of the paste and/or the glass transition temperature of the paste and can be determined by the skilled person. The desired temperature of the frozen paste is approximately 5° C. less than the lowest of the freezing point of the paste and the glass transition temperature. E.g. if the freezing point of a paste is −35° C., the paste should be cooled to about −40° C.

Drying the Paste

According to the invention the haemostatic paste is dried to obtain the dry haemostatic composition. The paste may be dried by any suitable methods known to a person of skill.

In a preferred embodiment, the paste is freeze-dried. Any suitable freeze-drying technique and equipment known to the person of skill may be used. When freeze-drying is used to prepare the dried paste composition of the present invention, expansion, freezing and drying can advantageously be performed as a continuous process in a single apparatus.

Freeze-drying (also known as lyophilisation and cryodesiccation) is a dehydration process typically used to preserve a perishable material or make the material more convenient for transport. Freeze-drying works by freezing the material and then reducing the surrounding pressure to allow the frozen water in the material to sublimate directly from the solid phase to the gas phase.

There are essentially three categories of freeze-dryers: the manifold freeze-dryer, the rotary freeze-dryer and the tray style freeze-dryer. Two components are common to all types of freeze-dryers: a vacuum pump to reduce the ambient gas pressure in a vessel containing the substance to be dried and a condenser to remove the moisture by condensation on a surface cooled to −40 to −80° C. The manifold, rotary and tray type freeze-dryers differ in the method by which the dried substance is interfaced with a condenser. In manifold freeze-dryers a short usually circular tube is used to connect multiple containers with the dried product to a condenser. The rotary and tray freeze-dryers have a single large reservoir for the dried substance.

Rotary freeze-dryers are usually used for drying pellets, cubes and other pourable substances. The rotary dryers have a cylindrical reservoir that is rotated during drying to achieve a more uniform drying throughout the substance. Tray style freeze-dryers usually have rectangular reservoir with shelves on which products, such as pharmaceutical solutions and tissue extracts, can be placed in trays, vials and other containers.

Manifold freeze-dryers are usually used in a laboratory setting when drying liquid substances in small containers and when the product will be used in a short period of time. A manifold dryer will dry the product to less than 5% moisture content. Without heat, only primary drying (removal of the unbound water) can be achieved. A heater must be added for secondary drying, which will remove the bound water and will produce a lower moisture content.

Tray style freeze-dryers are typically larger than the manifold dryers and are more sophisticated. Tray style freeze-dryers are used to dry a variety of materials. A tray freeze-dryer is used to produce the driest product for long-term storage. A tray freeze-dryer allows the product to be frozen in place and performs both primary (unbound water removal) and secondary (bound water removal) freeze-drying, thus producing the driest possible end-product. Tray freeze-dryers can dry products in bulk or in vials or other containers. When drying in vials, the freeze-drier is supplied with a stoppering mechanism that allows a stopper to be pressed into place, sealing the vial before it is exposed to the atmosphere. This is used for long-term storage, such as vaccines.

Improved freeze drying techniques are being developed to extend the range of products that can be freeze dried, to improve the quality of the product, and to produce the product faster with less labor.

Ever since the 1930s, industrial freeze drying has been dependent on a single type of equipment: the tray freeze drier. In 2005 a quicker and less-labor intensive freeze drying method was developed for bulk materials. This freeze drying process proved to be able to produce free-flowing powder from a single vessel. Known as [Active Freeze Drying] AFD technology, the new process used continuous motion to improve mass transfer and hence cutting processing time, while also eliminating the need to transfer to and from drying trays and downstream size reduction devices.

There are four stages in the complete freeze-drying process: pretreatment, freezing, primary drying, and secondary drying.

Pretreatment includes any method of treating the product prior to freezing. This may include concentrating the product, formulation revision (i.e., addition of components to increase stability and/or improve processing), decreasing a high vapor pressure solvent or increasing the surface area. In many instances the decision to pretreat a product is based on theoretical knowledge of freeze-drying and its requirements, or is demanded by cycle time or product quality considerations. Methods of pretreatment include: Freeze concentration, Solution phase concentration, Formulation to Preserve Product Appearance, Formulation to Stabilize Reactive Products, Formulation to Increase the Surface Area, and Decreasing High Vapor Pressure Solvents.

In a lab, freezing is often done by placing the material in a freeze-drying flask and rotating the flask in a bath, called a shell freezer, which is cooled by mechanical refrigeration, dry ice and methanol, or liquid nitrogen. On a larger scale, freezing is usually done using a freeze-drying machine. In this step, it is important to cool the material below its triple point, the lowest temperature at which the solid and liquid phases of the material can coexist. This ensures that sublimation rather than melting will occur in the following steps. Larger crystals are easier to freeze-dry. To produce larger crystals, the product should be frozen slowly or can be cycled up and down in temperature. This cycling process is called annealing. In other cases it is better that the freezing is done rapidly, in order to lower the material to below its eutectic point quickly, thus avoiding the formation of ice crystals. Usually, the freezing temperatures are between −40° C. and −80° C. The freezing phase is the most critical in the whole freeze-drying process, because the product can be spoiled if badly done.

Amorphous materials do not have a eutectic point, but they do have a critical point, below which the product must be maintained to prevent melt-back or collapse during primary and secondary drying.

During the primary drying phase, the pressure is lowered (to the range of a few millibars or less), and enough heat is supplied to the material for the water to sublime. The amount of heat necessary can be calculated using the sublimating molecules' latent heat of sublimation. In this initial drying phase, about 95% of the water in the material is sublimated. This phase may be slow (can be several days in the industry), because, if too much heat is added, the material's structure could be altered.

In this phase, pressure is controlled through the application of a medium vacuum. The vacuum speeds sublimation, making it useful as a deliberate drying process. Furthermore, a cold condenser chamber and/or condenser plates provide a surface(s) for the water vapour to re-solidify on. This condenser plays no role in keeping the material frozen; rather, it prevents water vapor from reaching the vacuum pump, which could degrade the pump's performance. Condenser temperatures are typically below −50° C.

It is important to note that, in this range of pressure, the heat is brought mainly by conduction or radiation; the convection effect is negligible, due to the low air density.

The vapour pressure of water is the pressure at which water vapour is saturated. At higher pressures water would condense. The water vapour pressure is the partial pressure of water vapour in any gas mixture saturated with water. The water vapour pressure determines the temperature and pressure necessary for freeze-drying to occur. Vapour pressure of water (mTorr=millitorr; mB=millibar) is shown in the below table:

| Temp (C.) | mTorr | mB |
|---|---|---|
| 0 | 4579 | 6.104 |
| −4 | 3280 | 4.372 |
| −8 | 2326 | 3.097 |
| −12 | 1632 | 2.172 |
| −16 | 1132 | 1.506 |
| −20 | 930 | 1.032 |
| −24 | 526 | 0.6985 |
| −28 | 351 | 0.4669 |
| −32 | 231 | 0.3079 |
| −36 | 150 | 0.2020 |
| −40 | 96.6 | 0.1238 |
| −44 | 60.9 | 0.0809 |
| −48 | 37.8 | 0.0502 |
| −52 | 23.0 | 0.0300 |
| −56 | 13.8 | 0.0183 |
| −60 | 8.0 | 0.0107 |
| −64 | 4.6 | 0.0061 |
| −68 | 2.6 | 0.0034 |
| −72 | 1.4 | 0.0018 |

The secondary drying phase aims to remove unfrozen water molecules, since the ice was removed in the primary drying phase. This part of the freeze-drying process is governed by the material's adsorption isotherms. In this phase, the temperature is raised higher than in the primary drying phase, and can even be above 0° C., to break any physico-chemical interactions that have formed between the water molecules and the frozen material. Usually the pressure is also lowered in this stage to encourage desorption (typically in the range of microbars). However, there are products that benefit from increased pressure as well.

After the freeze-drying process is complete, the vacuum may be broken with an inert gas, such as nitrogen, before the material is sealed.

In one embodiment, the vacuum is retained in the product chamber to allow for easy addition of liquid for reconstitution.

At the end of the operation, the final residual water content in the freeze-dried product is in general very low, such as around 2% or lower.

The freeze-drying process transforms the paste into a "cake-like" dry composition, which upon addition of an adequate amount of an aqueous medium, such as water, will form a ready-to use paste spontaneously, i.e. no mechanical mixing/reconstitution is required for said paste to form.

In an alternative embodiment of the present disclosure, the expanded paste is not frozen prior to drying of the paste. Neither is the paste dried by freeze-drying. Rather the low vacuum is upheld while the paste is dried by subjecting the expanded paste to an increased temperature until the paste is dry. The increased temperature is typically in the range of about 30-200° C., such as about 50° C. to about 150° C. Thus, in an alternative embodiment, the method of the present disclosure is a method for preparing a dry composition comprising the steps of:
a. providing an agent in powder form and an aqueous medium,
b. mixing the agent in powder form and the aqueous medium to obtain a paste,
c. subjecting the paste to a reduced pressure thereby expanding the paste, and, and
d. drying the paste by dry heat.

Reconstitution

The present inventors have found that expanding a wet paste composition by vacuum, preferably low vacuum before freeze-drying greatly enhances the reconstitution rate of said paste. Thus, a paste which has been expanded by low vacuum reconstitutes faster than a comparable dry paste composition, which has not been expanded by low vacuum. A paste that has been expanded by vacuum and dried reconstitutes spontaneously to form a substantially homogenous flowable paste without any mechanical mixing. For example, a vacuum expanded, dried gelatine paste composition being present in a medical delivery device will reconstitute to a ready-to-use paste suitable for direct delivery to a patient without any mechanical mixing required upon addition of an amount of an aqueous medium to the medical delivery device having the dried gelatine paste composition disposed therein.

Vacuum expansion expands entrapped air pockets within the paste and such expanded air pockets are retained in the dried paste composition. The presence of larger air pockets in the dry composition enables the wetting of the dry composition due to a larger contact surface area between the dried composition and the liquid. It also facilitates unhindered distribution of the liquid into the dry composition due to the formed channels.

The inventors have also discovered that the volume of a paste aliquot is generally higher in samples being aliquoted first as opposed to last from a single batch of paste. This is thought to be due to a partial collapse of the paste occurring over time causing variations in paste density. Such variations in density can lead to undesirable variations in the reconstitution time. Vacuum expansion of the paste prior to drying is able to reduce or even eliminate such "intra-batch" variations in paste density and thus lead to consistently fast reconstitution of the dried pastes. Thus, vacuum expansion provides a higher degree of reproducibility with regards to the reconstitution time.

The dry composition may be reconstituted by adding a suitable aqueous medium. The aqueous medium may be added by any suitable mechanism. Preferably, the aqueous medium is sterile. The aqueous medium is added in an amount sufficient to obtain a wet paste of a desired consistency. In one embodiment, the volume of liquid added to the dry composition corresponds essentially to the volume of liquid which was removed by the drying procedure. In case a thinner paste composition is desired, more liquid can be added to the dried paste than was initially removed by the drying procedure. Preferably, the paste is reconstituted by adding an amount of liquid to a container, such as a medical delivery device, having the dried paste composition disposed therein, even more preferred to the same container which held the paste during the vacuum expansion, freezing and drying steps.

In one embodiment, the dry composition is reconstituted by attaching a second container holding an amount of an aqueous medium to the first container holding the dry composition. The first container holding the dry composition is preferably a syringe, such as the vacuum chamber of the herein disclosed syringe.

Preferably, the container comprising the reconstitution liquid is essentially free from air or another gas. The advantage of this is that reconstitution is independent of how the containers are oriented in space in relation to each other.

In one embodiment, there is a vacuum inside the product chamber of the first container, i.e. the pressure inside the product chamber of the first container is less than that of the surroundings, i.e. less than atmospheric pressure.

In one embodiment, the pressure in the second container is greater than the pressure in the first container, the pressure difference allowing for automatic liquid flow from the second container to the first container. This can e.g. be achieved by the first container having a pressure below atmospheric pressure, while the pressure inside the second container is about atmospheric pressure. Thus, upon opening a valve separating the two containers, the aqueous medium is automatically drawn into the product chamber of the first container due to the pressure difference. The result is a reconstituted paste, see e.g. FIGS. 12-13.

Thus, in one embodiment, the present disclosure relates to a method for reconstituting a dry paste composition comprising the steps of:
a) providing a first container comprising a product chamber containing a dry paste composition and a valve, preferably wherein the pressure within the product chamber is less than the surrounding atmospheric pressure,
b) providing a second container comprising an aqueous medium, preferably wherein the pressure within the second container is greater than the pressure within the product chamber of the first container,
c) connecting the first container and the second container using suitable connecting means, and
d) opening the valve.

In one embodiment, the second container is a collapsible container such as a plastic bag. Upon attachment to the first container and opening of the valve, the bag collapses due to the pressure difference, thus allowing for liquid flow from the bag to the product chamber and reconstitution of the paste as illustrated in FIGS. 12-13.

In one embodiment, the second container is a non-collapsible container comprising a plunger, such as a rigid- or semi-rigid plastic container. Upon attachment to the first container and opening of the valve the plunger allows for liquid flow from the aqueous medium container to the product chamber and reconstitution of the paste without exerting manual pressure upon the plunger as illustrated in FIGS. 12-13.

Preferably a ready-to-use paste forms spontaneously upon addition of liquid to the dry composition disposed within the container within less than about 30 seconds, preferably within less than about 20 seconds, more preferred within less than about 10 seconds, even more preferred within less than about 5 seconds, such as less than about 3 seconds, for example less than about 2 seconds. The reconstituted paste usually requires no further mixing or other forms of manipulations before use. Thus, when the dried paste composition is present in a medical delivery device, such as a syringe, it can be applied directly to a patient immediately after liquid addition, e.g. for haemostatic purposes by extruding the paste from the medical delivery device to a bleeding wound.

In a preferred embodiment, a ready-to-use paste forms within less than about 5 seconds, such as less than about 3 seconds, for example less than about 2 seconds.

Figure 14:
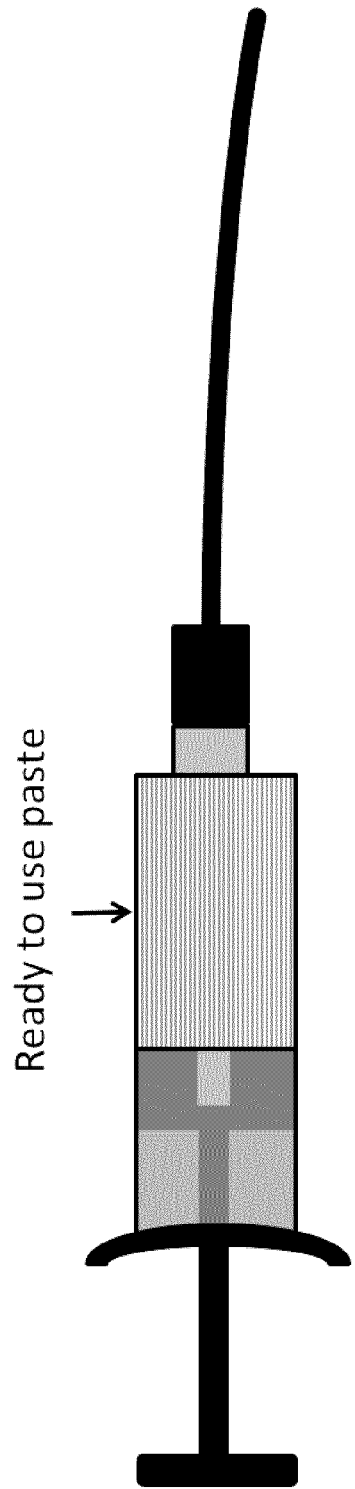

After reconstitution, the container, for example a syringe, such as the herein disclosed syringe, may be fitted with an applicator tip suitable for administering the paste in a more precise manner as illustrated in FIG. 14.

In one embodiment the applicator tip is bendable or malleable and will maintain a desired configuration chosen by the user so that it stays at an optimum angle for easy access and exact product placement. Further, it can be cut to a desired length with a pair of nurses dressing scissors or similar type of scissors. These features allow for accurate and convenient application of the paste. In one embodiment the applicator tip is essentially as described in WO 2011/047753.

Outer Packaging

In one embodiment the dry composition contained within e.g. a syringe, such as the herein disclosed syringe, or other containment unit, is further contained within an outer packaging so that the product is kept sterile until use. This will allow the user to remove the outer packaging and transfer the haemostatic composition into a sterile field. Here, a suitable amount of aqueous medium can be added, whereupon a ready-to-use haemostatic paste forms spontaneously within seconds without any need for mechanical agitation, stirring or mixing.

The outer packaging is usually made from a flexible, semi-rigid or rigid material and typically consists of materials such as plastic, aluminium foil and/or plastic laminate, where the plastic may be selected from the group consisting of PET, PETG, PE, LLDPE, CPP, PA, PETP, METPET, Tyvek and optionally bonded with an adhesive, such as polyurethane, or co-extruded.

In one embodiment, the outer packaging is an aluminium foil outer packaging.

The outer packaging preferably forms a complete barrier to moisture.

The outer packaging is preferably able to endure sterilisation treatment such as by radiation.

Sterilisation

The dry composition of the present disclosure is preferably sterile. Any suitable sterilisation technique known in the art may be utilised. The sterilisation preferably occurs after the packaging step, i.e. when the dry composition is contained within an outer packaging. Thus, in a preferred embodiment sterilisation is terminal sterilisation.

Sterilisation refers to any process that effectively kills or eliminates transmissible agents (such as fungi, bacteria, viruses, prions and spore forms etc.). Sterilisation of the dry composition can be achieved through e.g. application of heat, chemicals, and irradiation. Heat sterilization include autoclaving (uses steam at high temperatures) and dry heat; radiation sterilisation include X-rays, gamma and beta rays, UV light and subatomic particles; chemical sterilisation include using ethylene oxide gas, ozone, chlorine bleach, glutaraldehyde, formaldehyde, ortho phthalaldehyde, hydrogen peroxide and peracetic acid.

In one embodiment, the dry composition is sterilised by irradiation, e.g. ionizing irradiation, so as to provide sterility to the composition. Such irradiation may include e-beam (beta irradiation) or gamma irradiation. The level of irradiation and conditions for sterilisation, including the time that the composition is irradiated, are those that provide sterile compositions. Sterilisation conditions are similar to those currently utilized in the preparation of haemostatic loose powders currently available. Once having the benefit of this disclosure, one skilled in the art will be able to readily determine the level of irradiation necessary to provide sterile compositions.

When thrombin or other sensitive bioactive agents are present in the dried product, sterilisation is usually performed as terminal sterilisation with about 25 kGy or less of beta or gamma irradiation.

In one embodiment, sterilisation is performed with ethylene oxide.

Sterilisation with dry heat may typically be carried out by heating the dry haemostatic composition to a temperature between 100° C. and 250° C., such as about 110° C. to about 200° C. In particular the temperature may be in the range of 110-160° C., e.g. in the range of 110-140° C., or in the range of 120-180° C., or in the range of 130-170° C., or in the range of 130-160° C., or in the range of 120-150° C. Heat sterilisation is usually not utilised when the dry composition contains thrombin, since heat treatment would inactivate the thrombin.

In one embodiment, the dry haemostatic composition is not sterilised after packaging. When the dry haemostatic composition is manufactured by aseptic production techniques, the product is already sterile when placed in the outer packaging and no further sterilisation is required. Thus, in one embodiment the present disclosure relates to a composition produced by aseptic techniques.

Medical Use

The present disclosure further relates to use of the paste obtained from the dry composition for promoting haemostasis and/or wound healing.

The paste of the present disclosure may e.g. be used in an array of surgical procedures wherein bleeding control is desired. A haemostatic paste conforms to irregular surfaces to stop bleeding fast and it is therefore useful for providing rapid haemostasis on rough or uneven surfaces where haemostatic sponges are not efficient.

Haemostatic pastes are prepared directly at the surgical site at the time of need by the medical practitioner, i.e. the doctors or nurses by addition of liquid to a container, such as a syringe, containing an amount of a biocompatible polymer. The biocompatible polymer may be pre-wetted with the liquid or be essentially dry (free-flowing powder). The paste is thus often prepared under extremely stressful conditions and it is therefore essential that the process for preparing the paste is simple and fast to ensure that the bleeding is arrested as quickly as possible and that no mistakes are made while preparing the paste such that the nurse can keep focus on the needs of the surgeon instead of on preparing the haemostat. It is also important that the consistency of the paste is suitable for use as a haemostatic paste and that the consistency of the product is independent from preparation to preparation and over time.

Currently available flowable paste products (Floseal® and Surgiflo®) require mechanical mixing by passing the biocompatible polymer and the liquid between two connected syringes a number of times to obtain a substantially homogenous paste. Such products are often pre-prepared in the OR before surgery in case they are needed under surgery and unused product is often discarded causing unnecessary high OR costs.

The paste of the present disclosure is superior to the currently available flowable products as it reduces or obviates the need for mechanical mixing steps. The paste of the present disclosure may be prepared simply by adding an amount of an aqueous medium to a container comprising the dry composition, whereupon a ready-to-use haemostatic paste forms spontaneously, i.e. within less than about 30 seconds, preferably within less than about 20 seconds, more preferred within less than about 10 seconds, even more preferred within less than about 5 seconds, such as less than about 3 seconds or even less than about 2 seconds. When the dry composition of the present invention is contained within a medical delivery device under vacuum as described herein, the aqueous medium is automatically drawn into the product chamber due to the pressure difference and the dry composition reconstitutes spontaneously to a ready-to-use flowable composition. The flowable paste can be extruded from the medical delivery device and applied to a patient, e.g. to a bleeding wound, within seconds of coming into contact with the aqueous medium.

The quantity of liquid to be added to the dry composition may be adjusted by the skilled person. The paste so formed usually has an optimal consistency when the correct amount of liquid is added. This is not always the case with the conventional pastes, where the consistency of the paste may depend on the force applied and time spent mixing. That no mechanical mixing is required also means that less time is spent preparing the paste, which in turn leads to increased patient safety, both due to the fact that the haemostatic paste can be applied to the patient faster and that the simple preparation method decreases the likelihood of mistakes being made during the preparation of the haemostatic paste. Also, the dry composition of the present disclosure can decrease Operation Room costs as there is no need to pre-prepare the current product before surgery since preparation is so simple and fast.

When thrombin is comprised within the dry composition, the invention further has the advantage over conventional pastes in that it avoids the time-consuming and error-prone thrombin dilution and addition steps involved in current methods for preparing flowables.

Another notable advantage of the dry composition of the present invention is that a kit consisting of fewer components can be prepared as compared to e.g. current haemostatic flowable kits. All there is required to prepare a flowable paste composition in the OR is the dry composition as described herein comprised within a medical delivery device and a container comprising an aqueous medium for reconstitution. Upon connection of the two, a ready-to-use flowable paste containing all necessary agents for effective haemostasis including thrombin is formed spontaneously when the aqueous medium is automatically drawn into the vacuum expanded dry composition. Thus, no extra syringes, vial adapters, needles and mixing bowls are required with the product prepared according to the methods of the present disclosure. This means that the manufacturing costs can be decreased and also ensures good patient safety, since there are less components for the OR staff to keep track of during surgery. Needle-free preparation of the haemostat also ensures the safety of the OR staff.

In one embodiment the present disclosure relates to a method for arresting bleeding/promoting haemostasis in an individual in need thereof by application of the reconstituted paste of the present disclosure to a site of bleeding.

The paste of the present disclosure may be used for any type of surgery including general surgery, cardiothoracic surgery, vascular surgery, plastic surgery, paediatric surgery, colorectal surgery, transplant surgery, surgical oncology, trauma surgery, endocrine surgery, breast surgery, skin surgery, otolaryngology, gynaecology, oral and maxillofacial surgery, dental Surgery, orthopaedic surgery, neurosurgery, ophthalmology, podiatric surgery, urology.

In one embodiment the present disclosure relates to a method for promoting wound healing in an individual in need thereof by application of the paste of the present disclosure to the wound.

A "wound" refers broadly to injuries to the skin and/or underlying (subcutaneous) tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The present disclosure relates to treatment of any type of wound mentioned above using the paste of the present disclosure.

The treatment of a wound can in principle result in healing of the wound or in accelerated healing of the wound. The accelerated healing can be a result of e.g. administration of a wound-healing promoting substance. Alternatively, the wound healing can be promoted by preventing bacterial or viral infection, or by reducing the risk of such an infection which would otherwise have prolonged the wound treatment process.

In one embodiment the present disclosure relates to a method for promoting bone and/or tendon healing in an individual in need thereof by application of the paste of the present disclosure to the injured bone/tendon.

The "individual" referred to herein may be any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In one embodiment the present disclosure relates to a vacuum expanded, freeze-dried paste, such as the presently disclosed dry composition, for use in the treatment of a wound, e.g. for arresting bleeding or for promoting wound healing.

A Haemostatic Kit

The present disclosure further relates to a haemostatic kit comprising the dry composition of the present disclosure and an amount of aqueous medium matched to the amount of the dry composition so that upon addition of the aqueous medium, a haemostatic paste of a consistency suitable for use as a haemostatic paste will form spontaneously, i.e. within seconds.

Hence, in one embodiment the present disclosure relates to a haemostatic kit comprising:
  a) a first container comprising the dry composition obtained by the method of the present disclosure,
  b) a second container comprising an aqueous medium, and
  c) optionally an outer packaging.

In a further embodiment the present disclosure relates to a haemostatic kit comprising:
  a) the presently disclosed syringe comprising a dry composition
  b) a container comprising an aqueous medium, and
  c) optionally an outer packaging.

The dry composition may be any dry composition, in particular a dry composition that upon addition of the aqueous medium, a haemostatic paste will form of a consistency suitable for use as a haemostatic paste, such as form spontaneously within seconds, such as a dry composition obtained by the method of the present disclosure.

The aqueous medium used to reconstitute the paste may e.g. be selected from water, saline, a calcium chloride solution or a buffered aqueous solution.

In one embodiment, the aqueous medium used to reconstitute the dry composition is water. Preferably, the isotonicity of the aqueous medium is selected so that an isotonic paste will form upon addition of the aqueous medium to the dry composition.

In one embodiment, the aqueous medium used to reconstitute the dry composition is saline or a calcium chloride solution.

In one embodiment, the dry composition comprises thrombin.

In one embodiment, the kit further comprises one or more applicator tips.

The kit may optionally contain instructions for use of the kit.

EXAMPLE 1

Materials
50 g Gelatine powder (milled cross-linked gelatine sponges)
200 ml buffer
xg Polyol
50% Benzalkoniumchloride (BAC)
0.9% Saline solution
Equipment
Freeze dryer: Christ Alpha 1-4 LSC
Mixer: Kenwood, Major KM616
Method
Buffer Solution:
Add 2.0 g±0.1 g BAC (50%) to a 250 mL blue cap bottle
Add 98.0 g±0.5 g water to the BAC
Mix for 2 minutes using magnetic stirring—this is the BAC stock solution
Add 10 g±0.5 g BAC stock solution
Add water to the 2000 mL mark
Place a stopper in the flask and turn it upside down a few times
Mix by magnetic stirring for 5±1 minutes
Paste:
Dissolve xg polyol in 200 ml buffer solution under stirring in the mixer. Add 50 g gelatine powder and mix with the dissolved polyol until a homogeneous paste is obtained, approximately 5 minutes.
Freeze-Drying:
The resulting paste was filled into 10 ml single use plastic syringes (5.5 ml per syringe) comprising a lyophilisation bypass channel and placed at −30° C. for minimum 4 h. The frozen paste was transferred to the freeze-dryer and freeze-dried until dry for approximately 15 h. At the end of the drying cycle the shelves of the lyophiliser were collapsed, thereby moving the plunger and closing the lyo bypass channel. The pressure in the lyophiliser chamber was then brought to ambient pressure leaving a vacuum in the product chamber.
Reconstitution:
The dry haemostatic composition was reconstituted by connecting the syringe comprising the dry composition to a collapsible plastic bag containing water (8 ml). No mechanical mixing or stirring was used. The water was added to the dry composition by utilising the vacuum inside the product chamber, and the composition was left untouched until a paste was re-formed. The vacuum inside the product chamber of the syringe causes the water to be automatically drawn into the syringe from the container holding the water.
Results The different formulations were tested for time to reconstitution, i.e. the time needed for a paste suitable for haemostatic purposes to spontaneously form without mechanical agitation of any sorts.

Pastes comprising different polyols were made, dried and reconstituted according to the directions above. The contents of the pastes are shown in the tables below.

|  | Content wet [g] | Content dry [g] | Content wet [W/W %] | Content dry [W/W %] |
|---|---|---|---|---|
| Gelatine | 50.00 | 50.00 | 18.52 | 70.41 |
| Mannitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Xylitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Trehalose | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Maltitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Sorbitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

The polyol:gelatine ratio in the dry compositions was approximately 0.4:1.

The spontaneous reconstitution time of the pastes comprising different polyols made according to the tables above is shown in the table below and in FIG. 1. The experiments were repeated 5 times for each polyol.

|   | Mannitol | Xylitol | Trehalose | Maltitol | Sorbitol |
|---|---|---|---|---|---|
| 1 | 7 | 14 | 11 | 14 | 29 |
| 2 | 9 | 31 | 28 | 14 | 28 |
| 3 | 9 | 20 | 16 | 23 | 29 |
| 4 | 10 | 30 | 29 | 16 | 35 |
| 5 | 9 | 31 | 23 | 22 | 32 |
| Average reconstitution time [sec] | 8.8 | 25.2 | 21.4 | 17.8 | 30.6 |
| Std | 1.1 | 7.8 | 7.8 | 4.4 | 2.9 |

The experiment shows that different kinds of polyols can be used for making a freeze-dried gelatine paste that will reconstitute spontaneously upon addition of an aqueous medium within less than about 30 seconds. The reconstituted paste has a consistency suitable for direct use as a haemostatic paste.

EXAMPLE 2

Thrombin

Thrombin was included in the below paste formulation at a theoretical concentration of 2500 IU/product. The paste was made at room temperature (about 20° C.) and mixed as described in Example 1.

The dried paste had a spontaneous reconstitution time of about 5 seconds. The contents of the paste formulation are specified in the table below in the paste (wet) and the dried composition (dry) respectively.

| Paste Formulation | Content wet [g] | Content dry [g] | Content wet [%] | Content dry [%] |
|---|---|---|---|---|
| Gelatine | 50.00 | 50.00 | 18.18 | 56.65 |
| Mannitol | 20.00 | 20.00 | 7.27 | 22.66 |
| Glycerol (buffer) | 12.30 | 12.30 | 4.47 | 13.94 |
| Glycerol (added) | 5.00 | 5.00 | 1.82 | 5.67 |
| BAC | 0.01 | 0.01 | 0.00 | 0.01 |
| NaCl | 0.01 | 0.01 | 0.00 | 0.01 |
| $H_2O$ | 187.68 | 0.94 | 68.25 | 1.06 |
| SUM | 275.00 | 88.26 | 100 | 100 |

The total polyol concentration, i.e. mannitol and glycerol, in the paste was 13.56% and after drying 42.27%.

The polyol:gelatine ratio in the dry composition was approximately 0.75:1.

The paste was dried by freeze-drying and reconstituted as described in Example 1.

The thrombin activity was measured in the reconstituted paste. The results are shown in the table below.

| Thrombin Activity - Freeze-dried composition in syringe [IU/product] | | |
|---|---|---|
| 2519.60 | 2884.94 | 2796.71 |
| | Mean activity: 2733.75 | |

No loss of thrombin activity was measured in the reconstituted paste.

The results show that it is not strictly necessary to perform the mixing of the paste at low temperatures to avoid loss of thrombin activity as no decrease in thrombin activity was found when mixing was performed at ambient temperatures.

EXAMPLE 3

Vacuum Expansion of Pastes Prior to Freeze-Drying

Gelatine pastes comprising mannitol were prepared essentially as described in Example 1 and aliquoted into 10 ml single-use syringes, each syringe receiving 4 g of the paste. The contents of the paste formulation are specified in the table below in the paste (wet) and the dried composition (dry) respectively.

|   | Content wet [g] | Content dry [g] | Content wet [W/W %] | Content dry [W/W %] |
|---|---|---|---|---|
| Gelatine | 50.00 | 50.00 | 18.52 | 70.41 |
| Mannitol | 20.00 | 20.00 | 7.41 | 28.17 |
| BAC | 0.01 | 0.01 | 0.00 | 0.01 |
| $H_2O$ | 200 | 1.00 | 74.07 | 1.41 |
| SUM | 270.01 | 71.01 | 100 | 100 |

The prepared pastes were either freeze dried directly as described in Example 1 (standard lyophilisation) or subjected to a low vacuum of about 850 mbar, followed by a freezing step to −40° C. without releasing the vacuum and finally freeze dried essentially as described in Example 1 (vacuum expanded lyophilisation). Vacuum expansion was performed at ambient temperature, i.e. about 20° C. Upon exposure of the pastes to the decreased pressure, i.e. vacuum, the pastes expanded in volume almost instantaneously.

Before vacuum expansion, the density of the gelatine paste was approximately about 0.7 g/ml. After vacuum expansion, the density of the paste was approximately about 0.5 g/ml corresponding to a decrease in the density of the paste by about a factor 0.72 and a concurrent increase in the volume of the paste by about a factor 1.4.

The lyophilised products were reconstituted essentially as described in Example 1 by adding 5.5 ml saline to the lyophilised product and the amount of time for the paste to fully absorb the saline was measured. The vacuum inside the product chamber of the syringes automatically draws in the liquid. Both vacuum expanded and standard pastes were soft and moist after reconstitution and exhibited comparable absorption capacities. The consistency of the reconstituted pastes was considered suitable for direct use on a patient. The reconstituted pastes had a slightly off white/yellowish colour.

Figure 2:
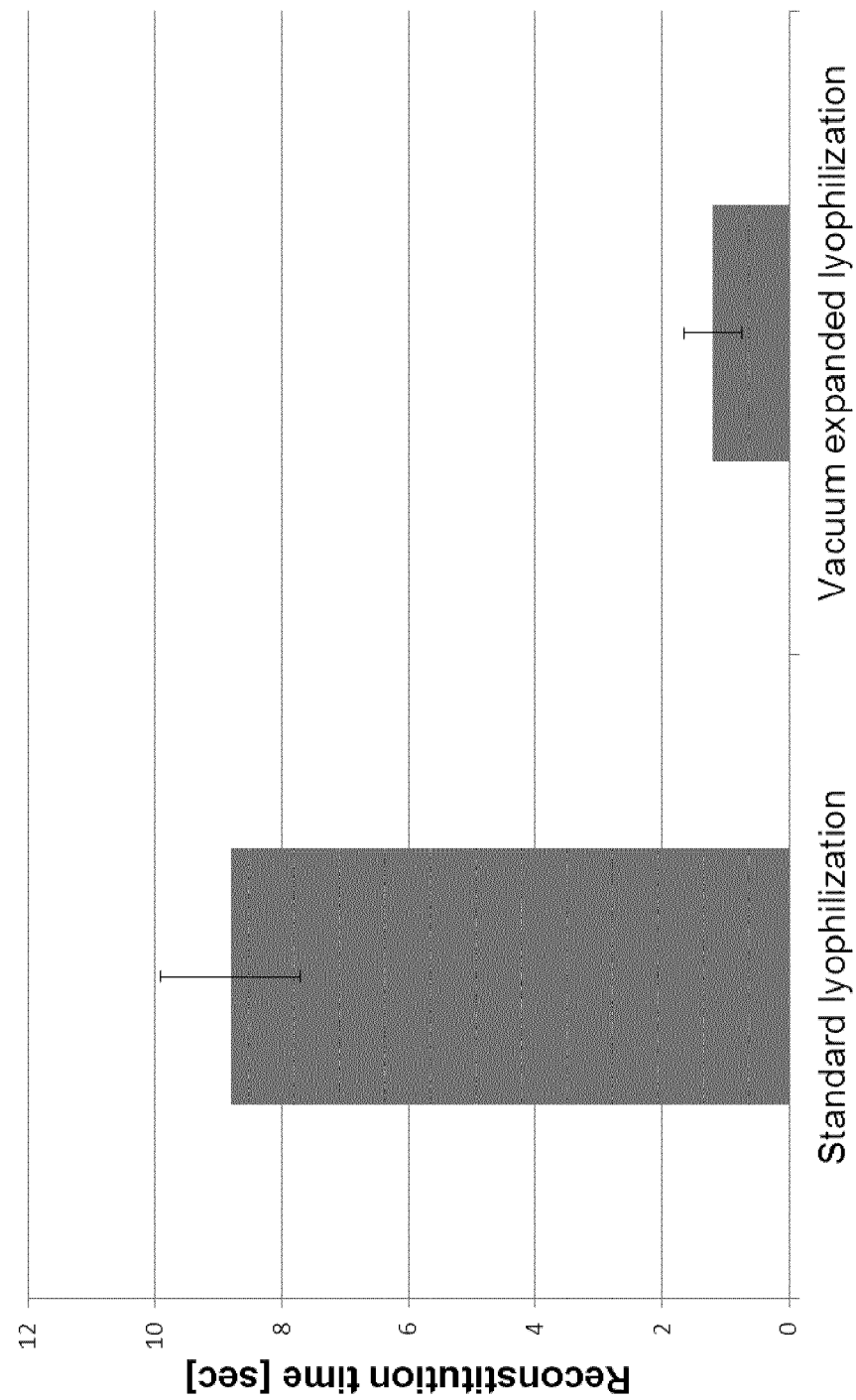
FIG. 2. Average reconstitution time+/−standard deviation of the standard lyophilised and vacuum expanded lyophilised gelatine pastes of example 3. Vacuum expansion greatly decreased the spontaneous reconstitution time of pastes comprising mannitol.
Figure 3:
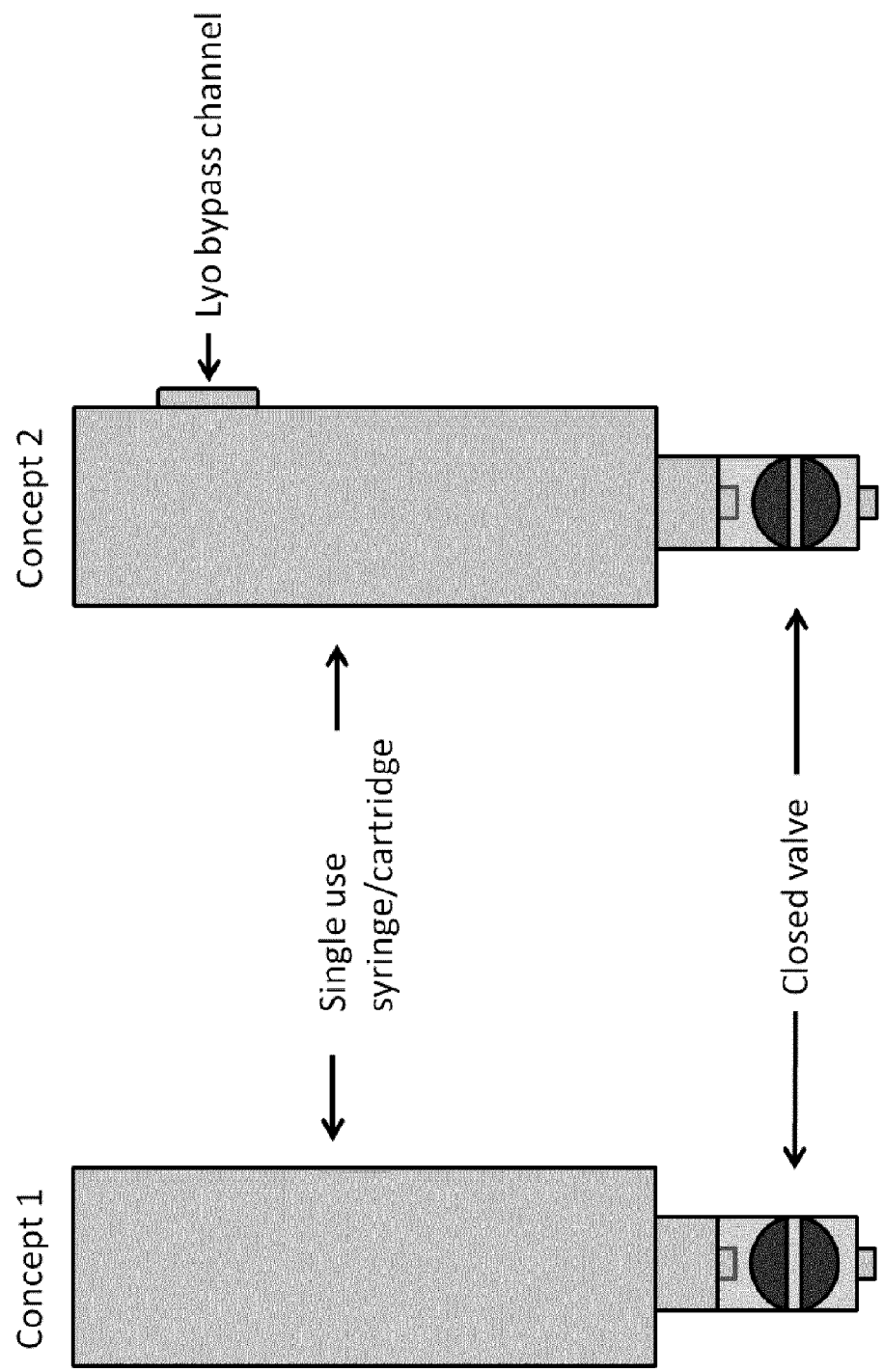
FIGS. 3 to 14 depict different embodiments and stages of the method of the present disclosure.
Figure 4:
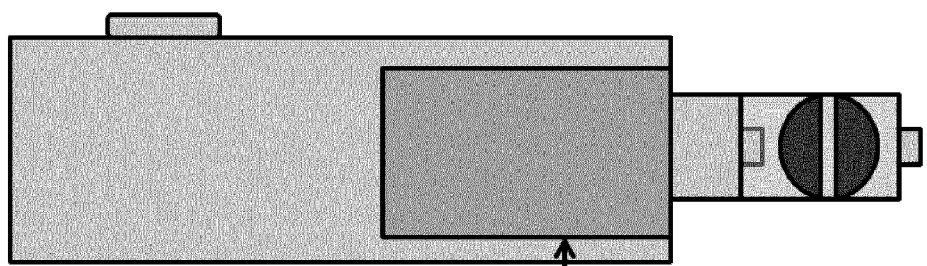
Figure 4:
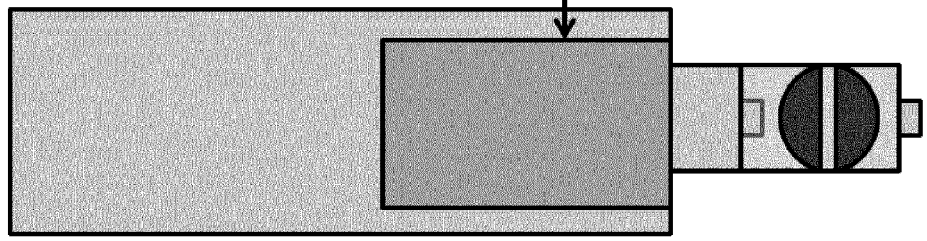

The reconstitution time for the dried paste compositions is shown in the below table and in FIG. 2. The experiments were repeated 5 times (n=5).

| n | Standard lyophilization | Vacuum expanded lyophilization |
|---|---|---|
| 1 | 7 | 1 |
| 2 | 9 | 2 |
| 3 | 9 | 1 |
| 4 | 10 | 1 |
| 5 | 9 | 1 |

| n | Standard lyophilization | Vacuum expanded lyophilization |
|---|---|---|
| Average reconstitution time [sec] | 8.8 | 1.2 |
| Std | 1.1 | 0.4 |

The inventors surprisingly found that by subjecting the paste to vacuum prior to freezing, the haemostatic dried paste reconstituted more than seven times faster than pastes that had not been vacuum expanded. Reconstitution required no mechanical agitation, mixing or stirring of any kind and a ready-to-use haemostatic paste of a consistency suitable for direct use in haemostatic procedures was formed within seconds.

EXAMPLE 4

Density of Dry Vacuum Expanded Paste

Gelatine pastes comprising mannitol were prepared as described in Examples 1 and 3. The pastes were vacuum expanded using different vacuum levels (1000 mbar (no vacuum), 850 mbar and 600 mbar) and then frozen and freeze-dried as described in Example 3.

Figure 15:
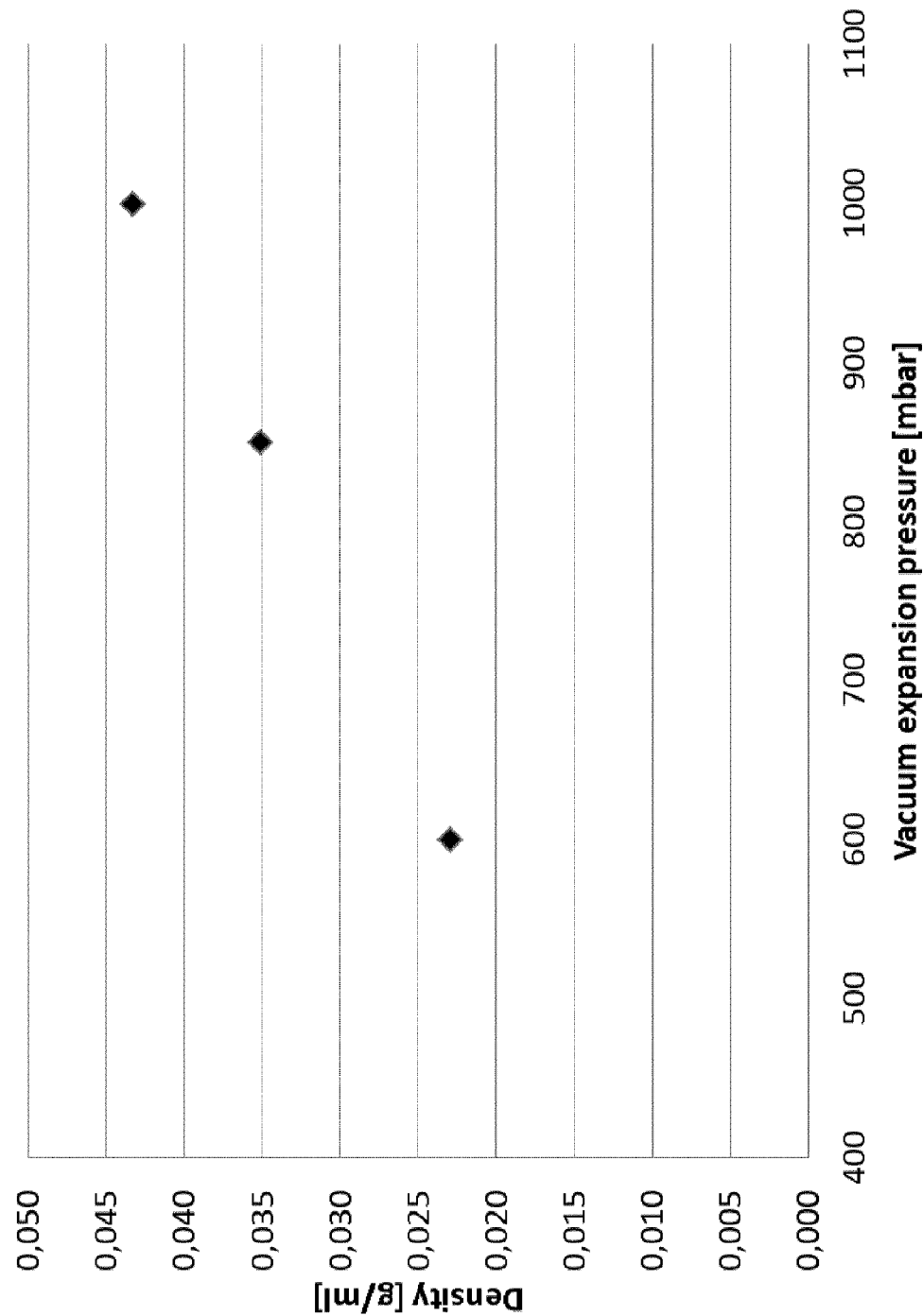
FIG. 15 shows a correlation between the pressure used for vacuum expanding a gelatine paste and the density of the final dry paste composition: The lower the pressure; the lower the density of the dry composition.
Figure 16A:
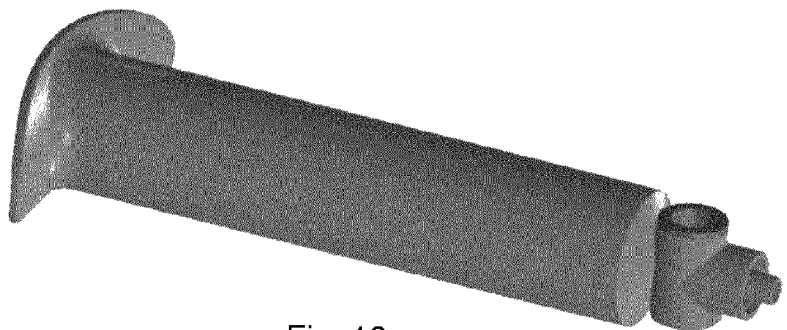
FIGS. 16a-d show perspective views of the barrel of one embodiment of the presently disclosed syringe.
Figure 16C:
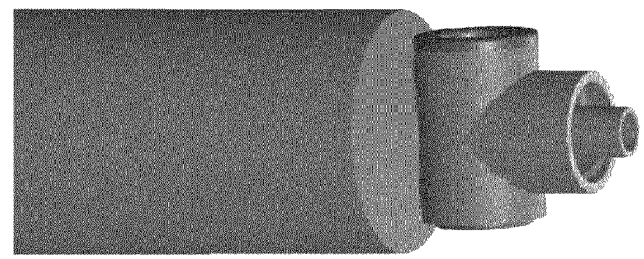
Figure 16B:
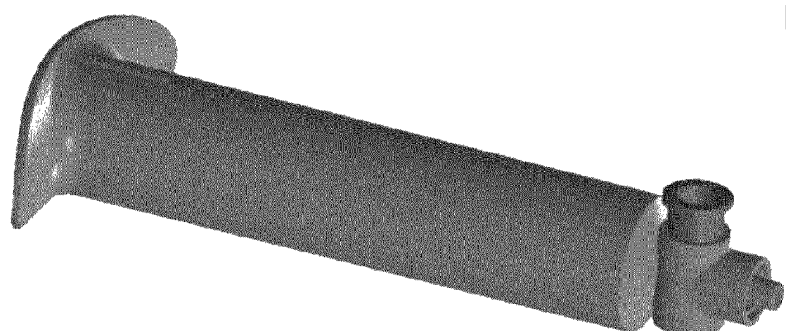
Figure 16D:
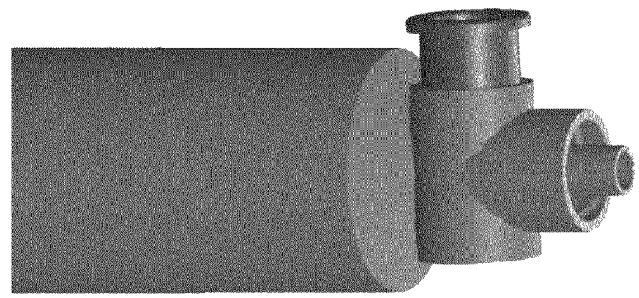

The density of the dry paste compositions is shown in the below table and in FIG. 15.

| Pressure [mbar] | Ø [cm] | H [cm] | Mass [g] | Volume [cm³] | Density [g/cm³] |
|---|---|---|---|---|---|
| 1000 | 1.4 | 4.9 | 1.3 | 30.2 | 0.043 |
| 850 | 1.5 | 5.5 | 1.4 | 38.9 | 0.035 |
| 600 | 1.8 | 6.0 | 1.4 | 61.1 | 0.023 |

The dry compositions reconstituted spontaneously to form soft and moist pastes suitable for haemostatic and/or wound healing use.

The results show that different pressures may be used to expand the paste prior to drying.

The results further show that the pressure used for expansion affects the density of the dry paste composition. Indeed, there seems to be a good correlation between the pressure and the density of the dry composition with lower pressures resulting in lower densities of the final dry paste composition.

EXAMPLE 5

Effect of Vacuum Expansion and Polyol Concentration

Gelatine pastes comprising different amounts of mannitol (no mannitol, medium mannitol (approx. 3.9%) or high mannitol (approx. 7.4%)) were prepared essentially as described in Example 1 with the exception that a Virtis Genesis 35 freeze-dryer was used. Portions of paste were aliquoted into 10 ml single-use syringes having vacuum bypass, each syringe receiving 4 g of the paste. The contents of the paste formulation are specified in the table below in the paste (wet) and the dried composition (dry) respectively.

| | Content wet [g] | Content dry [g] | Content wet [W/W %] | Content dry [W/W %] |
|---|---|---|---|---|
| No Mannitol | | | | |
| Gelatine | 50.00 | 50.00 | 20.00 | 98.02 |
| Mannitol | 0.00 | 0.00 | 0.00 | 0.00 |
| BAC | 0.01 | 0.01 | 0.00 | 0.02 |
| H₂0 | 200.00 | 1.00 | 80.00 | 1.96 |
| SUM | 250.01 | 51.01 | 100.00 | 100.00 |
| Medium Mannitol | | | | |
| Gelatine | 50.00 | 50.00 | 19.23 | 81.95 |
| Mannitol | 10.00 | 10.00 | 3.85 | 16.39 |
| BAC | 0.01 | 0.01 | 0.00 | 0.02 |
| H₂0 | 200.00 | 1.00 | 76.92 | 1.64 |
| SUM | 260.01 | 61.01 | 100.00 | 100.00 |
| High Mannitol | | | | |
| Gelatine | 50.00 | 50.00 | 18.52 | 70.41 |
| Mannitol | 20.00 | 20.00 | 7.41 | 28.17 |
| BAC | 0.01 | 0.01 | 0.00 | 0.01 |
| H₂0 | 200.00 | 1.00 | 74.07 | 1.41 |
| SUM | 270.01 | 71.01 | 100.00 | 100.00 |

The prepared pastes were either freeze dried directly as described in Example 1 (no expansion) or vacuum expanded by exposure to a low vacuum of about 850 mbar, followed by a freezing step to −40° C. without releasing the vacuum and finally freeze dried essentially as described in Example 1 (vacuum expansion). Vacuum expansion was performed at ambient temperature, i.e. about 20° C.

The lyophilised products were reconstituted by adding 5.5 ml saline to the lyophilised product in the syringe and the amount of time for the paste to fully absorb the saline was measured. No mechanical mixing was performed. The reconstituted pastes were soft and moist and exhibited comparable absorption capacities. However, the consistency of the non-expanded gelatine pastes without mannitol were inferior to pastes containing mannitol and/or pastes having been expanded by vacuum. The reconstituted pastes had a slightly off white/yellowish colour.

Figure 21:
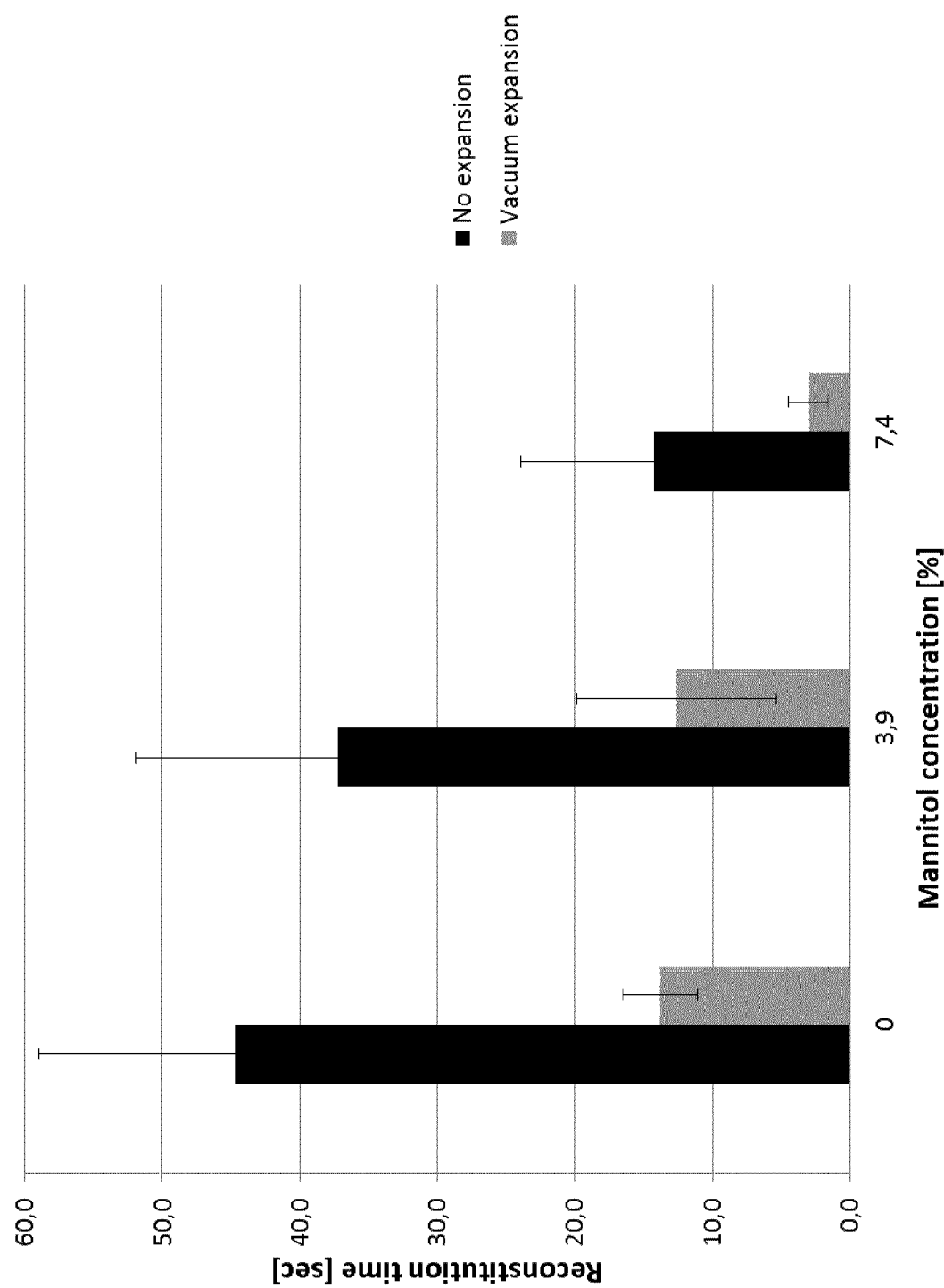
FIG. 21 shows the average reconstitution time+/−standard deviation of dried gelatine paste compositions comprising different amounts of mannitol (wt % in wet paste) with and without vacuum expansion. Vacuum expansion greatly decreased the spontaneous reconstitution time of the dried pastes, which is even further decreased by increasing concentrations of mannitol in the dried pastes.

The average reconstitution time for the dried paste compositions is shown in the below table and in FIG. 21. Each experiment was repeated 5 times (n=5).

| | Mannitol concentration [wt %] | Average reconstitution time in seconds +/− standard deviation |
|---|---|---|
| No expansion | 0 | 44.8 +/− 14.2* |
| No expansion | 3.9 | 37.2 +/− 14.7 |
| No expansion | 7.4 | 14.3 +/− 9.7 |
| Expansion | 0 | 13.8 +/− 2.7 |
| Expansion | 3.9 | 12.6 +/− 7.2 |
| Expansion | 7.4 | 3.0 +/− 1.4 |

*The consistency of the reconstituted paste was clearly inferior to pastes containing mannitol and/or pastes having been expanded by vacuum.

Vacuum expansion of the gelatine pastes prior to freeze-drying greatly reduced the reconstitution time of dried gelatine paste compositions both with and without mannitol. In fact, vacuum expansion was able to reduce the spontaneous reconstitution time of the gelatine pastes with about a factor 3 or more. The spontaneous reconstitution time was further improved, i.e. decreased, by inclusion of mannitol in the dry compositions. Mannitol also improved the consistency of the reconstituted pastes.

Gelatine pastes containing 7.4% polyethylene glycol (PEG) were also prepared as above, vacuum expanded and freeze-dried. The contents of the paste formulation are specified in the table below in the paste (wet) and the dried composition (dry) respectively.

| PEG | Content wet [g] | Content dry [g] | Content wet [W/W %] | Content dry [W/W %] |
|---|---|---|---|---|
| Gelatine | 50.00 | 50.00 | 18.52 | 70.41 |
| PEG | 20.00 | 20.00 | 7.41 | 28.17 |
| BAC | 0.01 | 0.01 | 0.00 | 0.01 |
| H$_2$0 | 200.00 | 1.00 | 74.07 | 1.41 |
| SUM | 270.01 | 71.01 | 100.00 | 100.00 |

Figure 22:
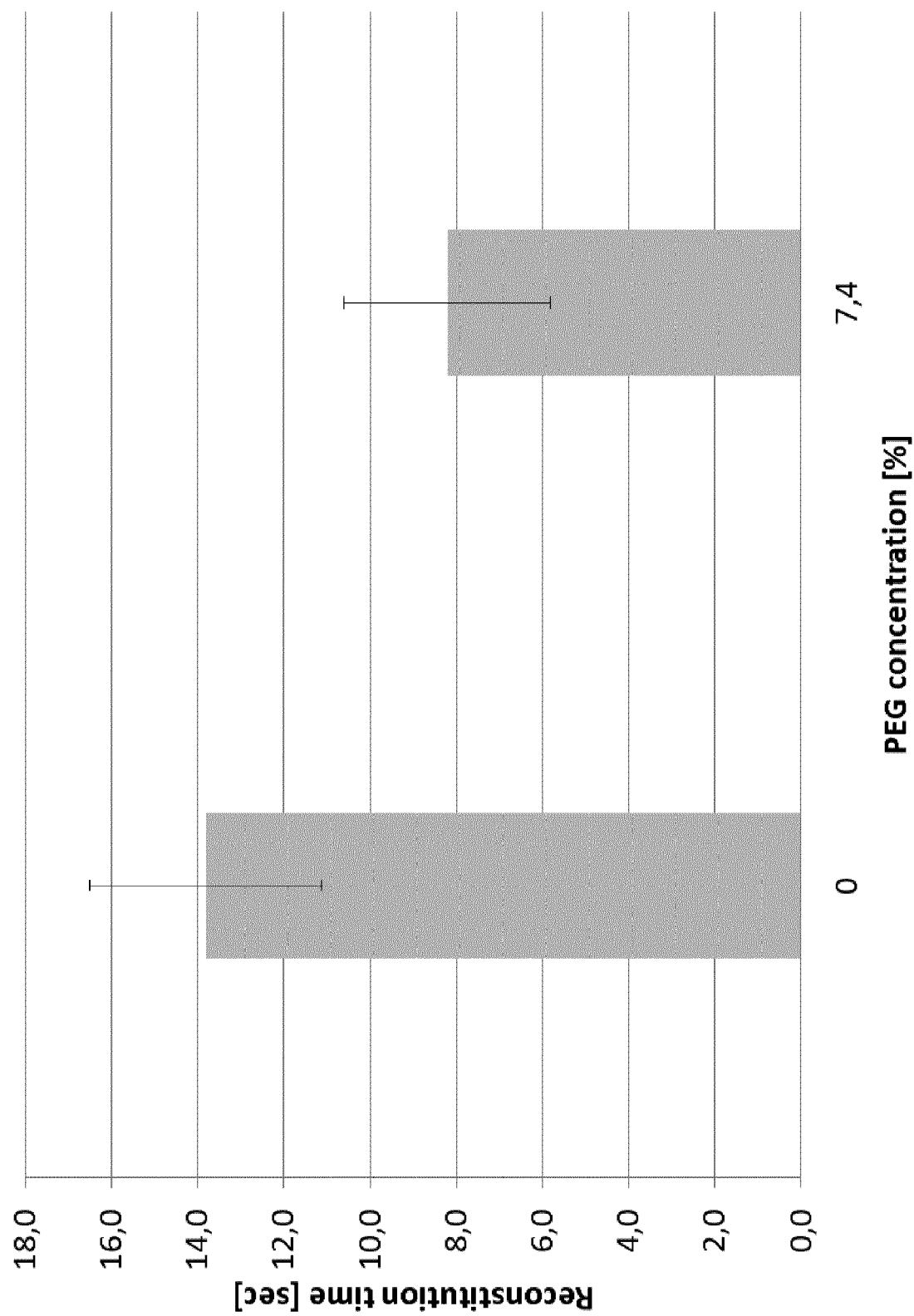
FIG. 22 shows the reconstitution time+/−standard deviation of vacuum expanded dried gelatine paste compositions with and without PEG (wt % in wet paste). PEG decreased the reconstitution time as compared to vacuum expanded compositions without PEG.

The average reconstitution time for the dried paste compositions comprising PEG was 8.2+/−2.4 seconds (n=5). Dried vacuum-expanded gelatine pastes containing PEG reconstituted about 1.7 times faster than control (vacuum expanded gelatine paste without any hydrophilic compounds added) and had a superior consistency. The results are shown in FIG. 22.

The inventors have also discovered that the volume of a paste aliquot is generally higher in samples being aliquoted first as opposed to last from a single batch of paste.

This is thought to be due to a partial collapse of the paste over time causing undesirable variations in paste density. Such variations in density can lead to undesirable variations in the reconstitution time. Vacuum expansion of the paste prior to drying is believed to be able to reduce or even eliminate such differences in paste density which can occur between the first and the last portions of pastes being aliquoted from a single paste batch.

In conclusion, the results show that vacuum expansion before drying greatly improves the reconstitution rate and is able to provide more consistent results with regards to the reconstitution time. The spontaneous reconstitution rate can be further improved by inclusion of increasing amounts of polyols in the dried paste compositions. In addition, inclusion of hydrophilic compounds, such as polyols, in the dried paste compositions also improved the consistency of the reconstituted pastes.

Further Details of the Present Disclosure

Further details of the present disclosure are provided in the following items:

1. A method for preparing a dry composition comprising the sequential steps of:
   a. providing an agent in powder form and an aqueous medium,
   b. mixing the agent in powder form and the aqueous medium to obtain a paste,
   c. subjecting the paste to a reduced pressure thereby expanding the paste,
   d. freezing the expanded paste, and
   e. drying the paste.
2. The method according to item 1, wherein the reduced pressure is a pressure of at least 50 mbar less than ambient pressure, such as at least 100 mbar less than ambient pressure, for example at least 150 mbar less than ambient pressure, such as at least 200 mbar less than ambient pressure, for example at least 250 mbar less than ambient pressure, such as at least 300 mbar less than ambient pressure, for example at least 350 mbar less than ambient pressure, such as at least 400 mbar less than ambient pressure, for example at least 450 mbar less ambient pressure, such as at least 500 mbar less than ambient pressure, for example at least 550 mbar less ambient pressure, such as at least 600 mbar less than ambient pressure, for example at least 650 mbar less than ambient pressure, such as at least 700 mbar less than ambient pressure, for example at least 750 mbar less than ambient pressure, such as at least 800 mbar less than ambient pressure, for example at least 850 mbar less than ambient pressure, such as at least 900 mbar less ambient pressure.
3. The method according to any of the preceding items, wherein the volume of the paste is increased by about a factor 1.05 to about a factor 2.0, such as about a factor 1.1 to about a factor 1.8, for example about a factor 1.2 to about a factor 1.6 as a result of the reduced pressure.
4. The method according to any of the preceding items, wherein the density of the paste is decreased by at least a factor 0.95 as a result of the vacuum expansion, such as at least a factor 0.90, for example at least a factor 0.85, such as at least a factor 0.80, for example at least a factor 0.75, such as at least a factor 0.70, for example at least a factor 0.65, such as at least a factor 0.60, for example at least a factor 0.55, such as at least a factor 0.50 as a result of the vacuum expansion.
5. The method according to any of the preceding items, wherein the agent in powder form is a biocompatible polymer.
6. The method according to any of the preceding items, wherein the agent in powder form is cross-linked.
7. The method according to any of the preceding items, wherein the agent in powder form is biologically absorbable.
8. The method according to any of the preceding items, wherein the agent in powder form is gelatine.
9. The method according to any of the preceding items, wherein the drying is freeze-drying.
10. The method according to any of the preceding items, wherein the drying results in a dry composition comprising less than about 5% water, preferably less than about 2% water.
11. The method according to any of the preceding items, wherein the agent in powder form and the aqueous medium is mixed with one or more hydrophilic compounds.
12. The method according to item 11, wherein the paste prior to drying comprises from about 2% to about 40% of one or more hydrophilic compounds, for example from about 2% to about 30% of one or more hydrophilic compounds, such as from about 2% to about 25% of one or more hydrophilic compounds, for example from about 2% to about 20% of one or more hydrophilic compounds, such as from about 2% to about 18% of one or more hydrophilic compounds, for example from about 2% to about 17% of one or more hydrophilic compounds, such as from about 2% to about 16% of one or more hydrophilic compounds, for example from about 2% to about 15% of one or more hydrophilic compounds.
13. The method according to any of items 11 to 12, wherein the paste prior to drying comprises:
   a. from about 2% to about 40% of one or more hydrophilic compounds,
   b. from about 10% to about 60% of the agent in powder form, and
   c. from about 50% to about 90% of water.
14. The method according to any of items 11 to 12, wherein the paste prior to drying comprises:
   a. from about 5% to about 20% of one or more hydrophilic compounds, b. from about 15% to about 25% of the agent in powder form, and
c. from about 60% to about 80% of water.

15. The method according to any of items 11 to 14, wherein the one or more hydrophilic compounds are one or more polyols.
16. The method according to item 15, wherein the one or more polyols is selected from sugar alcohols, sugars and/or derivatives thereof.
17. The method according to item 16, wherein the one or more sugar alcohols is selected from the group consisting of glycol, glycerol, erythritol, threitol, arabitol, xylitol, ribitol, mannitol, sorbitol, dulcitol, fucitol, iditol, inositol, volemitol, isomalt, maltitol, lactitol and polyglycitol.
18. The method according to any items 15 to 17, wherein the one or more polyols is mannitol and optionally one or more further hydrophilic compounds.
19. The method according to any of the preceding items, wherein the dry composition further comprises one or more bioactive agents capable of stimulating haemostasis, wound healing, bone healing, tissue healing and/or tendon healing.
20. The method according to item 19, wherein the bioactive agent is thrombin.
21. The method according to any of the preceding items, wherein the aqueous medium is selected from the group consisting of water, saline, a calcium chloride solution and a buffered aqueous medium.
22. The method according to any of the preceding items, wherein the method comprises a further step of placing the dry composition into an outer packaging, such as an aluminium foil packaging.
23. The method according to any of the preceding items, wherein the method comprises a further step of sterilising the dry composition.
24. The method according to any of the preceding items, wherein the dry composition reconstitutes without mechanical mixing to form a ready-to-use paste within less than about 30 seconds, preferably within less than about 20 seconds, more preferred within less than about 10 seconds, even more preferred within less than about 5 seconds, such as less than about 3 seconds, for example less than about 2 seconds.
25. A wet paste composition being a vacuum expanded wet paste having a density of between about 0.2 g/ml to about 0.6 g/ml, more preferred between about 0.3 g/ml to about 0.6 g/ml, such as between about 0.4 g/ml to about 0.5 g/ml.
26. A dry composition obtainable by the method of any of items 1 to 24.
27. A dry composition being a vacuum expanded, freeze-dried paste with a density of between about 1 mg/ml to about 40 mg/ml, such as between about 5 mg/ml to about 35 mg/ml, for example between about 10 mg/ml to about 35 mg/ml.
28. A syringe for retaining a freeze-dried paste in a vacuum comprising
   a barrel comprising
      a vacuum chamber for containing the paste having an open proximal end and a distal end having a first fluid opening,
      a connector portion having a second fluid opening and adapted for connection to a liquid receptacle, and
      a pressure chamber connecting the connector portion and the distal end of the vacuum chamber,
   a pressure valve located in the pressure chamber and adapted to seal the first and second fluid openings in a first position and form/create a fluid passageway between the first and second fluid openings in a second position,
   a plunger configured to be axially displaced in the vacuum chamber through the open proximal end, and
   one or more vacuum bypass channels.
29. The syringe according to any of preceding items 28, wherein the barrel comprises a flange at the proximal end of the vacuum chamber.
30. The syringe according to any of preceding items 28 to 29, wherein the syringe is adapted to retain the dry composition according to item 26.
31. The syringe according to any of preceding items 28 to 30, wherein the freeze dried paste is obtained by the method according to any of items 1 to 24.
32. The syringe according to any of preceding items 28 to 31, wherein the connector portion is a Luer lock or Luer slip connector, preferably a male Luer lock or Luer slip connector.
33. The syringe according to any of preceding items 28 to 32, wherein the connector portion comprises a threaded portion.
34. The syringe according to any of preceding items 28 to 33, wherein the pressure valve is located in the pressure chamber and adapted to seal the first and second fluid openings in a first position in the pressure chamber and form/create a fluid passageway between the first and second fluid openings in a second position in the pressure chamber.
35. The syringe according to any of preceding items 28 to 34, wherein the pressure chamber is located between the vacuum chamber and the second fluid opening.
36. The syringe according to any of preceding items 28 to 35, wherein the pressure chamber comprises a proximal end abutting the distal end of the vacuum chamber and a distal end abutting a proximal end of the connector portion.
37. The syringe according to any of preceding items 28 to 36, wherein the connector portion comprises a proximal end abutting a distal end of the pressure chamber and a distal end adapted for connection to a liquid receptacle.
38. The syringe according to any of preceding items 28 to 37, wherein the second fluid opening forms an elongated channel through the connector portion.
39. The syringe according to any of preceding items 28 to 38, wherein the second fluid opening comprises a proximal end abutting a distal end of the pressure chamber and a distal end for inlet and outlet of fluid.
40. The syringe according to any of preceding items 28 to 39, wherein the pressure valve is adapted to seal a distal end of the first fluid opening and a proximal end of the second fluid opening in said first position.
41. The syringe according to any of preceding items 28 to 33, wherein the inside of the pressure chamber is cylindrical.
42. The syringe according to any of preceding items 28 to 41, wherein the pressure valve comprises a groove, and wherein the groove forms the fluid passageway in the second position of the pressure valve.
43. The syringe according to any of preceding items 28 to 42, wherein the pressure valve comprises two cylindrical sections axially divided by a groove, and wherein the groove forms the fluid passageway in the second position of the pressure valve.

44. The syringe according to any of preceding items 28 to 43, wherein the first and second positions of the pressure valve are radially displaced with respect to the longitudinal axis of the syringe.
45. The syringe according to any of preceding items 28 to 44, wherein the pressure valve protrudes from the pressure chamber in said first position.
46. The syringe according to any of preceding items 28 to 45, wherein the pressure valve is flush with and/or abuts the pressure chamber in said second position.
47. The syringe according to any of preceding items 28 to 46, wherein the pressure valve comprises a valve flange at an end of the pressure valve protruding from the pressure chamber and wherein said valve flange protrudes from the pressure chamber in said first position, and wherein said valve flange is flush with and/or abuts the pressure chamber in said second position.
48. The syringe according to any of preceding items 28 to 47, wherein the first and second positions of the pressure valve are rotatably displaced.
49. The syringe according to any of preceding items 28 to 48, wherein the pressure valve comprises a through-going channel forming the fluid passageway in the second position of the pressure valve.
50. The syringe according to any of preceding items 28 to 49, wherein the pressure valve comprises a cylindrical section with a through-going radial channel forming the fluid passageway in the second position of the pressure valve.
51. The syringe according to any of preceding items 28 to 50, wherein the pressure valve and the pressure chamber is configured such that the second position of the pressure valve is a locked position.
52. The syringe according to any of preceding items 28 to 51, wherein the pressure valve and the pressure chamber is configured such that the pressure valve is axially locked in the second position of the pressure valve.
53. The syringe according to any of preceding items 28 to 52, wherein the pressure valve and the pressure chamber is configured such that the pressure valve is rotatably locked in the second position of the pressure valve.
54. The syringe according to any of preceding items 28 to 53, wherein said one or more vacuum bypass channels are configured to provide a fluid, such as a gaseous, communication between the vacuum chamber and the ambient atmosphere.
55. The syringe according to any of preceding items 28 to 54, wherein the syringe is configured such that the plunger sealably engages the vacuum chamber in at least a first axial position of the plunger inside the vacuum chamber, and such that fluid communication is established across the plunger in at least a second axial position of the plunger inside the vacuum chamber via said one or more vacuum bypass channels.
56. The syringe according to any of preceding items 28 to 55, wherein said one or more vacuum bypass channels are configured to break the sealing between the vacuum chamber and the plunger at a predefined axial position of the plunger inside the vacuum chamber.
57. The syringe according to any of preceding items 28 to 56, wherein said one or more vacuum bypass channels are formed in the vacuum chamber.
58. The syringe according to any of preceding items 28 to 57, wherein said one or more vacuum bypass channels are one or more longitudinal grooves formed in the inner surface of the proximal end of the vacuum chamber.
59. The syringe according to any of preceding items 28 to 58, wherein said one or more vacuum bypass channels are formed in the plunger.
60. The syringe according to any of preceding items 28 to 59, wherein the barrel is formed in a single piece of material.
61. The syringe according to any of preceding items 28 to 60, wherein the barrel is suitable for manufacture by means of single cycle injection molding.
62. The syringe according to any of preceding items 28 to 61, wherein the vacuum chamber, the pressure chamber and the connector portion are formed as separate elements and configured to be assembled during manufacture of the syringe.
63. The syringe according to any of preceding items 28 to 62, wherein the pressure chamber and the connector portion are formed as one element and configured to be assembled with the vacuum chamber during manufacture of the syringe.
64. The syringe according to any of preceding items 28 to 63, wherein the vacuum chamber and the pressure chamber are formed as one element and configured to be assembled with the connector portion during manufacture of the syringe.
65. The syringe according to any of preceding items 28 to 64, wherein the pressure valve comprises an aperture, and wherein the aperture forms at least a part of the fluid passageway in the second position of the pressure valve, said aperture preferably extending in the longitudinal direction of the barrel.
66. The syringe according to any of preceding items 28 to 65, wherein the pressure valve comprises one or more protrusions, preferably extending sideways, such as transverse to the fluid passageway.
67. The syringe according to any of preceding items 28 to 66, wherein the pressure valve protrudes radially and/or transversally from the pressure chamber in said first position and wherein the pressure valve is flush with or totally submerged into the pressure chamber in said second position.
68. The syringe according to any of preceding items 28 to 67, wherein the pressure valve comprises a top surface, wherein said top surface is flush with a top surface of the pressure chamber in said second position.
69. The syringe according to any of preceding items 28 to 68, wherein the pressure valve comprises a rounded top surface configured to match a rounded top surface of the pressure chamber in said second position of the pressure valve.
70. The syringe according to any of preceding items 28 to 69, wherein the pressure valve and the pressure chamber is configured such that the pressure valve is transversally and/or radially limited in said first position.
71. The syringe according to any of preceding items 28 to 70, wherein the pressure valve and the pressure chamber is configured such that the pressure valve is transversally and/or radially limited in said first position by means of one or more protrusions on the pressure valve.
72. The syringe according to any of preceding items 28 to 71, wherein an inner side wall of the pressure chamber comprises a narrowing adapted to limit transverse and/or radial displacement of the pressure valve in the first position.
73. The syringe according to any of preceding items 28 to 72, wherein the pressure valve and the pressure chamber is configured such that the pressure valve can be inserted from one side of the pressure chamber, preferably only one side of the pressure chamber.

74. A container comprising:
   a. a product chamber comprising a dry composition capable of forming a paste upon addition of an aqueous medium, wherein the pressure within the product chamber is less than the pressure outside the product chamber, and
   b. a valve.

75. The container according to item 74 being a syringe, such as a single-use plastic syringe, such as the syringe according to any of items 29 to 73.

76. A method for reconstituting a dry composition comprising the steps of:
   a. providing the container of any of items 74-75, said container being the first container,
   b. providing a second container comprising an aqueous medium, wherein the pressure within the second container is greater than the pressure within the product chamber of the first container,
   c. connecting the first container and the second container using suitable connecting means, and
   d. opening the valve.

77. A method for reconstituting a dry composition comprising the steps of:
   a. providing the syringe of any of items 29 to 73 comprising a dry composition capable of forming a paste upon addition of an aqueous medium, wherein the dry composition is located in the vacuum chamber and wherein the pressure within the vacuum chamber is less than the pressure outside the vacuum chamber, and wherein the pressure valve of the syringe is arranged in the first position,
   b. providing a second container comprising an aqueous medium,
   c. connecting the syringe and the second container via the connector portion of the syringe using suitable connecting means, and
   d. moving the pressure valve of the syringe to the second position thereby providing a fluid connection between the vacuum chamber of the syringe and the second container.

78. The method according to any of items 76 to 77, wherein the dry composition reconstitutes within less than about 30 seconds, preferably within less than about 20 seconds, more preferred within less than about 10 seconds, even more preferred within less than about 5 seconds, such as less than 3 seconds, for example less than 2 seconds.

79. The method according to any of items 76 to 78, wherein the second container comprising the aqueous medium is selected from i) a collapsible container, such as a plastic bag, and ii) a non-collapsible container comprising a plunger.

80. A haemostatic kit comprising:
   a) a syringe according to any of items 29 to 73 comprising a dry composition,
   b) a container comprising an aqueous medium, and
   c) optionally an outer packaging.

81. The haemostatic kit according to item 80, wherein the dry composition is a dry composition that is configured to form a haemostatic paste of a consistency suitable for use as a haemostatic paste upon addition of the aqueous medium, such as form spontaneously within seconds.

82. The haemostatic kit according to any of items 80 to 81, wherein the dry composition is obtained by the method of any of items 1 to 24.

83. A haemostatic kit comprising:
   a) a container comprising the dry composition obtained by the method of any of items 1 to 24 or the container according to any of items 74-75,
   b) a container comprising an aqueous medium, and
   c) optionally an outer packaging.

The invention claimed is:

1. A method for preparing a dry composition comprising sequentially:
   a) providing an agent in powder form and an aqueous medium,
   b) mixing the agent in powder form and the aqueous medium to obtain a paste,
   c) subjecting the paste to a reduced pressure thereby expanding the paste,
   d) freezing the expanded paste, and
   e) drying the paste.

2. The method according to claim 1, wherein the reduced pressure is a pressure of at least 10 mbar less than ambient pressure.

3. The method according to claim 1, wherein the volume of the paste is increased by about a factor 1.05 to about a factor 2.0 as a result of the reduced pressure.

4. The method according to claim 1, wherein the density of the paste is decreased by at least a factor 0.95 as a result of the vacuum expansion.

5. The method according to claim 1, wherein the agent in powder form is a biocompatible polymer.

6. The method according to claim 1, wherein the agent in powder form consists of powder particles which are substantially insoluble in an aqueous medium.

7. The method according to claim 1, wherein the agent in powder form is cross-linked.

8. The method according to claim 1, wherein the agent in powder form is biologically absorbable.

9. The method according to claim 1, wherein the agent in powder form comprises or consists of gelatine.

10. The method according to claim 9, wherein the gelatine is obtained from a micronized gelatine sponge which has been cross-linked by dry heat treatment.

11. The method according to claim 1, wherein the mixing in b) introduces a discontinuous gas phase substantially homogenously dispersed through the paste.

12. The method according to claim 1, wherein the drying is freeze-drying.

13. The method according to claim 1, wherein the agent in powder form and the aqueous medium is further mixed with one or more hydrophilic compounds.

14. The method according to claim 13, wherein the one or more hydrophilic compounds are one or more polyols.

15. The method according to claim 14, wherein the one or more polyols is selected from sugar alcohols, sugars and/or derivatives thereof.

16. The method according to claim 15, wherein the one or more polyols is a sugar alcohol selected from the group consisting of glycol, glycerol, erythritol, threitol, arabitol, xylitol, ribitol, mannitol, sorbitol, dulcitol, fucitol, iditol, inositol, volemitol, isomalt, maltitol, lactitol and polyglycitol.

17. The method according to claim 16, wherein the sugar alcohol is mannitol.

18. The method according to claim 13, wherein the one or more hydrophilic compounds is polyethylene glycol (PEG).

19. The method according to claim 1, wherein the dry composition further comprises one or more bioactive agents capable of stimulating haemostasis, wound healing, bone healing, tissue healing and/or tendon healing.

20. The method according to claim 19, wherein the bioactive agent is thrombin.

21. The method according to claim 1, wherein the dry composition further comprises an extrusion enhancer.

22. The method according to claim 1, wherein the paste obtained in b) is transferred into a container suitable for expansion, freezing and drying of the paste.

23. The method according to claim 22, wherein the container is a medical delivery device suitable for reconstituting the dry composition and dispensing a paste.

24. The method according to claim 1, further comprising adding a suitable amount of an aqueous medium to the dry composition, thereby reconstituting the dry composition.

25. The method according to claim 1, wherein the dry composition reconstitutes without mechanical mixing to form a ready-to-use paste within less than about 30 seconds.

* * * * *